US 8,709,747 B2

(12) United States Patent
Brevet et al.

(10) Patent No.: US 8,709,747 B2
(45) Date of Patent: Apr. 29, 2014

(54) BIPHOTONIC PHOTOSENSITIZERS, NANOPARTICLES CONTAINING THE SAME AND THEIR USE AS DRUGS

(75) Inventors: David Brevet, Narbonne (FR); Laurence Raehm, Montpellier (FR); Mireille Blanchard-Desce, Rennes (FR); Olivier Mongin, Rennes (FR); Magali Gary-Bobo-Sable-Teychene, Montpellier (FR); Marcel Garcia, Prades-le-lez (FR); Alain Morere, Les Matelles (FR); Jean-Olivier Durand, Palavas les Flots (FR)

(73) Assignees: Centre National de la Recherche Scientifique, Paris (FR); Universite de Rennes 1, Rennes (FR); I.N.S.E.R.M. (Institut National de la Sante et de la Recherche Medicale), Paris (FR); Universite Montpellier 2 Sciences et Techniques, Montpellier (FR)

( * ) Notice: Subject to any disclaimer, the term of this patent is extended or adjusted under 35 U.S.C. 154(b) by 0 days.

(21) Appl. No.: 13/516,010

(22) PCT Filed: Dec. 7, 2010

(86) PCT No.: PCT/EP2010/069035
§ 371 (c)(1),
(2), (4) Date: Aug. 27, 2012

(87) PCT Pub. No.: WO2011/073054
PCT Pub. Date: Jun. 23, 2011

(65) Prior Publication Data
US 2013/0065849 A1    Mar. 14, 2013

(30) Foreign Application Priority Data
Dec. 15, 2009   (EP) ...................................... 09306238

(51) Int. Cl.
*B82Y 30/00*    (2011.01)
*C07F 7/10*    (2006.01)
*C07F 7/18*    (2006.01)
*C07F 7/08*    (2006.01)
*C07H 23/00*    (2006.01)
*A61K 49/00*    (2006.01)
*C07D 333/16*    (2006.01)
*C07D 333/20*    (2006.01)
*C07D 495/04*    (2006.01)
*C07D 409/10*    (2006.01)
*C07D 409/02*    (2006.01)

(52) U.S. Cl.
USPC ............... 435/34; 514/35; 514/443; 514/444; 514/63; 536/17.6; 546/14; 549/4; 549/50; 549/59; 977/773; 977/896; 977/906; 977/915

(58) Field of Classification Search
None
See application file for complete search history.

(56) References Cited

FOREIGN PATENT DOCUMENTS

| WO | 95/32001 A1 | 11/1995 |
|----|-------------|---------|
| WO | 2004/067508 A2 | 8/2004 |
| WO | 2008/030624 A2 | 3/2008 |

OTHER PUBLICATIONS

Mongin et al., caplus an 2007:199833 (2007).*
Mongin a et al: "Synthesis, Fluorescence, and two-photon absorption of a series of elongated rod-like and banana-shaped quadrupolar fluorophores: A comprehensive study of structure-property relationship", Chem. Eur. J. , vol. 13, 2007, pp. 1481-1498, XP002574594, Scheme 7,compound 31, Cited in ISR.
Ohulchanskyy T Y et al: "organically modified silica nanoparticles with covalently incorporated photosensitizer for photodynamic therapy of cancer", Nano Letters, ACS, Washington, DC, US, vol. 7, No. 9, Jan. 1, 2007, pp. 2835-2842, XP002515000, ISSN: 1530-6984 [retrieved on Aug. 25, 2007] * abstract, Cited in ISR.
Chaleix V et al: "RGD-porphyrin conjugates: Synthesis and potential application in photodynamic therapy", European Journal of Organic Chemistry, Wiley-VCH, Weinheim; DE, vol. 8, Jan. 1, 2003, pp. 1486-1493, XP002373372, ISSN: 1434-193X * abstract, Cited in ISR.

(Continued)

*Primary Examiner* — Sun Jae Yoo
(74) *Attorney, Agent, or Firm* — Young & Thompson

(57) ABSTRACT

The invention relates to compounds of formula (I)

(I)

$Z_1\text{—}(\ )_t$, $Z_5$, $Z_6$, $Z_2\text{—}(\ )_u$, $Y_1$, $Y_2$, $Z_6$, $Z_5$, $Z_3$, $Z_4$ wherein
the groups A and B represent independently from each other —CH=CH—, or —C≡C—,
the terms t, u, v, w represent, independently from each other, values ranging from 0 to 9,
the groups $Y_1$ and $Y_2$ can represent independently from each other an alkyl group (linear, branched or substituted) carrying from 1 to 9 carbon atoms,
the groups $Z_1$, $Z_2$, $Z_3$, and $Z_4$ can represent independently from each other a chemically reactive group W, such as OH, $NH_2$, SH,
the groups $Z_5$ and $Z_6$ represent independently from each other a hydrogen atom,
silica nanoparticles functionalized by these compounds, and their use as drugs.

20 Claims, 12 Drawing Sheets

(56) References Cited

OTHER PUBLICATIONS

Indrajit Roy et al.: "Ceramic-Based Nanoparticles Entrapping Water-Insoluble Photosensitizing Anticancer Drugs: A Novel Drug-Carrier System for Photodynamic Therapy", Published on Web Jun. 10, 2003, pp. 7860-7865, Cited in Specification.

Harapriya Rath et al.: "Core-Modified Expanded Porphyrins with Large Third-Order Nonlinear Optical Response", Published on Web Jul. 28, 2005, pp. 11608-11609, Cited in Specification.

Kazuya Ogawa et al.: "Water-Soluble Bis(imidazolylporphyrin) Self-Assemblies with Large Two-Photon Absorption Cross Sections as Potential Agents for Photodynamic Therapy", Journal of Medicinal Chemistry, 2006, vol. 49, No. 7, pp. 2276-2283, Cited in Specification.

Kazuya Ogawa et al.: "Strong Two-Photon Absorption of Self-Assembled Butadiyne-Linked Bisporphyrin", Published on Web Oct. 11, 2003, J. Am. Chem. Soc. 9 vol. 125, No. 44, 2003, pp. 13356-13357, Cited in Specification.

Rajneesh Misra et al.: "Modified (22Π) Smaragdyrins with Large Two-Photon Absorption Cross Section: A Structure Function Correlation", Published on Web Jan. 14, 2006, Organic Letters 2006 vol. 8, No. 4, 629-631, Cited in Specification.

Deok Yun Kim et al.: "Large Two-Photon Absorption (TPA) Cross-Section of Directly Linked Fused Diporphyrins", Published on Web Mar. 15, 2005, In Final Form: Mar. 4, 2005, 109, 2996-2999, Cited in Specification.

Sehoon Kim et al.: "Organically Modified Silica Nanoparticles Co-Encapsulating Photosensitizing Drug and Aggregation-Enhanced Two-Photon Absorbing Fluorescent Dye Aggregates for Two-Photon Photodynamic Therapy", Published in final edited form as: J Am Chem Soc. Mar. 7, 2007; 129(9): 2669-2675. doi:10.1021/ja0680257, pp. 1-20, Cited in Specification.

Mikhail Drobizhev et al.: "Resonance enhancement of two-photon absorption in porphyrins", Chemical Physics Letters 355 (2002) 175-182, in final form Jan. 28, 2002, Cited in Specification.

Hazel A. Collins et al.: "Blood-vessel closure using photosensitizers engineered for two-photon excitation", Published online: May 30, 2008; doi:10.1038/nphoton.2008.100, pp. 1-5, Cited in Specification.

Bhawalkar, et al.: "Two-Photon Photodynamic Therapy", Journal of Clinical Laser Medicine & Surgery, vol. 15, No. 5, 1997, Photonics Research Laboratory, Department of Chemistry State University of New York at Buffalo Buffalo, NY 14260-3000, pp. 201-204, Cited in Specification.

Tae Kyu Ahn et al.: "Relationship between Two-Photon Absorption and the Π-Conjugation Pathway in Porphyrin Arrays through Dihedral Angle Control", Published on Web Jan. 17, 2006, J. Am. Chem. Soc. 2006, 128, 1700-1704, vol. 128, No. 5, 2006, Cited in Specification.

International Search Report, dated Jan. 26, 2011, from corresponding PCT application.

* cited by examiner

BIPHOTONIC PHOTOSENSITIZERS, NANOPARTICLES CONTAINING THE SAME AND THEIR USE AS DRUGS

The present invention relates to biphotonic photosensitizers, silica nanoparticles containing at least one of said biphotonic photosensitizers, and the use of said biphotonic photosensitizers and nanoparticles as drugs.

Photosensitizers are compounds that can absorb irradiation in a defined wavelength range, for example in the visible or near infra-red spectrum. The irradiation absorption excites the photosensitizers to an electronic state of higher energy. Photosensitizers are able to transfer their excitation energy to other molecules (in particular to molecular oxygen), but energy can also be released through other competitive mechanisms, including fluorescence.

Most of one-photon photosensitizers are porphyrin derivatives; however single porphyrins have low two-photon absorption (TPA) cross-sections in the spectral range of interest (15 GM for tetraphenylporphine) (Drobizhev et al., *Chem. Phys. Lett.* 2002, 355, 175-182.). Giant but one-photon resonant TPA cross-sections can be obtained with expanded porphyrins (Rath et al., *J. Am. Chem. Soc.* 2005, 127, 11608-11609) (Misra et al., *Org. Lett.* 2006, 8, 629-631.), diyne porphyrin dimers (Ogawa et al., *J. Am. Chem. Soc.* 2003, 125, 13356-13357), fused porphyrin dimers (Kim et al, *J. Phys. Chem. A* 2005, 109, 2996-2999), porphyrin arrays (Ahn et al, *Am. Chem. Soc.* 2006, 128, 1700-1704), or supramolecular assemblies (Ogawa et al., *J. Am. Chem. Soc.* 2003, 125, 13356-13357) (Ogawa, et al., *J. Med. Chem.* 2006, 49, 2276-2283) however at the expense of a definite decrease of the fluorescence quantum yield (if not suppression) and residual one-photon absorption overlapping with the TPA band.

It should be stressed that this one-photon resonance enhancement is at the origin of the giant TPA values but also results in a loss of some of the advantages resulting from selective TPA, in particular the 3D resolution.

Molecular two-photon absorption (TPA) has gained increasing attention over recent years, in relation with the wide-ranging applications it offers, such as photodynamic therapy (PDT) (Bhawalkar et al., *J. Clin. Laser Med. Surg.* 1997, 15, 201-204) (Kim et al., *J. Am. Chem. Soc.* 2007, 129, 2669-2675) (Collins et al., *Nat Photon* 2008, 2, 420). This application requires both pulsed sources (to increase the probability of this nonlinear process) i.e. femtosecond, picosecond, or possibly nanosecond lasers and chromophores exhibiting very high TPA cross-sections (intense but also broad TPA bands are highly desirable due to the versatility this offers in terms of laser sources), allowing either more efficient excitation or decrease of the excitation intensity (use of less expensive laser sources). This also offers a number of advantages for biological or biomedical applications, including the ability for highly selective excitation in biological media, intrinsic three-dimensional resolution, and reduction of photodamage by using lower excitation intensities. Depending on the targeted applications, TPA chromophores have to fulfill different requirements: molecular engineering depends on the desired application, in terms of spectral range and specific additional features. For instance, in the case of biological imaging, high fluorescence quantum yields, photostability and harmless are requested, whereas for PDT high singlet oxygen production is needed.

Photodynamic therapy relies on photosensitizer. Photosensitizers specifically locate in malignant tissues, and transmit their energy to the excess of molecular oxygen in their surrounding, when they are excited by a light source of suitable wavelength in the visible or near infra-red spectrum.

The activation of the photosensitizer generates reactive oxygen species such as free radicals and singlet oxygen. These reactive oxygen species, and particularly singlet oxygen, are toxic for the cells that surround them, and lead to the destruction of the malignant tissue in their close vicinity. These reactive oxygen species oxidise the cell membranes and lead to irreversible damages of the cells containing the photosensitizer.

Photodynamic therapy is based on a two-fold selectivity: the selective irradiation of the tissues containing the photosensitizer; and the selectivity of the photosensitizer for the targeted tissues. Without irradiation, the photosensitizers are not toxic, thus their diffusion through the organism is of little consequence.

A photosensitizer has to show several properties in order to be suitable for in-vivo use. It has to be easily targetable towards cancer cells, to be hydro soluble, to be easy to produce and to functionalize, to be non toxic when not exposed to irradiations, to be stable toward the common enzymes, and to be quickly discarded by healthy tissues. However, most of the molecules belonging to the photosensitizer class are hydrophobic and their introduction, particularly by parenteral injection, in the organism requires elaborate preparations. Such preparations are in particular colloidal suspensions, liposomes, nanoparticles. These formulations enable the stabilisation of the photosensitizers in aqueous medium and allow their transportation to the cancer cells. Targeting of the cancer cells is particularly achieved thanks to specific biotargeting elements. Another constrain of these preparations is to keep the potency of the photosensitizers, that means their capacity to generate reactive oxygen species from the molecular oxygen around them. Some type of preparation interacts with the excited states of the photosensitizer and decreases the photosensitizer potency.

The preparation of photosensitizer in silica nanoparticles, is acknowledged as a promising way for photodynamic therapy. Such preparation are described in WO2004/067508; WO2008/030624; I. Roy et al., *J. Am. Chem. Soc.* 2003, 125, 7860-7865.

However, these preparations often lead to early leakage of the photosensitizer in the organism before the photosensitizer reaches the targeted cancer cells.

One of the aims of the invention is to provide new biphotonic photosensitizers which can be further functionalized.

Another aim of the invention is to provide new biphotonic photosensitizers which can be incorporated in silica nanoparticles, and covalently linked to said silica nanoparticles.

One of the aims of the invention is to provide silica nanoparticles functionalized by biphotonic photosensitizers without loss of biphotonic absorption properties of said biphotonic photosensitizers.

Another aim of the invention is to provide non-toxic silica nanoparticles functionalized by biphotonic photosensitizers.

Another aim of the invention is to provide silica nanoparticles functionalized by biphotonic photosensitizers, and said silica nanoparticles being also functionalised to target specific cells.

Another aim of the invention is to provide silica nanoparticles functionalized by biphotonic photosensitizers, and said silica nanoparticles being also functionalised to avoid the monophotonic excitation of said photosensitizers.

The present invention aims first at combining both fluorescence and singlet oxygen generation in the same biphotonic photosensitizer (i.e. significant fluorescence and singlet oxygen quantum yields) for biomedical applications: targeting, monitoring (fluorescence imaging) and therapy (photosensitized production of singlet oxygen for PDT); second at avoiding leakage of the photosensitizer out of the nanoparticle to keep the full potency of the photosensitizer until irradiation of the cancer cells.

The invention relates to a compound of formula (I): wherein

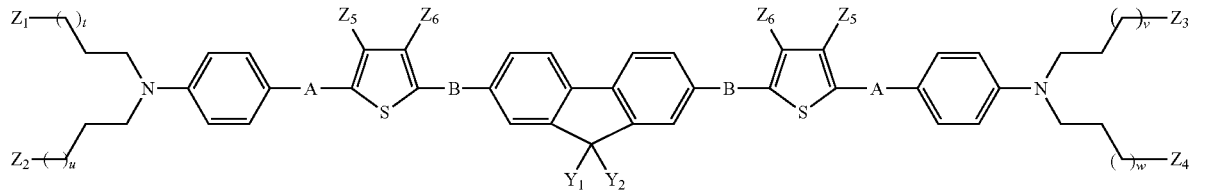

(I)

the groups A and B represent independently from each other —CH=CH—, or —C≡C—, the terms t, u, v, w represent, independently from each other, values ranging from 0 to 9, the groups $Y_1$ and $Y_2$ represent independently from each other:
- a hydrogen atom, or an alkyl group (linear, branched or substituted) carrying from 1 to 9 carbon atoms, or
- a polyethylene glycol chain of formula: —$(CH_2)_n$—O—$(CH_2CH_2O)_m CH_3$, wherein n<4 and m varies from 1 to 6, or
- an ammonium group of formula: —$(CH_2)_p$—$NR_3^+X^-$, wherein $X^-$ is selected among halogens, tosylate, sulphate, phosphate, $NTf_2$, $PF_6$ anions, p varies from 1 to 6, and R is an alkyl chain linear or branched, from 1 to 9 carbon atoms, the groups $Z_1$, $Z_2$, $Z_3$, and $Z_4$ represent independently from each other:
- a hydrogen atom, or
- a chemically reactive group W, such as OH, $NH_2$, SH,
- a group V used as a molecular clip constituted by -α-β-δ, wherein:
  - α is a functional linking group such as a carbamate, an urea, a thiocarbamate, an amide, and
  - β is an alkyl chain, linear or branched, containing from 1 to 9 carbon atoms, and
  - δ is a $Si(OR')_3$ group, wherein R' is an alkyl chain, linear or branched, from 1 to 9 carbon atoms, or
- an aryl, aryloxy, aralkyl, aralkyloxy, heteroaryl, heteroaryloxy group, ranging from 1 to 10 carbon atoms, containing a chemically reactive group W as above defined, or
- an alkyl chain possibly unsaturated, linear, branched or substituted, ranging from 1 to carbon atoms, or
- an alkyl chain possibly unsaturated, linear, branched or substituted, ranging from 1 to carbon atoms, and containing a chemically reactive group W as above defined, or
- a polyethylene glycol chain of formula —$(CH_2)_q$—O—$(CH_2CH_2O)_r$—$CH_2CH_2$—W, wherein q<4 and r varies from 1 to 6, and W is a chemically reactive group as above defined, provided at least one of the $Z_1$, $Z_2$, $Z_3$ or $Z_4$ groups represents:
- a chemically reactive group W, such as OH, $NH_2$, SH, or
- a group V used as a molecular clip constituted by -α-β-δ, wherein:
  - α is a functional linking group such as a carbamate, an urea, a thiocarbamate, an amide, and
  - β is an alkyl chain, linear or branched, containing from 1 to 9 carbon atoms, and
  - δ is a $Si(OR')_3$ group, wherein R' is an alkyl chain, linear or branched, from 1 to 9 carbon atoms, or
- an aryl, aryloxy, aralkyl, aralkyloxy, heteroaryl, heteroaryloxy group, ranging from 1 to 10 carbon atoms, containing a chemically reactive group W as above defined, or
- an alkyl chain possibly unsaturated, linear, branched or substituted, ranging from 1 to carbon atoms, and containing a chemically reactive group W as above defined, or
- a polyethylene glycol chain of formula —$(CH_2)_q$—O—$(CH_2CH_2O)_r CH_2CH_2$—W, wherein q<4 and r varies from 1 to 6, and W is a chemically reactive group as above defined, the groups $Z_5$ and $Z_6$ represent independently from each other:
- a hydrogen atom, or
- an alkyl chain possibly unsaturated, linear, branched or substituted, ranging from 1 to 9 carbon atoms, or
- an alkoxy group, a carbocyclic group, a heterocyclic group, an aromatic group, ranging from 1 to 9 carbon atoms, or
- $Z_5$ and $Z_6$ are linked together through an ethylene glycol group, thus providing a 3,4-ethylenedioxythiophene group (EDOT) with the thiophene group they are linked to,

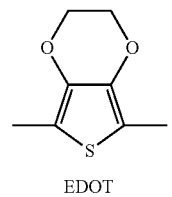

EDOT

The term "chemically reactive group" designates a chemical function containing at least one nucleophilic center, wherein said nucleophilic center can be formed of atoms such as oxygen, nitrogen or sulphur. A nucleophilic chemical function can be for example an alcohol, an amine, a thiol, an hydrazine, an hydroxylamine.

The term "molecular clip" designates a chemical group containing at least one function susceptible of being incorporated in the structure of a material, and thus links the compound that is functionalised by said molecular clip to the material. The alkoxysilane groups (8 moieties) of the molecular clip groups (V group) act as anchor for the compound toward a type of material, in the present invention said material being silica (silicium oxide).

As described above, the group V is constituted by -α-β-δ, wherein α is a functional linking group. The alkyl chains of the terminal tertiary amines of the core having two-photon absorption properties are linked to the V group through the α group. Thus, in case $Z_1$ is a V group, $Z_1$ can be represented as:

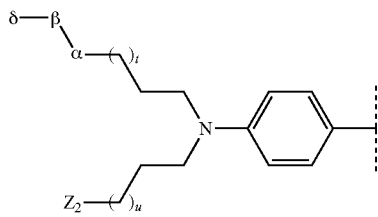

The term "functional linking group" designates a chemical function that is substituted by at least two different entities and that creates a covalent link between theses entities. Said functional linking group is obtained through the chemical reaction of at least two chemical functions, each function being carried by one of said entities that are linked to the functional group.

The compounds of formula (I) can be used as photosensitizers. The term "photosensitizer" designates a light-absorbing substance that initiates a photochemical or photophysical reaction in another substance (molecule), and is not structurally modified in the reaction. In the present invention, the initiated photochemical reaction is the generation of singlet oxygen. Singlet dioxygen ($^1O_2$) molecules are obtained from triplet dioxygen molecules ($^{III}O_2$) by excitation transfer from the excited photosensitizer to the dioxygen molecule in triplet electronic state.

The term "halogen" designates fluorine, chlorine, bromine, iodine, astatine atoms.

Preferably $X^-$ is selected among anions that do not totally quench the fluorescence of the compound of formula (I). Total quenching of the fluorescence is achieved when the fluorescence quantum yield is reduced below 5%, particularly 2%, particularly 1%, particularly 0.1%. and is particularly of 0%.

The term "fluorescence quantum yield" designates the ratio of the number of emitted photons to the number of absorbed photons. This yield is the fraction of excited molecules that return to the ground state with emission of fluorescence photons.

The term "quench the fluorescence" designates the decrease of fluorescence intensity of the compound. A variety of processes can result in quenching, such as excited state reactions, energy transfer, complex-formation and collisional quenching. As a consequence, quenching is often heavily dependent on pressure and temperature. Molecular oxygen and the iodide ion are common chemical quenchers. Quenching by energy transfer to molecular oxygen generate singlet oxygen. Generation of singlet oxygen and other reactive oxygen species is a characteristic of the compounds according to the present invention.

Compounds according to the present invention are constituted of a large conjugated core having two-photon absorption properties, said core being delimited on its extremities by the ternary nitrogen atoms. Said core has the following formula:

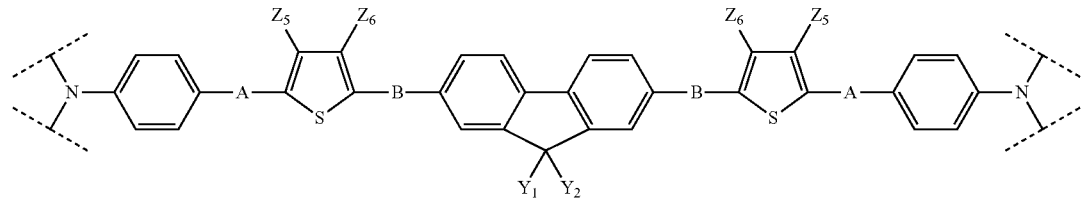

The core is functionalised on the central fluorene ring by side chains $Y_1$ and $Y_2$ as defined above, and on the terminal tertiary amine by alkyl groups carrying $Z_1$ to $Z_4$ groups.

Groups $Y_1$ and $Y_2$ are important for two reasons:
preventing π staking, and
modulating the solubility of the compound.

The aromatic rings of the compounds according to the present invention are prone to it staking, which interfere with electronic properties of the compound. Functionalization of $Y_1$ and $Y_2$ positions by bulky groups prevents aggregation of the compounds.

The good solubility of the compound of the present invention in both organic and aqueous medium is important. Functionalization of positions $Y_1$ and $Y_2$ by hydrophilic groups such as ammonium salt or polyethylene glycol chains enhances the solubility of the compound in aqueous systems.

According to an advantageous embodiment, the invention relates to a compound of formula (I) as defined above, wherein at least one of the $Z_1$, $Z_2$, $Z_3$ or $Z_4$ groups represents a W chemical group such as defined above, or a group V used as a molecular clip such as defined above.

The groups V and W represent two different types of compounds.

The compounds functionalized by a W group are important milestones in the synthesis of photosensitizers because of their W group which can be further functionalised without decreasing the biphotonic properties of the compound.

The compounds functionalized by a V group are important because they can be readily incorporated in silica nanoparticles through the alkoxysilane functions of the 8 moieties.

According to an advantageous embodiment, the invention relates to a compound of formula (I) as defined above, wherein at least one of the $Z_1$, $Z_2$, $Z_3$ or $Z_4$ groups represents a W chemical group such as defined above.

The compound of formula (I) wherein

According to an advantageous embodiment, the invention relates to a compound of formula (I) as defined above, wherein at least one of the $Z_1$, $Z_2$, $Z_3$ or $Z_4$ groups represents a group V used as a molecular clip such as defined above.

According to an advantageous embodiment, the invention relates to a compound of formula (I) as defined above, wherein
the moieties $Z_5$ and $Z_6$ represent:
  a hydrogen atom, or
  $Z_5$ and $Z_6$ are linked together through an ethylene glycol group, thus providing a 3,4-ethylenedioxythiophene group (EDOT) with the thiophene group they are linked to.

EDOT groups are stronger electron donor than un-substituted thiophene groups. Electron donor properties of the groups constituting the compound modifies the $O_2$ (two-photon absorption cross section) of the said compound.

Increased electron donor effect shifts the absorption band of the compound toward infra-red wavelengths.

According to an advantageous embodiment, the invention relates to a compound of formula (II):

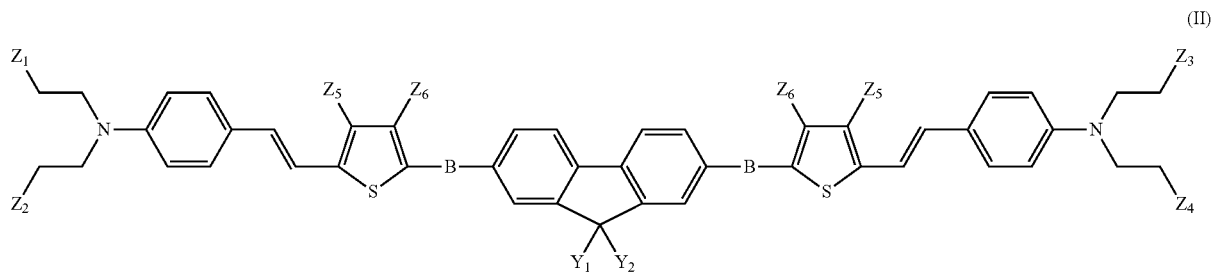

(II)

wherein $Z_1$, $Z_2$, $Z_3$, $Z_4$, $Z_5$, $Z_6$, $Y_1$, $Y_2$ and B groups are as defined above.

According to an advantageous embodiment, the invention relates to a compound of formula (II) as defined above, wherein at least one of the $Z_1$, $Z_2$, $Z_3$ or $Z_4$ groups represents a W chemical group or a group V used as a molecular clip such as defined above.

According to an advantageous embodiment, the invention relates to a compound of formula (II) as defined above, wherein at least one of the $Z_1$, $Z_2$, $Z_3$ or $Z_4$ groups represents a W chemical group such as defined above.

According to an advantageous embodiment, the invention relates to a compound of formula (II) as defined above, wherein at least one of the $Z_1$, $Z_2$, $Z_3$ or $Z_4$ groups represents a group V used as a molecular clip such as defined above.

According to an advantageous embodiment, the invention relates to a compound of formula (III):

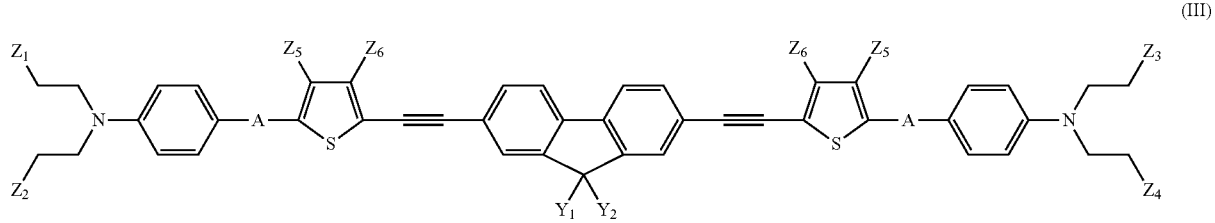

(III)

wherein $Z_1$, $Z_2$, $Z_3$, $Z_4$, $Z_5$, $Z_6$, $Y_1$, $Y_2$ and A groups are as defined above.

According to an advantageous embodiment, the invention relates to a compound of formula (III) as defined above, wherein at least one of the $Z_1$, $Z_2$, $Z_3$ or $Z_4$ groups represents a W chemical group, or a group V used as a molecular clip such as defined above.

According to an advantageous embodiment, the invention relates to a compound of formula (III) as defined above, wherein at least one of the $Z_1$, $Z_2$, $Z_3$ or $Z_4$ groups represents a W chemical group such as defined above.

According to an advantageous embodiment, the invention relates to a compound of formula (III) as defined above, wherein at least one of the $Z_1$, $Z_2$, $Z_3$ or $Z_4$ groups represents a group V used as a molecular clip such as defined above.

According to another embodiment the invention relates to a compound of formula (IV):

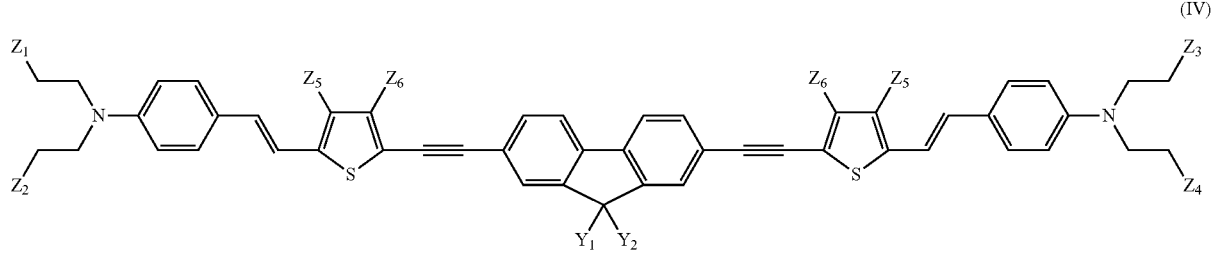

(IV)

wherein $Z_1$, $Z_2$, $Z_3$, $Z_4$, $Z_5$, $Z_6$, $Y_1$, $Y_2$ and B groups are as defined above.

The compounds of formula (IV) are particularly well adapted to the present invention, because of the specific arrangement of double and triple bonds which aims at optimizing the two-photon absorption/photostability trade-off of the compounds.

According to an advantageous embodiment, the invention relates to a compound of formula (IV) as defined above, wherein at least one of the $Z_1$, $Z_2$, $Z_3$ or $Z_4$ groups represents a W chemical group, or a group V used as a molecular clip such as defined above.

According to an advantageous embodiment, the invention relates to a compound of formula (IV) as defined above, wherein at least one of the $Z_1$, $Z_2$, $Z_3$ or $Z_4$ groups represents a W chemical group as defined above.

According to an advantageous embodiment, the invention relates to a compound of formula (IV) as defined above, wherein at least one of the $Z_1$, $Z_2$, $Z_3$ or $Z_4$ groups represents a group V used as a molecular clip such as defined above.

According to an advantageous embodiment, the invention relates to a compound of formula (IV) as defined above, wherein the groups $Z_5$ and $Z_6$ represent:
  a hydrogen atom, or
  $Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound of formula (IV) as defined above, wherein at least one of the $Y_1$ and $Y_2$ groups represents an alkyl group (linear, branched or substituted) carrying from 1 to 9 carbon atoms, and at least one of the $Z_1$, $Z_2$, $Z_3$ or $Z_4$ groups represents a W chemical group as defined above.

According to an advantageous embodiment, the invention relates to a compound of formula (IV) as defined above, wherein at least one of the $Y_1$ and $Y_2$ groups represents an alkyl group (linear, branched or substituted) carrying from 1 to 9 carbon atoms, and at least one of the $Z_1$, $Z_2$, $Z_3$ or $Z_4$ groups represents a group V used as a molecular clip as defined above.

According to an advantageous embodiment, the invention relates to a compound of formula (IV) as defined above, wherein the $Y_1$ and $Y_2$ groups represent alkyl groups (linear, branched or substituted) carrying from 1 to 9 carbon atoms, and at least one of the $Z_1$, $Z_2$, $Z_3$ or $Z_4$ groups represents a W chemical group as defined above.

According to an advantageous embodiment, the invention relates to a compound of formula (IV) as defined above, wherein the $Y_1$ and $Y_2$ groups represent alkyl groups (linear, branched or substituted) carrying from 1 to 9 carbon atoms, and at least one of the $Z_1$, $Z_2$, $Z_3$ or $Z_4$ groups represents a group V used as a molecular clip as defined above.

According to an advantageous embodiment, the invention relates to a compound of formula (IV) as defined above, wherein at least one of the $Y_1$ and $Y_2$ groups represents a polyethylene glycol chain of formula: —$(CH_2)_n$—O—$(CH_2CH_2O)_m CH_3$, wherein n<4 and m varies from 1 to 6, and at least one of the $Z_1$, $Z_2$, $Z_3$ or $Z_4$ groups represents a W chemical group as defined above.

The functionalization of at least one of the $Y_1$ and $Y_2$ groups by a polyethylene glycol chain increases the solubility of the compound in aqueous solvents.

According to an advantageous embodiment, the invention relates to a compound of formula (IV) as defined above, wherein at least one of the $Y_1$ and $Y_2$ groups represents a polyethylene glycol chain of formula: —$(CH_2)_n$—O—$(CH_2CH_2O)_m CH_3$, wherein n<4 and m varies from 1 to 6, and at least one of the $Z_1$, $Z_2$, $Z_3$ or $Z_4$ groups represents a group V used as a molecular clip as defined above.

According to an advantageous embodiment, the invention relates to a compound of formula (IV) as defined above, wherein the $Y_1$ and $Y_2$ groups represent polyethylene glycol chains of formula: —$(CH_2)_n$—O—$(CH_2CH_2O)_m CH_3$, wherein n<4 and m varies from 1 to 6, and at least one of the $Z_1$, $Z_2$, $Z_3$ or $Z_4$ groups represents a W chemical group as defined above.

According to an advantageous embodiment, the invention relates to a compound of formula (IV) as defined above, wherein the $Y_1$ and $Y_2$ groups represent polyethylene glycol chains of formula: —$(CH_2)_n$—O—$(CH_2CH_2O)_m CH_3$, wherein n<4 and m varies from 1 to 6, and at least one of the $Z_1$, $Z_2$, $Z_3$ or $Z_4$ groups represents a group V used as a molecular clip as defined above.

According to an advantageous embodiment, the invention relates to a compound as defined above, wherein at least one of the $Z_1$, $Z_2$, $Z_3$ or $Z_4$ groups represents a W chemical group, consisting in OH, $NH_2$, SH functions, said compound having one of the following (V), (VI), (VII), (VIII), or (IX) formula:

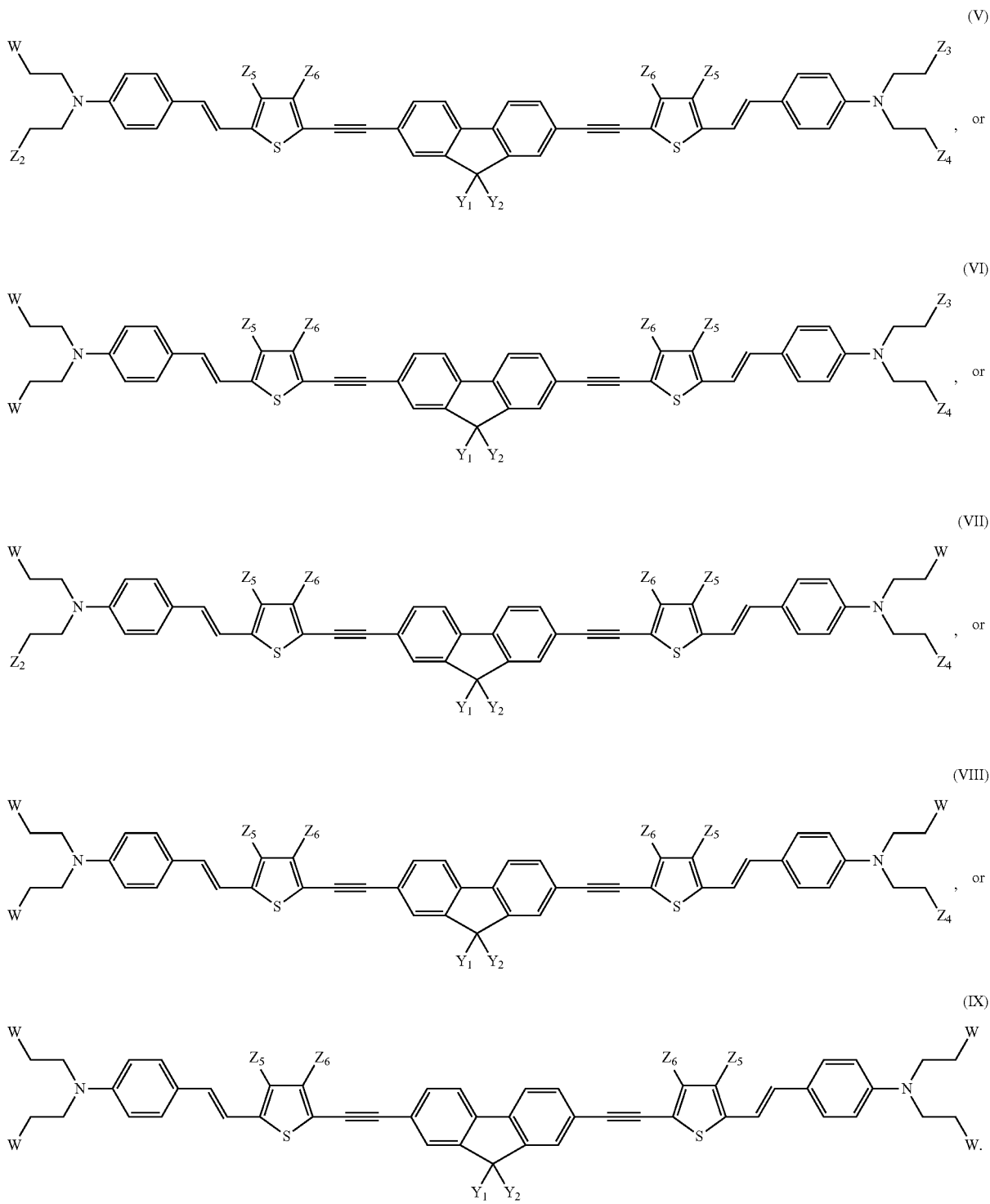

It is advantageous for the compounds according to the present invention to contain more than one chemically reactive group (W group), because it allows an increased reactivity of the compounds toward further chemical modifications, and the possibility to functionalise the compound with different functions.

According to an advantageous embodiment, the invention relates to a compound of formula (V), (VI), (VII), (VIII), or (IX) as defined above, wherein the groups $Z_5$ and $Z_6$ represent:

a hydrogen atom, or $Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound of formula (V), (VI), (VII), (VIII), or (IX) as defined above, wherein at least one of the $Y_1$ and $Y_2$ groups represent an alkyl group (linear, branched or substituted) carrying from 1 to 9 carbon atoms.

According to an advantageous embodiment, the invention relates to a compound of formula (V), (VI), (VII), (VIII), or (IX) as defined above, wherein at least one of the $Y_1$ and $Y_2$ groups represent an alkyl group (linear, branched or substituted) carrying from 1 to 9 carbon atoms, and
the groups $Z_5$ and $Z_6$ represent:
a hydrogen atom, or
$Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound of formula (V), (VI), (VII), (VIII), or (IX) as defined above, wherein the $Y_1$ and $Y_2$ groups represent alkyl groups (linear, branched or substituted) carrying from 1 to 9 carbon atoms.

According to an advantageous embodiment, the invention relates to a compound of formula (V), (VI), (VII), (VIII), or (IX) as defined above, wherein the $Y_1$ and $Y_2$ groups represent alkyl groups (linear, branched or substituted) carrying from 1 to 9 carbon atoms, and
the groups $Z_5$ and $Z_6$ represent:
a hydrogen atom, or
$Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound of formula (V), (VI), (VII), (VIII), or (IX) as defined above, wherein at least one of the $Y_1$ and $Y_2$ groups represents a polyethylene glycol chain of formula: $-(CH_2)_n-O-(CH_2CH_2O)_mCH_3$, wherein n<4 and m varies from 1 to 6.

According to an advantageous embodiment, the invention relates to a compound of formula (V), (VI), (VII), (VIII), or (IX) as defined above, wherein at least one of the $Y_1$ and $Y_2$ groups represents a polyethylene glycol chain of formula: $-(CH_2)_n-O-(CH_2CH_2O)_mCH_3$, wherein n<4 and m varies from 1 to 6, and
the groups $Z_5$ and $Z_6$ represent:
a hydrogen atom, or
$Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound of formula (V), (VI), (VII), (VIII), or (IX) as defined above, wherein the $Y_1$ and $Y_2$ groups represents polyethylene glycol chains of formula: $-(CH_2)_n-O-(CH_2CH_2O)_mCH_3$, wherein n<4 and m varies from 1 to 6.

According to an advantageous embodiment, the invention relates to a compound of formula (V), (VI), (VII), (VIII), or (IX) as defined above, wherein the $Y_1$ and $Y_2$ groups represent polyethylene glycol chains of formula: $-(CH_2)_n-O-(CH_2CH_2O)_mCH_3$, wherein n<4 and m varies from 1 to 6, and
the groups $Z_5$ and $Z_6$ represent:
a hydrogen atom, or
$Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound as defined above, wherein at least one of the $Z_1$, $Z_2$, $Z_3$ or $Z_4$ groups represents a group V used as a molecular clip as defined above,
said compound having one of the following (X), (XI), (XII), (XIII), or (XIV) formula:

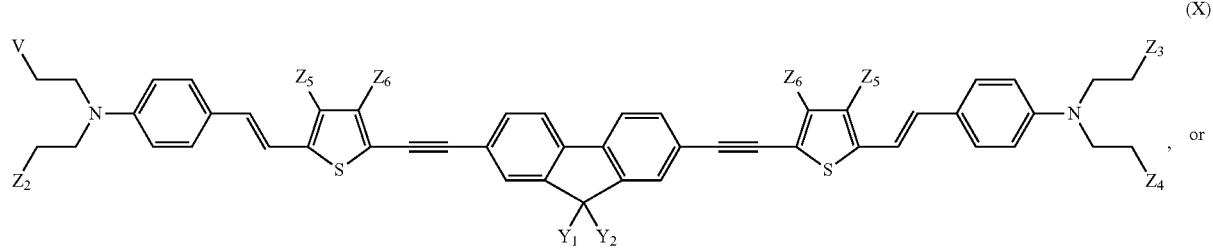

(X)

, or

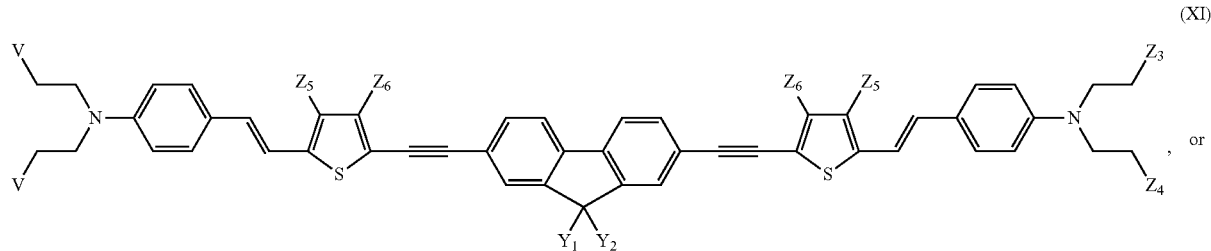

(XI)

, or

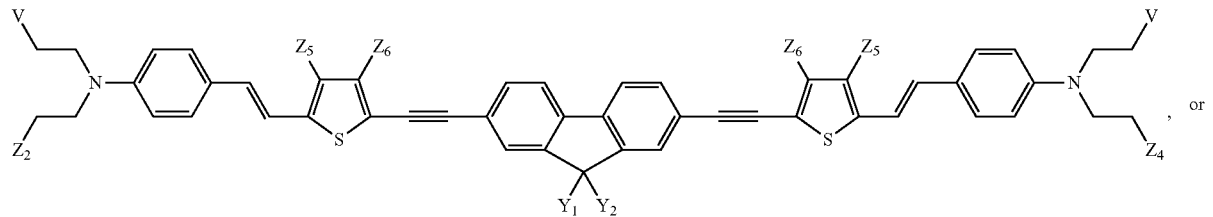

(XII)

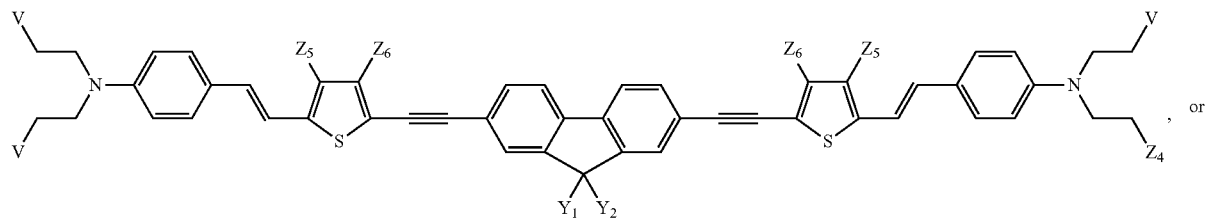

(XIII)

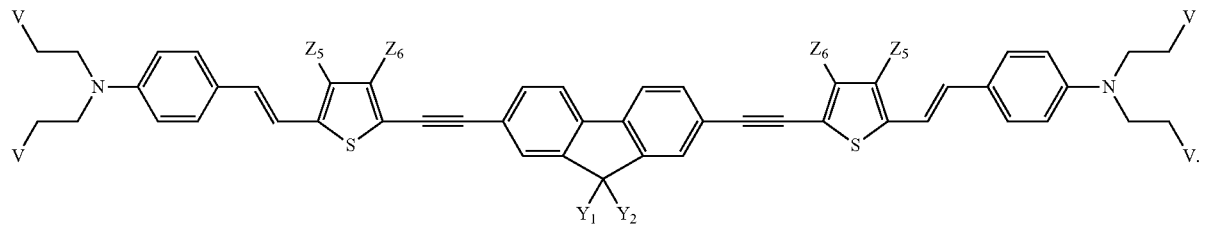

(XIV)

It is advantageous for the compounds according to the present invention to contain more than one molecular clip group (V group). Anchoring of the said compounds in the structure of the nanoparticle increases with the number of groups V present in said compounds.

Compounds comprising several groups V are less prone to leak from the nanoparticle.

According to an advantageous embodiment, the invention relates to a compound of formula (X), (XI), (XII), (XIII), or (XIV) as defined above, wherein at least one of the $Y_1$ and $Y_2$ groups represents an alkyl group (linear, branched or substituted) carrying from 1 to 9 carbon atoms.

According to an advantageous embodiment, the invention relates to a compound of formula (X), (XI), (XII), (XIII), or (XIV) as defined above, wherein at least one of the $Y_1$ and $Y_2$ groups represents an alkyl group (linear, branched or substituted) carrying from 1 to 9 carbon atoms, and
the groups $Z_5$ and $Z_6$ represent:
a hydrogen atom, or
$Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound of formula (X), (XI), (XII), (XIII), or (XIV) as defined above, wherein the $Y_1$ and $Y_2$ groups represent alkyl groups (linear, branched or substituted) carrying from 1 to 9 carbon atoms.

According to an advantageous embodiment, the invention relates to a compound of formula (X), (XI), (XII), (XIII), or (XIV) as defined above, wherein the $Y_1$ and $Y_2$ groups represent alkyl groups (linear, branched or substituted) carrying from 1 to 9 carbon atoms, and the groups $Z_5$ and $Z_6$ represent:

a hydrogen atom, or
$Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound of formula (X), (XI), (XII), (XIII), or (XIV) as defined above, wherein at least one of the $Y_1$ and $Y_2$ groups represents a polyethylene glycol chain of formula: $—(CH_2)_n—O—(CH_2CH_2O)_m CH_3$, wherein n<4 and m varies from 1 to 6.

According to an advantageous embodiment, the invention relates to a compound of formula (X), (XI), (XII), (XIII), or (XIV) as defined above, wherein at least one of the $Y_1$ and $Y_2$ groups represents a polyethylene glycol chain of formula: $—(CH_2)_n—O—(CH_2CH_2O)_m CH_3$, wherein n<4 and m varies from 1 to 6, and
the groups $Z_5$ and $Z_6$ represent:
a hydrogen atom, or
$Z_5$ and $Z_6$ are linked together through an ethylene glycol group, thus providing a 3,4-ethylenedioxythiophene group (EDOT) with the thiophene group they are linked to.

According to an advantageous embodiment, the invention relates to a compound of formula (X), (XI), (XII), (XIII), or (XIV) as defined above, wherein the $Y_1$ and $Y_2$ groups represent polyethylene glycol chains of formula: $—(CH_2)_n—O—(CH_2CH_2O)_m CH_3$, wherein n<4 and m varies from 1 to 6.

According to an advantageous embodiment, the invention relates to a compound of formula (X), (XI), (XII), (XIII), or (XIV) as defined above, wherein the $Y_1$ and $Y_2$ groups represent polyethylene glycol chains of formula: $—(CH_2)_n—O—(CH_2CH_2O)_m CH_3$, wherein n<4 and m varies from 1 to 6, and
the groups $Z_5$ and $Z_6$ represent:
a hydrogen atom, or $Z_5$ and $Z_6$ are linked together through an ethylene glycol group, thus providing a 3,4-ethylenedioxythiophene group (EDOT) with the thiophene group they are linked to.

According to another embodiment the invention relates to a compound of the following formula:

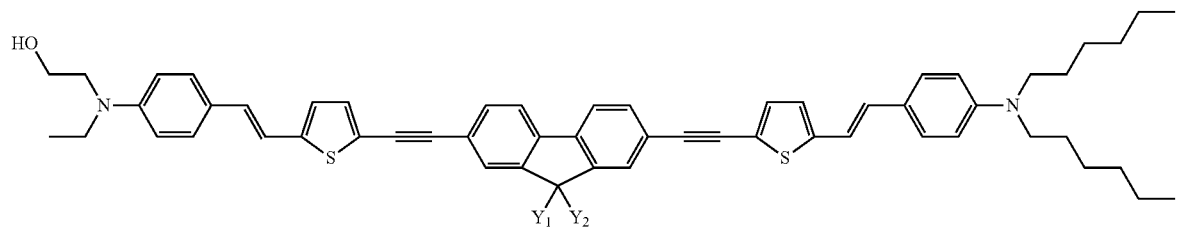

wherein $Y_1$ and $Y_2$ are similar and represent
n-butyl alkyl chain, or
—$(CH_2CH_2)O(CH_2CH_2)O(CH_2CH_2)OCH_3$ groups.

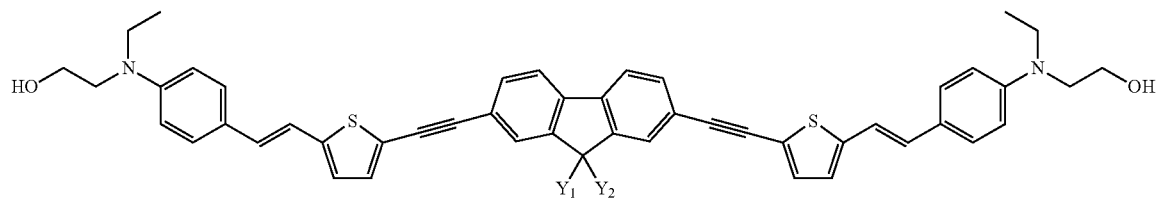

wherein $Y_1$ and $Y_2$ are similar and represent
n-butyl alkyl chain, or
—$(CH_2CH_2)O(CH_2CH_2)O(CH_2CH_2)OCH_3$ groups.

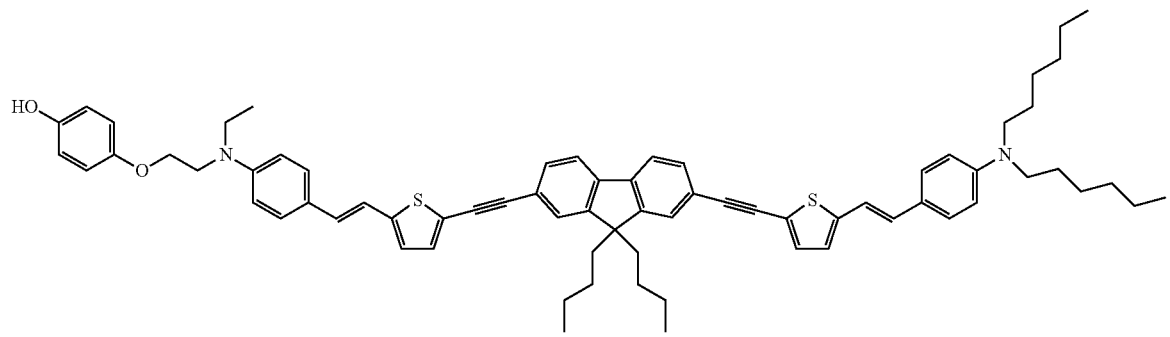

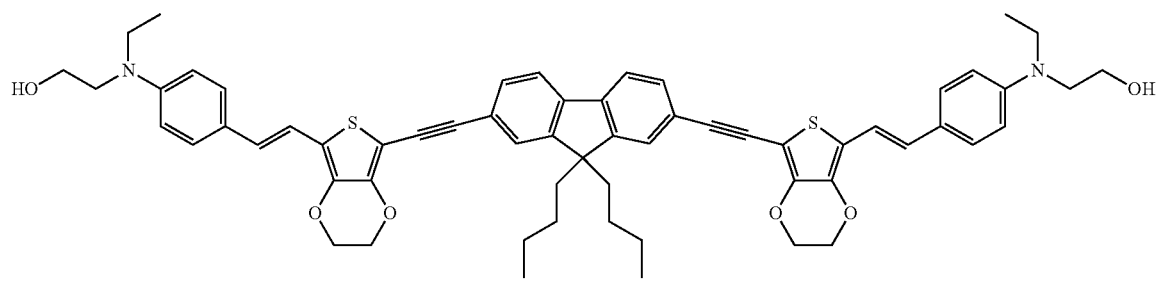

According to another embodiment the invention relates to a compound of the following formula:
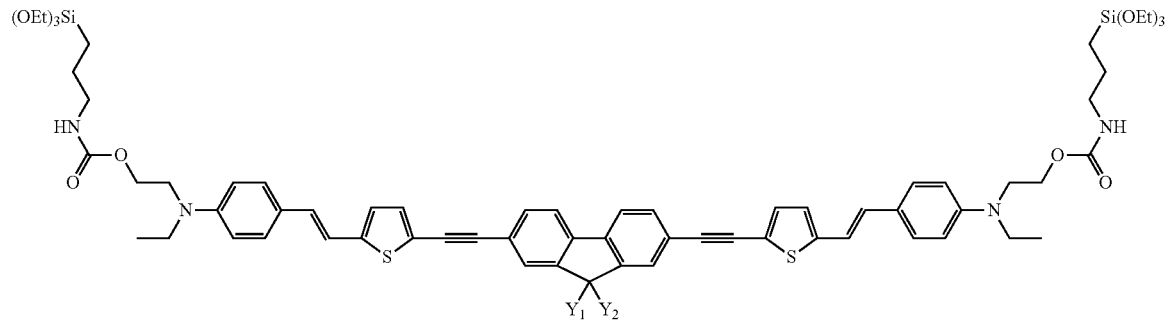
wherein $Y_1$ and $Y_2$ are similar and represent —$(CH_2CH_2)O((CH_2CH_2)O)_2CH_3$ groups.
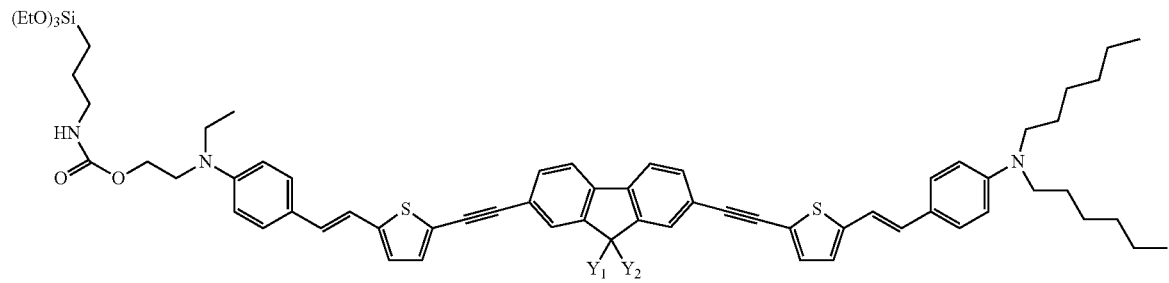
wherein $Y_1$ and $Y_2$ are similar and represent —$(CH_2CH_2)O((CH_2CH_2)O)_2CH_3$ groups.
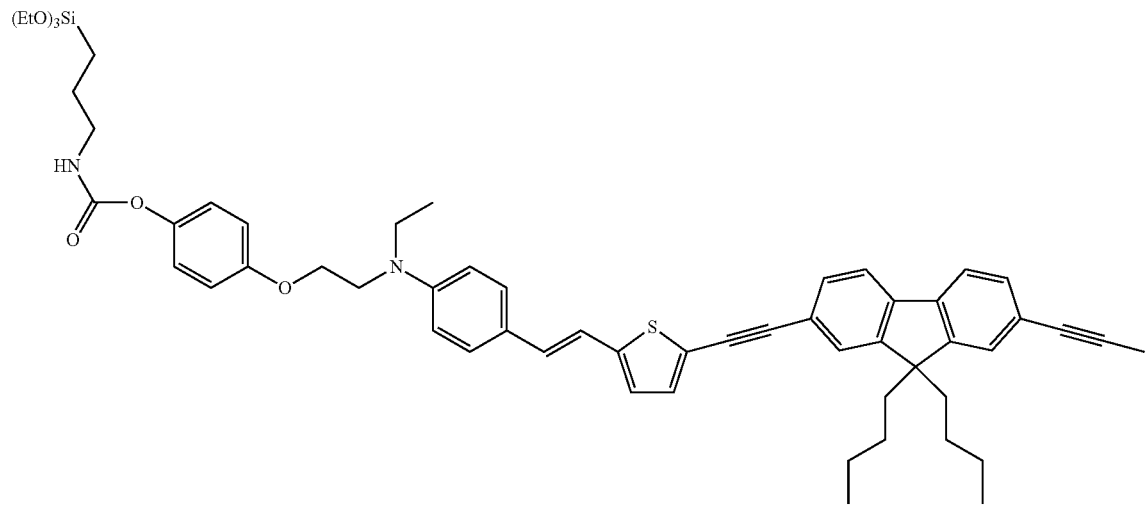

-continued

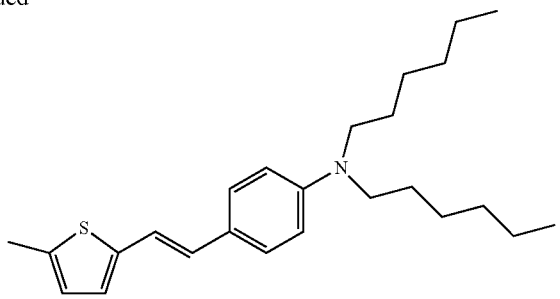

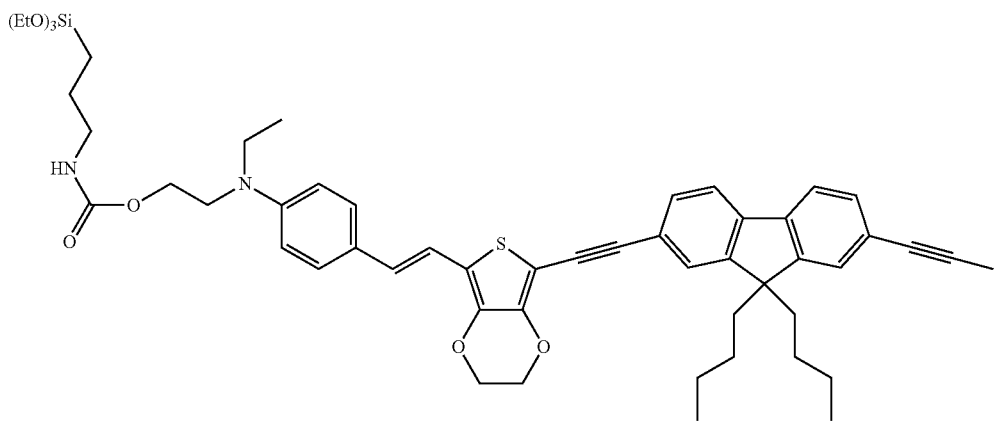

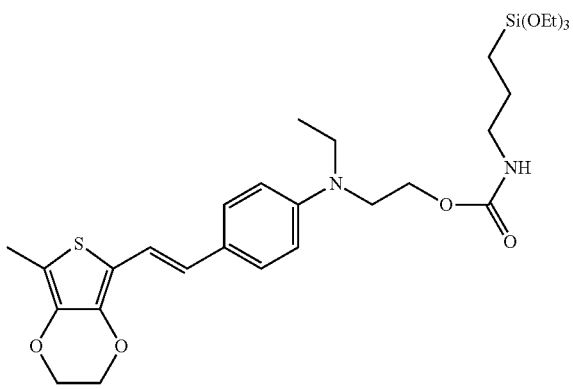

According to an advantageous embodiment, the invention relates to the compounds as defined above, wherein the two-photon absorption cross section is higher than about 300 GM, particularly higher than about 750 GM, for at least one wavelength value ranging from 720 nm to 900 nm.

Two-photon absorption is the simultaneous absorption of two photons of identical frequencies in order to excite a molecule from one state (usually the ground state) to a higher energy electronic state. The energy difference between the involved lower and upper states of the molecule is equal to the sum of the energies of the two photons. Two-photon absorption is of many orders of magnitude weaker than linear absorption and is therefore not an everyday phenomenon. It differs from linear absorption in that the strength of absorption depends on the square of the light intensity, thus it is a nonlinear optical process.

The term "GM" designates two-photon absorption cross section unit. "GM" stands for Goeppert-Mayer, 1 GM is $10^{-50}$ $cm^4$ s $photon^{-1}$.

The two-photon absorption cross section value depends on the wavelength of the excitation photons. Compounds according to formula (I) to (XIV) of the present invention are dedicated to biological application, thus it is important to have compounds showing an important cross section for radiation wavelength commonly used in photodynamic therapy.

For example, the compounds 6a and 6b of formula:

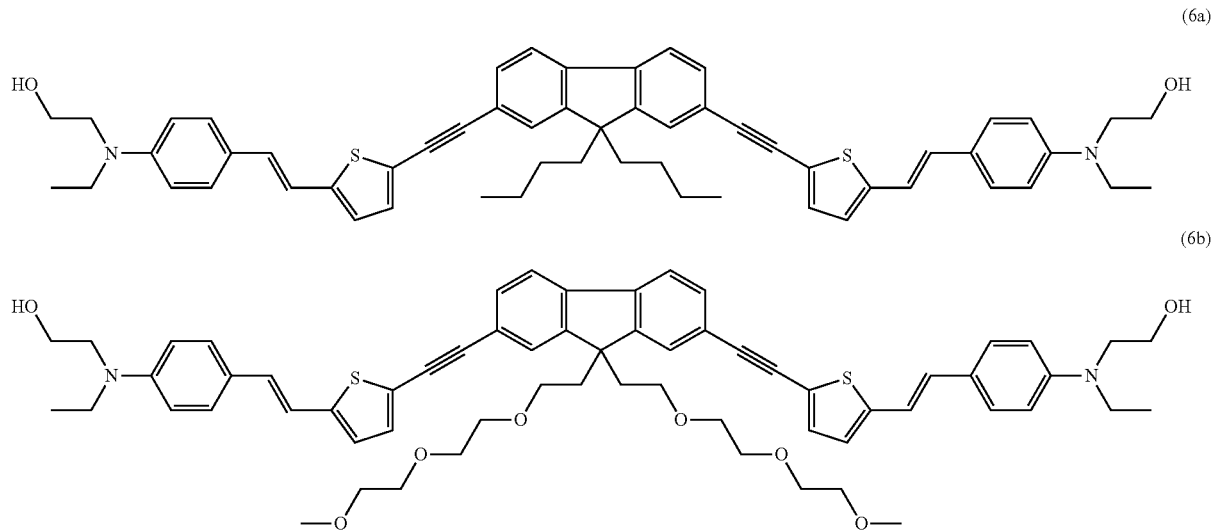

(6a)

(6b)

have two-photon absorption cross section at 720 nm of 1340 GM for 6a, and 1530 GM for 6b.

According to an advantageous embodiment, the invention relates to a compound as defined above, wherein the quantum yield of singlet oxygen generation in toluene is higher than about 3%, particularly higher than about 5%, particularly higher than about 10%.

According to an advantageous embodiment, the invention relates to a compound as defined above, wherein the quantum yield of fluorescence in toluene or in ethanol ranges from about 5% to about 95%, particularly from about 10% to about 90%, particularly from about 20% to about 80%.

Photon absorption increases the energy of the photosensitizer. Dissipation of this excitation energy to restore the ground state can occur through fluorescence, energy transfer or other dissipation process. Fluorescence corresponds to the emission of a photon.

If the fluorescence quantum yield is equal to 100%, the excess energy of every excited molecules is dissipated through the emission of photons.

If the singlet oxygen generation quantum yield is equal to 100%, the excess energy of every excited molecules is dissipated through transfer of said excess energy to triplet oxygen molecules present in the photosensitizer surrounding, and generation of singlet oxygen species.

The photosensitizers according to the present invention have fluorescence and oxygen generation properties. Singlet oxygen generation quantum yield is not equal to 100% or 0%. Fluorescence quantum yield is not equal to 100% or 0%.

According to an advantageous embodiment, the invention relates to a compound as defined above, wherein the quantum yield of fluorescence in toluene or in ethanol ranges from about 5% to about 95% and the quantum yield of singlet oxygen generation in toluene is higher than about 3% particularly the quantum yield of fluorescence in toluene or in ethanol ranges from about 10% to about 90% and the quantum yield of singlet oxygen generation in toluene is higher than about 5%, particularly the quantum yield of fluorescence in toluene or in ethanol ranges from about 20% to about 80% and the quantum yield of singlet oxygen generation in toluene is higher than about 10%.

The invention relates to silica nanoparticle, comprising at least one photosensitizer constituted by at least a compound as defined above, covalently linked to said nanoparticle, and possibly comprising shielding moieties grafted on the surface of said nanoparticle, and possibly comprising biotargeting moieties grafted on the surface of said nanoparticle.

The photosensitizers according to formula (I) to (XIV) of the present invention are covalently linked to the nanoparticles. Covalent bonding prevents leakage of the photosensitizers from the nanoparticles. The photosensitizers are not "trapped" within the silica nanoparticle, but they are a part of the nanoparticle structure. More precisely, they are covalently linked to the walls of the nanoparticle.

The term "shielding moiety" designates a molecule, or a molecule fragment, having monophotonic absorption properties at wavelengths corresponding to the monophotonic absorption wavelengths of the photosensitizer comprised within the silica nanoparticle. The monophotonic absorption wavelengths of the shielding moieties are ranging from 190 to 600 nm, particularly 250 to 500 nm, particularly 250 to 400 nm.

Shielding moieties are covalently linked to the surface of the nanoparticle.

The term "biotargeting moiety" designates a molecule susceptible of interactions with the receptors on the surface of targeted cells. Biotargeting moieties enhance the affinity of the nanoparticle for a certain type of cells, and increase the probability of internalization of the nanoparticle within the cell. Biotargeting moieties can be saccharide residues, phosphorylated or not, peptides or other small organic molecules.

Biotargeting moieties are located on the surface of the nanoparticle since the surface of the nanoparticle interacts with cells membrane receptors.

Biotargeting moieties are linked to the nanoparticle either by direct covalent bonding of the biotargeting moieties to the surface of the silica nanoparticle, or through the shielding moieties. "Biotargeting moieties linked to the silica nanoparticle through the shielding moieties" means that each biotargeting moiety is covalently linked to a shielding moiety, and said shielding moiety is covalently linked to the silica nanoparticle.

According to an advantageous embodiment, the invention relates to silica nanoparticle, comprising
- at least one photosensitizer constituted by at least a compound as defined above, covalently linked to said nanoparticle,
- biotargeting moieties grafted on the surface of said nanoparticle, and
- shielding moieties grafted on the surface of said nanoparticle.

To prevent photosensitizer leakage improves the efficiency of the nanoparticles, and reduces the toxicity risks. When the cells are irradiated, the toxicity is located in the cells containing nanoparticles. Cancer cells can be specifically targeted if the nanoparticles are coated with biotargeting moieties. In the present invention the term "coated with" means "grafted on the surface with".

If the photosensitizer can dissociate from the nanoparticles, photosensitizers will disseminate slowly in the whole organism, not targeting specifically tumours. Moreover, in this case they are irradiated, nanoparticles targeting cancer cells lose a part of their potency.

According to an advantageous embodiment, the invention relates to silica nanoparticle, comprising
- at least one photosensitizer constituted by at least a compound as defined above, covalently linked to said nanoparticle, and
- biotargeting moieties grafted on the surface of said nanoparticle trough shielding moieties.

It is advantageous to link the biotargeting moieties through the shielding moieties since the entities consisting of the biotargeting and shielding moieties can be prepared separately and grafted in one step on the silica nanoparticle.

According to an advantageous embodiment, the invention relates to silica nanoparticle, comprising at least one photosensitizer constituted by at least a compound as defined above, covalently linked to said nanoparticle,
and devoid of
- biotargeting moieties grafted on the surface of said nanoparticle, and devoid of
- shielding moieties grafted on the surface of said nanoparticle.

It is advantageous to graft biotargeting moieties on the surface of the nanoparticle, because it will increase the passive endocytosis of said nanoparticle in tumour cells, and thus increase the sensibility of said tumour cells to phototherapy.

According to an advantageous embodiment, the invention relates to silica nanoparticle, comprising
- at least one photosensitizer constituted by at least a compound as defined above, covalently linked to said nanoparticle,
- shielding moieties grafted on the surface of said nanoparticle,
and devoid of
- biotargeting moieties grafted on the surface of said nanoparticle.

According to an advantageous embodiment, the invention relates to silica nanoparticle, comprising
- at least one photosensitizer constituted by at least a compound as defined above, covalently linked to said nanoparticle,
- biotargeting moieties grafted directly on the surface of said nanoparticle, and devoid of
- shielding moieties grafted on the surface of said nanoparticle.

It is advantageous to graft the surface of the nanoparticle with biotargeting and shielding moieties, because it increases the endocytosis of the nanoparticle in the tumour cells, and it reduces the photosensibility of the patient skin.

Thus, the tumour cells are more sensitive to phototherapy, and the patient skin is less sensitive to light. Said sensitivity of the skin to light is one of the main undesirable side effects of phototherapy.

The invention relates to silica nanoparticle composition, constituted by at least one silica nanoparticle comprising at least one photosensitizer constituted by at least a compound as defined above, covalently linked to said nanoparticle, and possibly comprising shielding moieties grafted on the surface of said nanoparticle, and possibly comprising biotargeting moieties grafted on the surface of said nanoparticle.

The term "silica nanoparticles composition" refers to a combination of several nanoparticles with the same photosensitizers or different photosensitizers. The nanoparticles according to the present invention may contain other elements well known from the man skilled in the art such as stabiliser, preservative, excipient.

According to an advantageous embodiment, the invention relates to silica nanoparticle composition as defined above, wherein said photosensitizer is excited by a biphotonic irradiation, said biphotonic irradiation wavelength value ranges from about 650 nm to 1200 nm, particularly from about 720 nm to 900 nm.

According to an advantageous embodiment, the invention relates to silica nanoparticle composition, comprising
- at least one photosensitizer constituted by at least a compound as defined above, covalently linked to said nanoparticle,
- biotargeting moieties grafted on the surface of said nanoparticle, and
- shielding moieties grafted on the surface of said nanoparticle.

According to an advantageous embodiment, the invention relates to silica nanoparticle composition, comprising
- at least one photosensitizer constituted by at least a compound as defined above, covalently linked to said nanoparticle, and
- biotargeting moieties grafted on the surface of said nanoparticle trough shielding moieties.

According to an advantageous embodiment, the invention relates to silica nanoparticle composition, comprising at least one photosensitizer constituted by at least a compound as defined above, covalently linked to said nanoparticle,
and devoid of
- biotargeting moieties grafted on the surface of said nanoparticle, and devoid of
- shielding moieties grafted on the surface of said nanoparticle.

According to an advantageous embodiment, the invention relates to silica nanoparticle composition, comprising
- at least one photosensitizer constituted by at least a compound as defined above, covalently linked to said nanoparticle,
- shielding moieties grafted on the surface of said nanoparticle,
and devoid of
- biotargeting moieties grafted on the surface of said nanoparticle.

According to an advantageous embodiment, the invention relates to silica nanoparticle composition, comprising
- at least one photosensitizer constituted by at least a compound as defined above, covalently linked to said nanoparticle,
- biotargeting moieties grafted directly on the surface of said nanoparticle, and devoid of
shielding moieties grafted on the surface of said nanoparticle.

According to another embodiment the invention relates to silica nanoparticle composition as defined above, wherein said silica nanoparticle has an organized porosity.

The term "organized porosity" designates a regular, tridimensional, geometrical, distribution of pores.

The organized porosity increases the exchange surface of the particle and facilitates the diffusion of oxygen through the particle.

According to another embodiment the invention relates to silica nanoparticle composition as defined above, wherein said silica nanoparticle is mesoporous.

The term "mesoporous" designates materials with an organized porous structure and with pore size between 2 and 10 nm.

According to an advantageous embodiment, the invention relates to silica nanoparticle composition as defined above, wherein said silica nanoparticle has a pore size ranging from about 0.1 nm to about 10 nm, particularly ranging from about 1 nm to about 5 nm, particularly ranging from about 2 nm to about 2.4 nm The size of the pore in the structure of the nanoparticle is important. Pores larger than nm produce a fragile and unstable structure. Pores smaller than 0.1 nm are too small to allow proper diffusion of molecules though the structure; the structure is not porous anymore.

According to an advantageous embodiment, the invention relates to silica nanoparticle composition as defined above, wherein said silica nanoparticle has a size ranging from about nm to about 300 nm, particularly ranging from about 50 nm to about 150 nm, particularly ranging from about 80 nm to about 100 nm.

The size of the nanoparticle is important. Particles larger than 300 nm are too large to be integrated into cells through endocytosis. Particles smaller than 30 nm are too small to allow the formation of a mesoporous structure.

According to another embodiment the invention relates to silica nanoparticle composition as defined above, comprising biotargeting moieties grafted on the surface of said nanoparticle which specifically target neoplastic tissues.

The term "neoplastic tissues" designates an abnormal mass of tissue as a result of an abnormal proliferation of cells. The growth of this clone of cells exceeds, and is uncoordinated with, that of the normal tissues around it. This abnormal mass of tissue may be benign, pre-malignant or malignant.

According to an advantageous embodiment, the invention relates to silica nanoparticle composition as defined above, wherein biotargeting moieties grafted on the surface of said nanoparticle are sugar derivatives, particularly mannose derivatives.

The term "sugar derivatives" designates saccharides such as glucose, galactose, mannose, sugar analogs such as their deoxy derivatives, for example fucose, rhamnose, their acetylated derivatives such as N-acetylglucosamine, N-acetylgalactosamine, their phosphorylated derivatives such as glucose-6-phosphate or mannose-6-phosphate, or sialyl groups.

Biotargeting moieties correspond to specific receptors which are over expressed by cancer cells or on the surface of said cancer cells. The presence of biotargeting moieties on the surface of the silica nanoparticles increases the affinity of the nanoparticles toward cancer cells According to another embodiment the invention relates to silica nanoparticle composition as defined above, comprising shielding moieties grafted on the surface of said nanoparticle, and which specifically absorb radiations in the 190 to 600 nm, particularly 250 to 500 nm, particularly 250 to 400 nm wavelengths.

According to another embodiment the invention relates to silica nanoparticle composition as defined above, comprising shielding moieties grafted on the surface of said nanoparticle, said shielding moieties concentration ranges from 0.01 mmol/g to 1 mmol/g, particularly 0.05 mmol/g to 0.5 mmol/g, particularly 0.1 mmol/g to 0.3 mmol/g, said nanoparticle being devoid of biotargeting moieties, The concentration of shielding moieties should not be below 0.01 mmol/g, because the shielding effect would be too low and the skin of the patient would be sensitive to natural light. The concentration of shielding moieties can not be over 1 mmol/g, because the amount of shielding moieties that can be grafted on the surface of the particle is limited by the surface of said particle.

According to another embodiment the invention relates to silica nanoparticle composition as defined above,
comprising shielding moieties grafted on the surface of said nanoparticle, said shielding moieties concentration ranges from 1 µmol per gram to about 2 mmol per gram, particularly ranges from about 0.01 mmol per gram to about 1 mmol per gram, particularly ranges from about 0.1 mmol per gram to about 0.4 mmol per gram comprising biotargeting moieties directly grafted on the surface of said nanoparticle.

According to another embodiment the invention relates to silica nanoparticle composition as defined above,
comprising shielding moieties grafted on the surface of said nanoparticle, said shielding moieties with concentrations ranging from about 1 µmol per gram to about 2 mmol per gram, particularly ranges from about 0.01 mmol per gram to about 1 mmol per gram, particularly ranges from about 0.1 mmol per gram to about 0.4 mmol per gram
comprising biotargeting moieties grafted on the surface of said nanoparticle through said shielding moieties.

According to an advantageous embodiment, the invention relates to silica nanoparticle composition as defined above, wherein said shielding moieties are phenylaminocyclobutenedione moieties.

According to an advantageous embodiment, the invention relates to silica nanoparticle composition as defined above, wherein said shielding moieties are phenylaminocyclobutenedione moieties, and wherein said biotargeting moieties are grafted on the nanoparticle trough phenylaminocyclobutenedione moieties.

According to another embodiment the invention relates to silica nanoparticle composition as defined above, wherein the concentration of said photosensitizer as defined above, with respect to the total mass of the nanoparticle comprising said photosensitizer, ranges from about 0.1 micromole per gram to about 100 micromoles per gram, particularly ranges from about 0.5 micromoles per gram to about 30 micromoles per gram, particularly ranges from about 1 micromoles per gram to about 10 micromoles per gram.

Photosensitizer concentration higher than 100 µmol/g is not desirable because it would impair the formation and the stability of the nanoparticle. Photosensitizer concentration below 0.1 µmol is not desirable because the amount of photosensitizers contained within the nanoparticle would be too small to have any significant effect in phototherapy.

According to another embodiment the invention relates to silica nanoparticle composition as defined above, wherein the concentration of the biotargeting moieties grafted on the surface of the said nanoparticle, ranges from about 1 µmol per gram to about 2 mmol per gram, particularly ranges from about 0.01 mmol per gram to about 1 mmol per gram, particularly ranges from about 0.1 mmol per gram to about 0.4 mmol per gram.

The concentration of the biotargeting moieties grafted on the surface of the nanoparticle should not be below 1 µmol per gram, or over 1 mmol per gram, because it would impair the biomolecular targeting effect.

According to an advantageous embodiment, the invention relates to silica nanoparticle composition as defined above, wherein the concentration of the photosensitizer, as defined above, covalently linked to the nanoparticle, ranges from 1 µmol/g to about 10 µmol/g,
said silica nanoparticle is mesoporous and has a diameter ranging from 80 nm to about 100 nm, and is devoid of
biotargeting moieties, and devoid of
shielding moieties.

According to an advantageous embodiment, the invention relates to silica nanoparticle composition as defined above, wherein the concentration of the photosensitizer, as defined above, covalently linked to the nanoparticle, ranges from about 0.1 micromol per gram to about 50 micromol per gram,
said silica nanoparticle being mesoporous and having a diameter ranging from about nm to about 300 nm,
comprising biotargeting moieties grafted on the surface of said nanoparticle, said biotargeting moieties being in a concentration ranging from about 1 micromol per gram to about 2 mmol per gram, and the said biotargeting moieties being derivatives from mannose, and
said nanoparticle being devoid of shielding moieties.

According to an advantageous embodiment, the invention relates to silica nanoparticle composition as defined above, wherein the concentration of the photosensitizer, as defined above, covalently linked to the nanoparticle, ranges from about 0.1 micromol per gram to about 50 micromol per gram,
said silica nanoparticle being mesoporous and having a diameter ranging from about nm to about 300 nm, and
said nanoparticle being devoid of biotargeting moieties, and
said nanoparticle comprising shielding moieties grafted on its surface, said shielding moieties being phenylaminocyclobutenedione moieties.

According to an advantageous embodiment, the invention relates to silica nanoparticle composition as defined above, wherein the concentration of the photosensitizer, as defined above, covalently linked to the nanoparticle, ranges from about 0.1 micromol per gram to about 50 micromol per gram,
said silica nanoparticle being mesoporous and having a diameter ranging from about nm to about 300 nm,
said silica nanoparticle comprising
biotargeting moieties on the surface, at a concentration ranging from about 1 micromol per gram to about 2 mmol per gram, said biotargeting moieties being derivatives of mannose, and
shielding moieties which are phenylaminocyclobutenedione moieties.

According to an advantageous embodiment, the invention relates to silica nanoparticle composition as defined above, wherein the concentration of the photosensitizer, as defined above, covalently linked to the nanoparticle, ranges from about 0.1 micromol per gram to about 50 micromol per gram,
said silica nanoparticle being mesoporous and having a diameter ranging from about nm to about 300 nm,
said nanoparticle comprising
shielding moieties grafted on its surface, said shielding moieties being phenylaminocyclobutenedione moieties, and
biotargeting moieties which are grafted on the surface of said nanoparticle through said phenylaminocyclobutenedione moieties, said biotargeting moieties being in a concentration ranging from about 1 micromol per gram to about 2 mmol per gram, said biotargeting moieties being derivatives from mannose.

The invention relates to pharmaceutical composition comprising
at least one of the compounds as defined above, or
at least one silica nanoparticle composition as defined above, and
a pharmaceutically acceptable carrier.

The invention relates to pharmaceutical composition comprising
at least one of the compounds as defined above, or
at least one silica nanoparticle composition as defined above, and
at least one antineoplastic agent, and
a pharmaceutically acceptable carrier.

The term "antineoplastic agent" designates chemical compounds which inhibits or slow down the growth or proliferation of tumour cells, or compounds that induce apoptosis of tumour cells. Antineoplastic agents are selected among:
alkylating agents such as cisplatin, carboplatin, oxaliplatin, mechlorethylamine, cyclophosphamide, chorambucil, or ifosfamide,
anti-metabolites, such as azathioprine, mercaptopurine, or pyrimidine,
plant alkaloids, such as vinca alkaloids (vincristine, vinblastine, vinorelbine, vindesine), taxanes (taxol, docetaxel), or podophyllotoxin (etoposide, teniposide)
topoisomerase inhibitors, such as camptothecine, irinotecan, topotecan, amsacrine, etoposide, etoposide phosphate, tenposide, or epipodophyllotoxins,
antitumour antibiotics, such as dactinomycin, doxorubicin, epirubicin, or bleomycin.

The invention relates to pharmaceutical composition as defined above comprising
at least one silica nanoparticle composition as defined above, and
at least one antineoplastic agent, and
a pharmaceutically acceptable carrier.

It is possible to enclose antineoplastic agents within the pores of the nanoparticles of the present invention. The composition thus obtained combines the advantages of the present invention, namely the efficiency and precision of the biphotonic phototherapy, the selective biotargeting of the tumour cells, and the protection of the patient skin through shielding of the nanoparticles, with the classical antineoplastic agent effect.

The water solubility of the antineoplastic agent is increased when the antineoplastic agent is entrapped within the nanoparticle pores.

Entrapping of anticancer drugs in nanoparticles has already been described in the art: Lu J, Liong M, Zink J I, Tamanoi F. Mesoporous silica nanoparticles as a delivery system for hydrophobic anticancer drugs. Small 2007; 3 (8): 1341-6.

The invention relates to pharmaceutical composition as defined above, comprising
at least one silica nanoparticle composition as defined above, and
at least one antineoplastic agent, and
a pharmaceutically acceptable carrier,
wherein said silica nanoparticle, comprises at least one photosensitizer constituted by at least a compound as defined above, covalently linked to said nanoparticle, and possibly comprising shielding moieties grafted on the surface of said nanoparticle, and possibly comprising biotargeting moieties grafted on the surface of said nanoparticle.

The invention relates to pharmaceutical composition as defined above, comprising
- at least one silica nanoparticle composition as defined above, and
- at least one antineoplastic agent, and
- a pharmaceutically acceptable carrier, said silica nanoparticle, having a concentration of the photosensitizer, as defined above, covalently linked to the nanoparticle, ranging from about 0.1 micromol per gram to about 50 micromol per gram, said silica nanoparticle being mesoporous and having a diameter ranging from about nm to about 300 nm,
said nanoparticle comprising
  shielding moieties grafted on its surface, said shielding moieties being phenylaminocyclobutenedione moieties, and
  biotargeting moieties which are grafted on the surface of said nanoparticle through said phenylaminocyclobutenedione moieties, said biotargeting moieties being in a concentration ranging from about 1 micromol per gram to about 2 mmol per gram, said biotargeting moieties being derivatives from mannose.

The invention relates to pharmaceutical composition as defined above, comprising
- at least one silica nanoparticle composition as defined above, and
- at least one antineoplastic agent, and
- a pharmaceutically acceptable carrier,
wherein said silica nanoparticle comprises at least a compound 6a or 6b according to the formula:

at least one of the compounds as defined above, or
at least one silica nanoparticle composition as defined above, and
a pharmaceutically acceptable carrier.

said silica nanoparticle, having a concentration of the photosensitizer, as defined above, covalently linked to the nanoparticle, ranging from about 0.1 micromol per gram to about 50 micromol per gram, said silica nanoparticle being mesoporous and having a diameter ranging from about 30 nm to about 300 nm,
said nanoparticle comprising
  shielding moieties grafted on its surface, said shielding moieties being phenylaminocyclobutenedione moieties, and
  biotargeting moieties which are grafted on the surface of said nanoparticle through said phenylaminocyclobutenedione moieties, said biotargeting moieties being in a concentration ranging from about 1 micromol per gram to about 2 mmol per gram, said biotargeting moieties being derivatives from mannose.

According to an advantageous embodiment, the invention relates to pharmaceutical composition as defined above, comprising
  about 0.001 μmol/mL to about 0.1 μmol/mL, particularly about 0.002 μmol to about 0.05 μmol, particularly about 0.0025 μmol to about 0.001 μmol, of at least one of the compounds as defined above, or
  about 0.05 μg/mL to about 0.05 mg/mL, particularly about 0.5 μg/mL to about 100 μg/mL, particularly about 5 μg/mL to about 40 μg/mL, of at least one of the nanoparticle as defined above,
and
a pharmaceutically acceptable carrier.

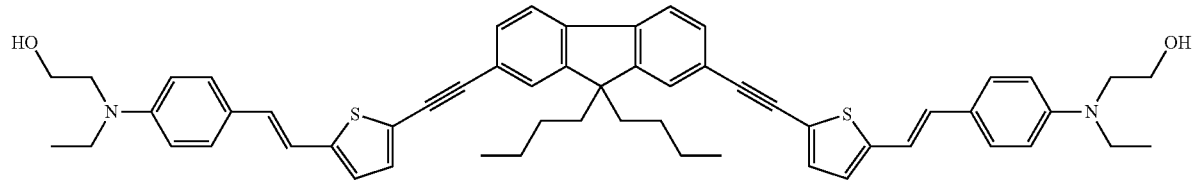

(6a)

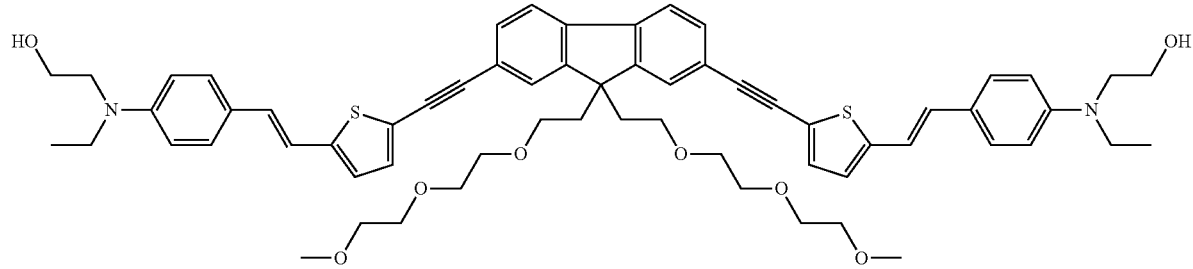

(6b)

The invention relates to pharmaceutical composition as defined above, comprising
- at least one silica nanoparticle composition as defined above, and
- at least one antineoplastic agent, and
- a pharmaceutically acceptable carrier,
wherein said antineoplastic agent is selected among campthotecine, Paclitaxel or doxorubicin.

According to another embodiment the invention relates to pharmaceutical composition as defined above, comprising According to an advantageous embodiment, the invention relates to pharmaceutical composition as defined above, comprising at least one silica nanoparticle composition as defined above, and a pharmaceutically acceptable carrier, wherein said nanoparticle is devoid of biotargeting moieties and devoid of shielding moieties.

According to an advantageous embodiment, the invention relates to pharmaceutical composition as defined above, comprising at least one of the silica nanoparticle composition as defined above, and a pharmaceutically acceptable carrier, wherein said nanoparticle comprising biotargeting moieties grafted on its surface, and said nanoparticle being devoid of shielding moieties.

According to an advantageous embodiment, the invention relates to pharmaceutical composition as defined above, comprising at least one of the silica nanoparticle composition as defined above, and a pharmaceutically acceptable carrier, wherein the said nanoparticle comprises:
biotargeting moieties directly grafted on its surface, and shielding moieties grafted on its surface.

According to an advantageous embodiment, the invention relates to pharmaceutical composition as defined above, comprising at least one of the nanoparticle composition as defined above, and a pharmaceutically acceptable carrier, wherein said nanoparticle comprises:
shielding moieties grafted on its surface, and
biotargeting moieties grafted on its surface trough said shielding moieties.

Physiological serum or any other carrier acceptable for intravenous injection may be an acceptable pharmaceutical carrier according to the present invention. The pharmaceutical composition may be administrated to a patient by injection, by oral administration, by sub lingual administration, by vaporisation onto the mucosa, or through the skin with a patch. The amount of pharmaceutical composition administered may vary from 1 mg/kg (mg of composition per kg of patient body mass) to 1 g/kg, particularly from 10 mg/kg to 100 mg/kg, particularly from 20 mg/kg to 50 mg/kg.

Between 2 and 24 hours after administration the tumour is irradiated. Administration of the said pharmaceutical composition may be repeated one or several times according to the regression of the tumour.

The invention relates to the use of at least one compound as defined above, provided none of the groups $Z_1$, $Z_2$, $Z_3$, and $Z_4$ can represent a group V used as a molecular clip,
for the preparation of a compound as defined above wherein at least of the group $Z_1$, $Z_2$, $Z_3$, and $Z_4$ represents a group V used as a molecular clip.

The invention relates to the use of at least one compound according to formula (I):

phate, $NTf_2$, $PF_6$ anions, p varies from 1 to 6, and R is an alkyl chain linear or branched, from 1 to 9 carbon atoms,
the groups $Z_1$, $Z_2$, $Z_3$, and $Z_4$ represent independently from each other:
a hydrogen atom, or
a chemically reactive group W, such as OH, $NH_2$, SH,
an aryl, aryloxy, aralkyl, aralkyloxy, heteroaryl, heteroaryloxy group, ranging from 1 to 10 carbon atoms, containing a chemically reactive group W as above defined, or
an alkyl chain possibly unsaturated, linear, branched or substituted, ranging from 1 to carbon atoms, or
an alkyl chain possibly unsaturated, linear, branched or substituted, ranging from 1 to 10 carbon atoms, and containing a chemically reactive group W as above defined, or
a polyethylene glycol chain of formula $-(CH_2)_q-O-(CH_2CH_2O)_r-CH_2CH_2-W$, wherein q<4 and r varies from 1 to 6, and W is a chemically reactive group as above defined,
provided at least one of the $Z_1$, $Z_2$, $Z_3$ or $Z_4$ groups represents:
a chemically reactive group W, such as OH, $NH_2$, SH, or
an aryl, aryloxy, aralkyl, aralkyloxy, heteroaryl, heteroaryloxy group, ranging from 1 to 10 carbon atoms, containing a chemically reactive group W as above defined, or
an alkyl chain possibly unsaturated, linear, branched or substituted, ranging from 1 to
10 carbon atoms, and containing a chemically reactive group W as above defined, or
a polyethylene glycol chain of formula $-(CH_2)_q-O-(CH_2CH_2O)_rCH_2CH_2-W$, wherein q<4 and r varies from 1 to 6, and W is a chemically reactive group as above defined,
the groups $Z_5$ and $Z_6$ represent independently from each other:
a hydrogen atom, or
an alkyl chain possibly unsaturated, linear, branched or substituted, ranging from 1 to 9 carbon atoms, or
an alkoxy group, a carbocyclic group, a heterocyclic group, an aromatic group, ranging from 1 to 9 carbon atoms, or

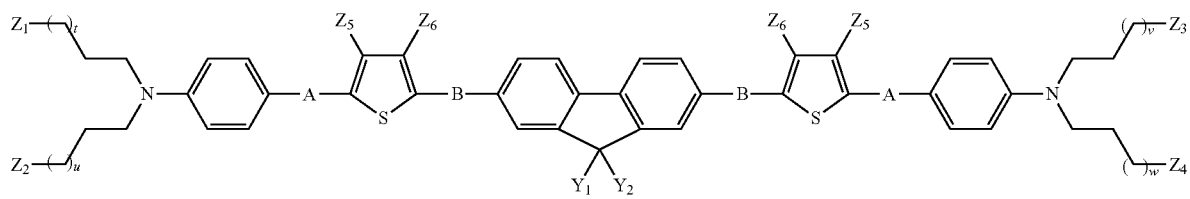

(I)

wherein
the groups A and B represent independently from each other $-CH=CH-$, or $-C\equiv C-$,
the terms t, u, v, w represent, independently from each other, values ranging from 0 to 9,
the groups $Y_1$ and $Y_2$ represent independently from each other:
a hydrogen atom, or
an alkyl group (linear, branched or substituted) carrying from 1 to 9 carbon atoms, or
a polyethylene glycol chain of formula: $-(CH_2)_n-O-(CH_2CH_2O)_mCH_3$, wherein n<4 and m varies from 1 to 6, or
an ammonium group of formula: $-(CH_2)_p-NR_3^+X^-$, wherein $X^-$ is selected among halogens, sulphate, phos- $Z_5$ and $Z_6$ are linked together through an ethylene glycol group, thus providing a 3,4-ethylenedioxythiophene group (EDOT) with the thiophene group they are linked to,

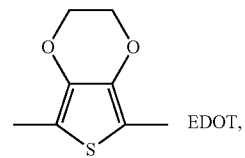

EDOT, for the synthesis of a compound according to formula (I) wherein at least one of the $Z_1$, $Z_2$, $Z_3$ or $Z_4$ groups represents a group V used as a molecular clip constituted by -α-β-δ, wherein:
- α is a functional linking group such as a carbamate, an urea, a thiocarbamate, an amide, and
- β is an alkyl chain, linear or branched, containing from 1 to 9 carbon atoms, and
- δ is a Si(OR')$_3$ group, wherein R' is an alkyl chain, linear or branched, from 1 to 9 carbon atoms.

Preferably X$^-$ is selected among anions that do not quench totally the fluorescence of the compound of formula (I). Total quenching of the fluorescence is achieved when the fluorescence quantum yield is reduced below 5%, particularly 2%, particularly 1%, particularly 0.1%. and is particularly of 0%.

According to an advantageous embodiment, the invention relates to the use of the compound having the following formula:

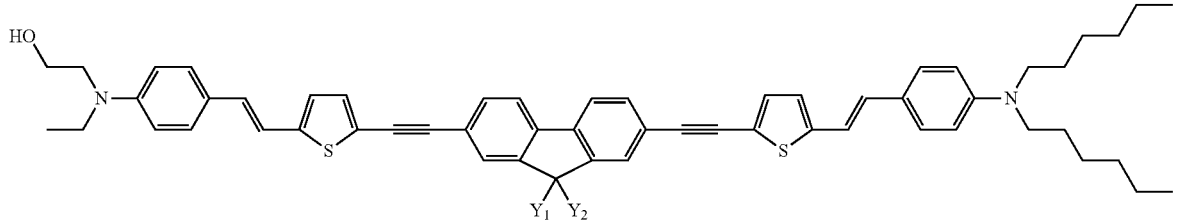

wherein $Y_1$ and $Y_2$ are similar and represent n-butyl alkyl chain, or
—(CH$_2$CH$_2$)O(CH$_2$CH$_2$)O(CH$_2$CH$_2$)OCH$_3$    groups,

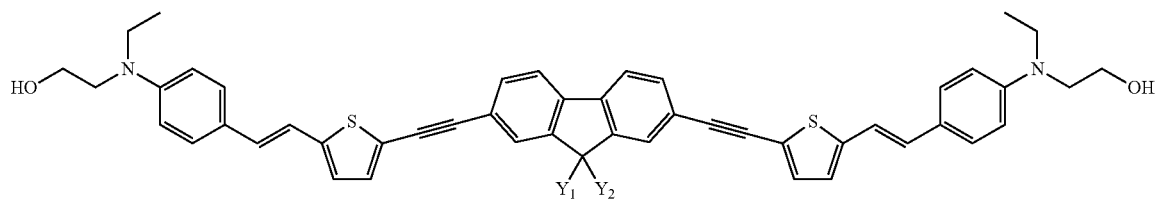

wherein $Y_1$ and $Y_2$ are similar and represent n-butyl alkyl chain, or
—(CH$_2$CH$_2$)O(CH$_2$CH$_2$)O(CH$_2$CH$_2$)OCH$_3$    groups,

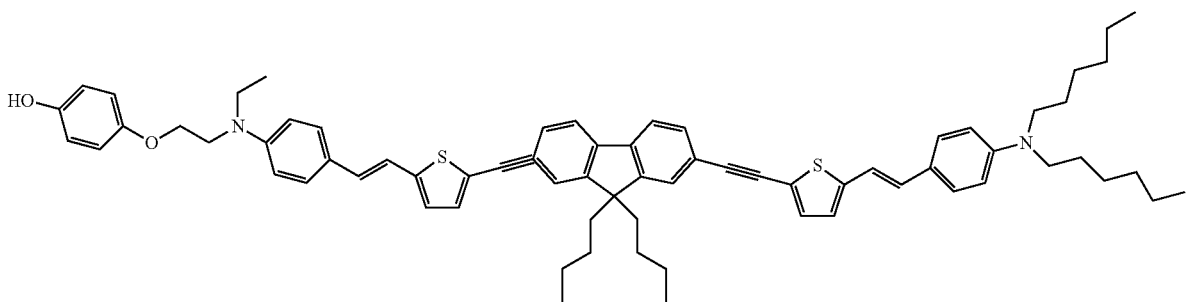

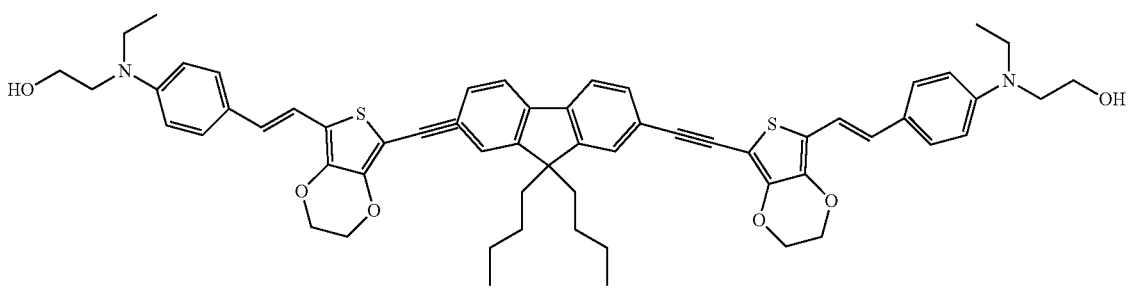

for the synthesis of a compound according to formula (I) wherein at least one of the $Z_1$, $Z_2$, $Z_3$ or $Z_4$ groups represents a group V used as a molecular clip constituted by -α-β-δ, wherein:
- α is a functional linking group such as a carbamate, an urea, a thiocarbamate, an amide, and
- β is an alkyl chain, linear or branched, containing from 1 to 9 carbon atoms, and
- δ is a $Si(OR')_3$ group, wherein R' is an alkyl chain, linear or branched, from 1 to 9 carbon atoms.

The invention relates to the use of at least one compound according to formula (I):

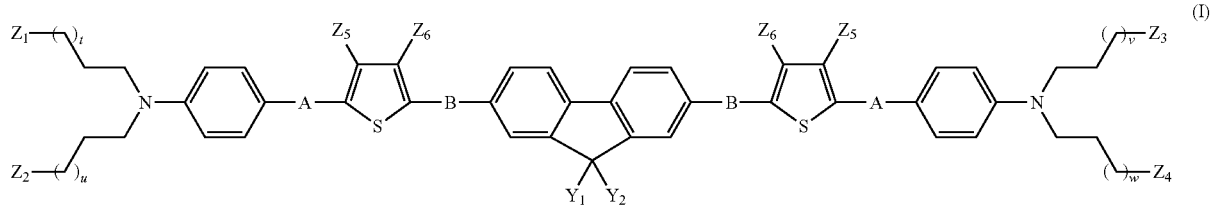

wherein
the groups A and B represent independently from each other
—CH=CH—, or —C≡C—,
the terms t, u, v, w represent, independently from each other, values ranging from 0 to 9,
the groups $Y_1$ and $Y_2$ represent independently from each other:
- a hydrogen atom, or
- an alkyl group (linear, branched or substituted) carrying from 1 to 9 carbon atoms, or
- a polyethylene glycol chain of formula: —$(CH_2)_n$—O—$(CH_2CH_2O)_m CH_3$, wherein n<4 and m varies from 1 to 6, or
- an ammonium group of formula: —$(CH_2)_p$—$NR_3^+X^-$, wherein $X^-$ is selected among halogens, sulphate, phosphate, $NTf_2$, $PF_6$ anions, p varies from 1 to 6, and R is an alkyl chain linear or branched, from 1 to 9 carbon atoms, the groups $Z_1$, $Z_2$, $Z_3$, and $Z_4$ represent independently from each other:
- a hydrogen atom, or
- a chemically reactive group W, such as OH, $NH_2$, SH,
- an aryl, aryloxy, aralkyl, aralkyloxy, heteroaryl, heteroaryloxy group, ranging from 1 to 10 carbon atoms, containing a chemically reactive group W as above defined, or
- an alkyl chain possibly unsaturated, linear, branched or substituted, ranging from 1 to carbon atoms, or
- an alkyl chain possibly unsaturated, linear, branched or substituted, ranging from 1 to carbon atoms, and containing a chemically reactive group W as above defined, or
- a polyethylene glycol chain of formula —$(CH_2)_q$—O—$(CH_2CH_2O)_r$—$CH_2CH_2$—W, wherein q<4 and r varies from 1 to 6, and W is a chemically reactive group as above defined, provided at least one of the $Z_1$, $Z_2$, $Z_3$ or $Z_4$ groups represents:
- a chemically reactive group W, such as OH, $NH_2$, SH, or
- an aryl, aryloxy, aralkyl, aralkyloxy, heteroaryl, heteroaryloxy group, ranging from 1 to 10 carbon atoms, containing a chemically reactive group W as above defined, or
- an alkyl chain possibly unsaturated, linear, branched or substituted, ranging from 1 to 10 carbon atoms, and containing a chemically reactive group W as above defined, or
- a polyethylene glycol chain of formula —$(CH_2)_q$—O—$(CH_2CH_2O)_r$—$CH_2CH_2$—W, wherein q<4 and r varies from 1 to 6, and W is a chemically reactive group as above defined, the groups $Z_5$ and $Z_6$ represent independently from each other:
- a hydrogen atom, or
- an alkyl chain possibly unsaturated, linear, branched or substituted, ranging from 1 to 9 carbon atoms, or
- an alkoxy group, a carbocyclic group, a heterocyclic group, an aromatic group, ranging from 1 to 9 carbon atoms, or
- $Z_5$ and $Z_6$ are linked together through an ethylene glycol group, thus providing a 3,4-ethylenedioxythiophene group (EDOT) with the thiophene group they are linked to,

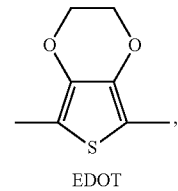

EDOT for the preparation of a silica nanoparticle composition constituted by at least one silica nanoparticle comprising at least one compound used as a photosensitizer according to formula (I)
wherein at least one of the $Z_1$, $Z_2$, $Z_3$ or $Z_4$ groups represents a group V used as a molecular clip constituted by -α-β-δ, wherein:
- α is a functional linking group such as a carbamate, an urea, a thiocarbamate, an amide, and
- β is an alkyl chain, linear or branched, containing from 1 to 9 carbon atoms, and
- δ is a $Si(OR')_3$ group, wherein R' is an alkyl chain, linear or branched, from 1 to 9 carbon atoms.

Preferably $X^-$ is selected among anions that do not quench totally the fluorescence of the compound of formula (I). Total quenching of the fluorescence is achieved when the fluorescence quantum yield is reduced below 5%, particularly 2%, particularly 1%, particularly 0.1%. and is particularly of 0%.

According to an advantageous embodiment, the invention relates to the use of at least one compound having the following formula:

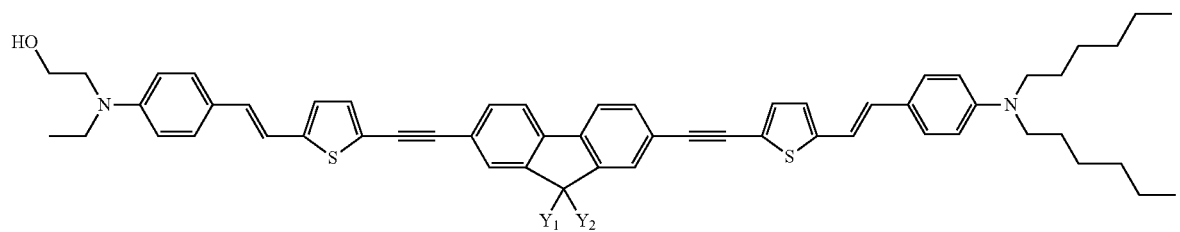

wherein $Y_1$ and $Y_2$ are similar and represent
n-butyl alkyl chain, or
—$(CH_2CH_2)O(CH_2CH_2)O(CH_2CH_2)OCH_3$ groups,

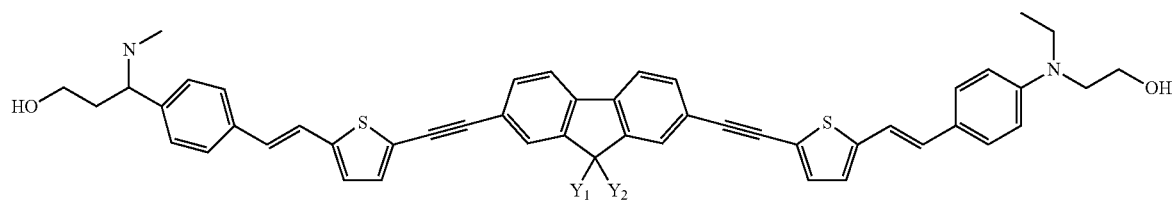

wherein $Y_1$ and $Y_2$ are similar and represent
n-butyl alkyl chain, or
—$(CH_2CH_2)O(CH_2CH_2)O(CH_2CH_2)OCH_3$ groups,

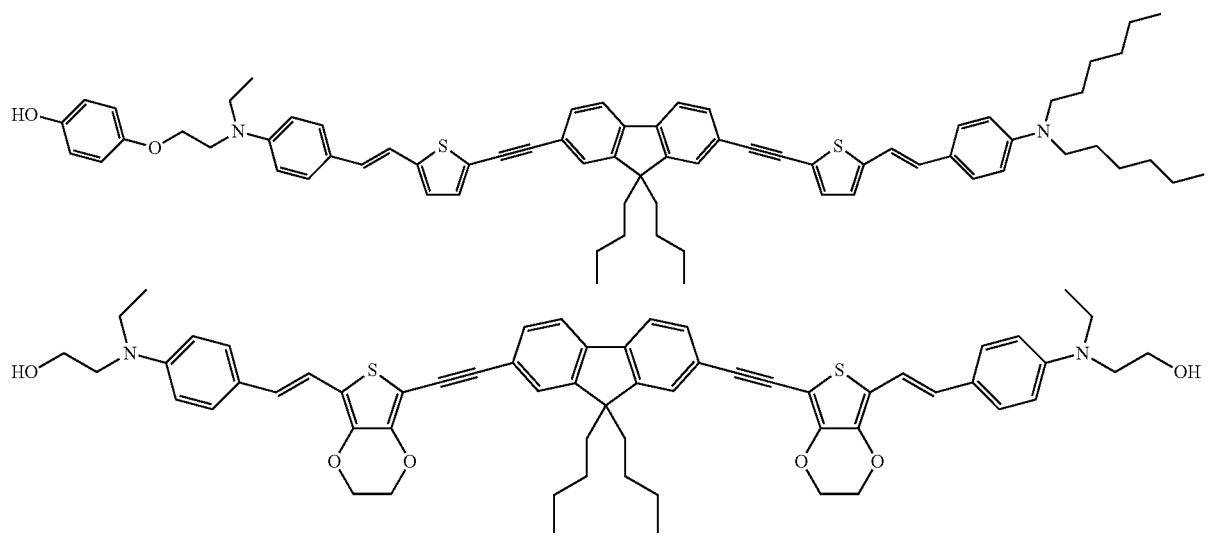

for the preparation of a nanoparticle as defined above.

According to another embodiment the invention relates to the use of at least one compound as defined above, provided none of the groups $Z_1$, $Z_2$, $Z_3$, and $Z_4$ can represent a chemically reactive group W, for the preparation of a nanoparticle as defined above.

According to an advantageous embodiment, the invention relates to the use of at least one compound having the following formula:

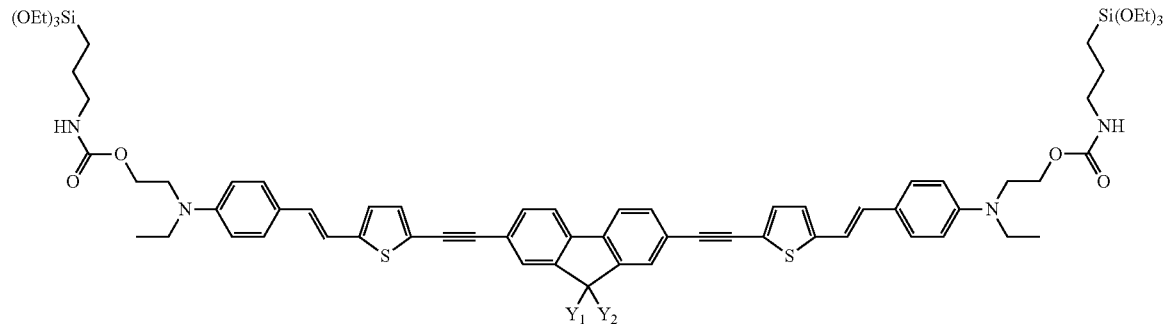

wherein $Y_1$ and $Y_2$ are similar and represent a —$(CH_2CH_2)$ $O((CH_2CH_2)O)_2CH_3$ groups.

for the preparation of a silica nanoparticle composition as defined above.

The invention relates to the use of at least one compound as defined above, or one silica nanoparticle composition as defined above, for the preparation of a medicament for the treatment of cancer.

According to another embodiment the invention relates to the use of at least one compound of formula (I):

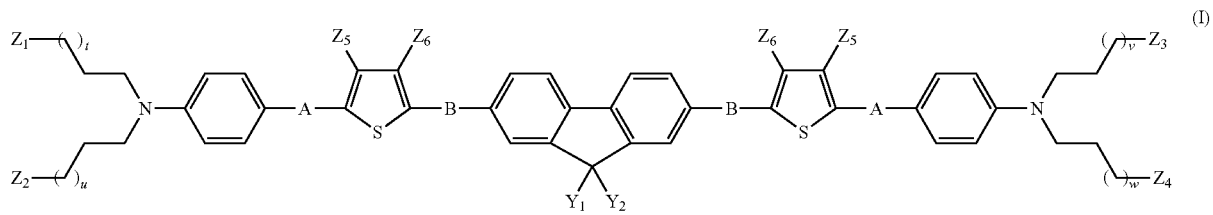

wherein
the groups A and B represent independently from each other —CH=CH—, or —C≡C—,
the terms t, u, v, w represent, independently from each other, values ranging from 0 to 9,
the groups $Y_1$ and $Y_2$ represent independently from each other:
- a hydrogen atom, or
- an alkyl group (linear, branched or substituted) carrying from 1 to 9 carbon atoms, or
- a polyethylene glycol chain of formula: —$(CH_2)_n$—O—$(CH_2CH_2O)_m CH_3$, wherein n<4 and m varies from 1 to 6, or
- an ammonium group of formula: —$(CH_2)_p$—$NR_3^+ X^-$, wherein $X^-$ is selected among halogens, tosylate, sulphate, phosphate, $NTf_2$, $PF_6$ anions, p varies from 1 to 6, and R is an alkyl chain linear or branched, from 1 to 9 carbon atoms, the groups $Z_1$, $Z_2$, $Z_3$, and $Z_4$ represent independently from each other:
- a hydrogen atom, or
- a chemically reactive group W, such as OH, $NH_2$, SH,
- a group V used as a molecular clip constituted by —α-β-δ, wherein:
  α is a functional linking group such as a carbamate, an urea, a thiocarbamate, an amide, and
  β is an alkyl chain, linear or branched, containing from 1 to 9 carbon atoms, and
  δ is a $Si(OR')_3$ group, wherein R' is an alkyl chain, linear or branched, from 1 to 9 carbon atoms,
  or
- an aryl, aryloxy, aralkyl, aralkyloxy, heteroaryl, heteroaryloxy group, ranging from 1 to 10 carbon atoms, containing a chemically reactive group W as above defined, or
- an alkyl chain possibly unsaturated, linear, branched or substituted, ranging from 1 to carbon atoms, or
- an alkyl chain possibly unsaturated, linear, branched or substituted, ranging from 1 to carbon atoms, and containing a chemically reactive group W as above defined, or
- a polyethylene glycol chain of formula —$(CH_2)_q$—O—$(CH_2CH_2O)_r$—$CH_2CH_2$—W, wherein q<4 and r varies from 1 to 6, and W is a chemically reactive group as above defined, provided at least one of the $Z_1$, $Z_2$, $Z_3$ or $Z_4$ groups represents:
- a chemically reactive group W, such as OH, $NH_2$, SH, or
- a group V used as a molecular clip constituted by -α-β-δ, wherein:
  α is a functional linking group such as a carbamate, an urea, a thiocarbamate, an amide, and
  β is an alkyl chain, linear or branched, containing from 1 to 9 carbon atoms, and
  δ is a $Si(OR')_3$ group, wherein R' is an alkyl chain, linear or branched, from 1 to 9 carbon atoms,
  or
- an aryl, aryloxy, aralkyl, aralkyloxy, heteroaryl, heteroaryloxy group, ranging from 1 to 10 carbon atoms, containing a chemically reactive group W as above defined, or
- an alkyl chain possibly unsaturated, linear, branched or substituted, ranging from 1 to carbon atoms, and containing a chemically reactive group W as above defined, or a polyethylene glycol chain of formula —(CH$_2$)$_q$—O—(CH$_2$CH$_2$O)$_r$CH$_2$CH$_2$—W, wherein q<4 and r varies from 1 to 6, and W is a chemically reactive group as above defined, the groups Z$_5$ and Z$_6$ represent independently from each other:
- a hydrogen atom, or
- an alkyl chain possibly unsaturated, linear, branched or substituted, ranging from 1 to 9 carbon atoms, or
- an alkoxy group, a carbocyclic group, a heterocyclic group, an aromatic group, ranging from 1 to 9 carbon atoms, or
- Z$_5$ and Z$_6$ are linked together through an ethylene glycol group, thus providing a 3,4-ethylenedioxythiophene group (EDOT) with the thiophene group they are linked to,

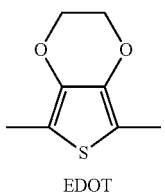

EDOT or
at least one silica nanoparticle comprising at least one of said compound of formula (I),
for the implementation of a probe enabling the imaging of cancer cells.

Preferably X$^-$ is selected among anions that do not quench totally the fluorescence of the compound of formula (I). Total quenching of the fluorescence is achieved when the fluorescence quantum yield is reduced below 5%, particularly 2%, particularly 1%, particularly 0.1%. and is particularly of 0%.

In the present application the term "probe" designates a tool used for the detection and localisation of a specific target.

The term "imaging" designates non-invasive techniques and processes used to create images of the human body (or parts and function thereof) for clinical purposes (medical procedures seeking to reveal, diagnose or examine disease) or medical science (including the study of normal anatomy and physiology).

The term "cancer cells" designates a group of cells displaying uncontrolled growth (division beyond the normal limits), invasion (intrusion on and destruction of adjacent tissues), and sometimes metastasis (spread to other locations in the body via lymph or blood).

Photodynamic therapy with the compositions of the present invention is appropriate to treat all solid cancers, and more particularly cancers with a size inferior to 1 cm and metastasis, and more particularly urological cancers (kidney, bladder, prostate, testicles), and more particularly prostate cancer. This therapy is also adapted to gastrointestinal cancers (oesophagus, stomach, liver, pancreas, bile ducts, and colon rectum) and more particularly colorectal cancer. This therapy is also adapted to retinoblastoma and breast cancer.

The human body is not transparent to visible wavelengths. Hence, one photon imaging using fluorescent dyes is not very efficient. If the same dye had good two-photon absorption, then the corresponding excitation would occur at approximately twice the wavelength at which one-photon excitation would have occurred. As a result, it is possible to use excitation in the near infrared region where the human body shows good transparency.

According to an advantageous embodiment, the invention relates to the use of at least one pharmaceutical composition as defined above,
for the implementation of a probe enabling the imaging of cancer cells.

According to another embodiment the invention relates to the use of at least
one compound as defined above, or
one nanoparticle composition as defined above, or
for the preparation of a medicament for the treatment of cancer and medical imaging of tumours.

According to an advantageous embodiment, the invention relates to the use of a compound or a silica nanoparticle composition as defined above, wherein the irradiation time of the said compound or nanoparticle ranges from about 3 seconds to 60 minutes, particularly from about 3 seconds to 15 minutes, particularly from about 3 seconds to 9 minutes.

According to an advantageous embodiment, the invention relates to the use of a compound or a silica nanoparticle composition as defined above, wherein said compound used as a photosensitizer is excited by a biphotonic irradiation, said biphotonic irradiation wavelength value ranges from about 650 nm to 1200 nm, particularly from about 720 nm to 900 nm.

According to an advantageous embodiment, the invention relates to the use of a compound or a silica nanoparticle composition as defined above, wherein the two-photon absorption cross section of said compound used as a photosensitizer is higher than about 300 GM, particularly higher than about 750 GM, for at least one wavelength value ranging from 720 nm to 900 nm.

FIGURES

FIG. 1A represents 3 pictures of MDA-MB-231 cells taken with a microscope.

The left part of FIG. 1A represents control cells. The cells were not incubated with compounds according to the present invention, but were treated by biphotonic irradiation.

The middle part of FIG. 1A represents cells incubated for 24 hours with silica nanoparticles DB052, and treated by biphotonic irradiation.

The right part of FIG. 1A represents cells incubated for 24 hours with mannose coated silica nanoparticles DB069, and treated by biphotonic irradiation.

FIG. 1B represents a picture of MDA-MB-231 cells incubated with DB069 nanoparticles for 24 h. The picture is divided in two areas materialized by a dotted curve. The right side of the picture corresponds to cells which have been treated by a biphotonic irradiation; the left side of the picture corresponds to cells which have not been treated by a biphotonic irradiation.

FIGS. 1A and 1B demonstrate the specificity of the photodynamic therapy with the particles according to the present invention. Cells death is observed and occurs in the irradiated area when the cells have been incubated with nanoparticles according to the present invention.

FIG. 2A represents 3 pictures of MDA-MB-231 cells taken with a microscope.

The left part of FIG. 2A represents control cells. The cells were not incubated with compounds according to the present invention, but were treated by biphotonic irradiation.

The middle part of FIG. 2A represents cells incubated for 24 hours with silica nanoparticles DB052, and treated by biphotonic irradiation.

The right part of FIG. 2A represents cells incubated for 24 hours with mannose coated silica nanoparticles DB069, and treated by biphotonic irradiation.

The histogram is constituted by six columns, each related to a different experiment. The ordinate axis represents the percentage of living cells in each experiment with respect to the control.

The first column from the left represents the control cells. These cells were not treated by irradiation, and not incubated with either DB052 (nanoparticle without surface coating) or DB069 (nanoparticle with mannose surface coating) nanoparticles.

The second column from the left represents irradiated cells that were not incubated with either DB052 or DB069 nanoparticles. Cell survival is 100% (with respect to the control cells).

The third column from the left represents irradiated cells that were incubated with DB052 nanoparticles. Cell survival is 67% (with respect to the control cells).

The fourth column from the left represents irradiated cells that were incubated with DB069 nanoparticles. Cell survival is 24% (with respect to the control cells).

The fifth column from the left represents unirradiated cells that were incubated with DB052 nanoparticles. Cell survival is 107% (with respect to the control cells).

The sixth column from the left represents unirradiated cells that were incubated with DB069 nanoparticles. Cell survival is 108% (with respect to the control cells).

The efficiency of the photodynamic treatment is demonstrated by the death of 33% of the cells incubated with nanoparticles DB052, and by the death of 76% of the cells incubated with DB069. Therapeutical efficiency is improved by mannose coating of the nanoparticles surface. Moreover, the absence of toxicity of the unirradiated nanoparticles demonstrates the specificity of the photodynamic therapy with the compounds according to the present invention.

Figure 3A:
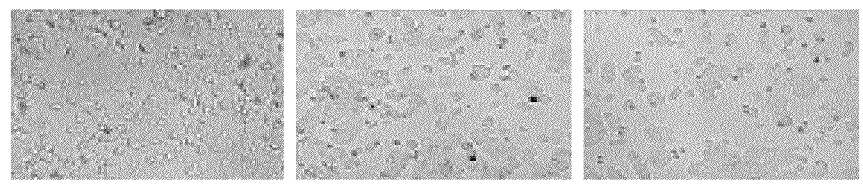

FIG. 3A represents 3 pictures of MCF7 cells taken with a microscope.

The left part of FIG. 3A represents control cells. The cells were not incubated with compounds according to the present invention, but were treated by biphotonic irradiation.

The middle part of FIG. 3A represents cells incubated for 2 hours with silica nanoparticles DB052, and treated by biphotonic irradiation.

The right part of FIG. 3A represents cells incubated for 2 hours with mannose coated silica nanoparticles DB069, and treated by biphotonic irradiation.

Figure 3B:
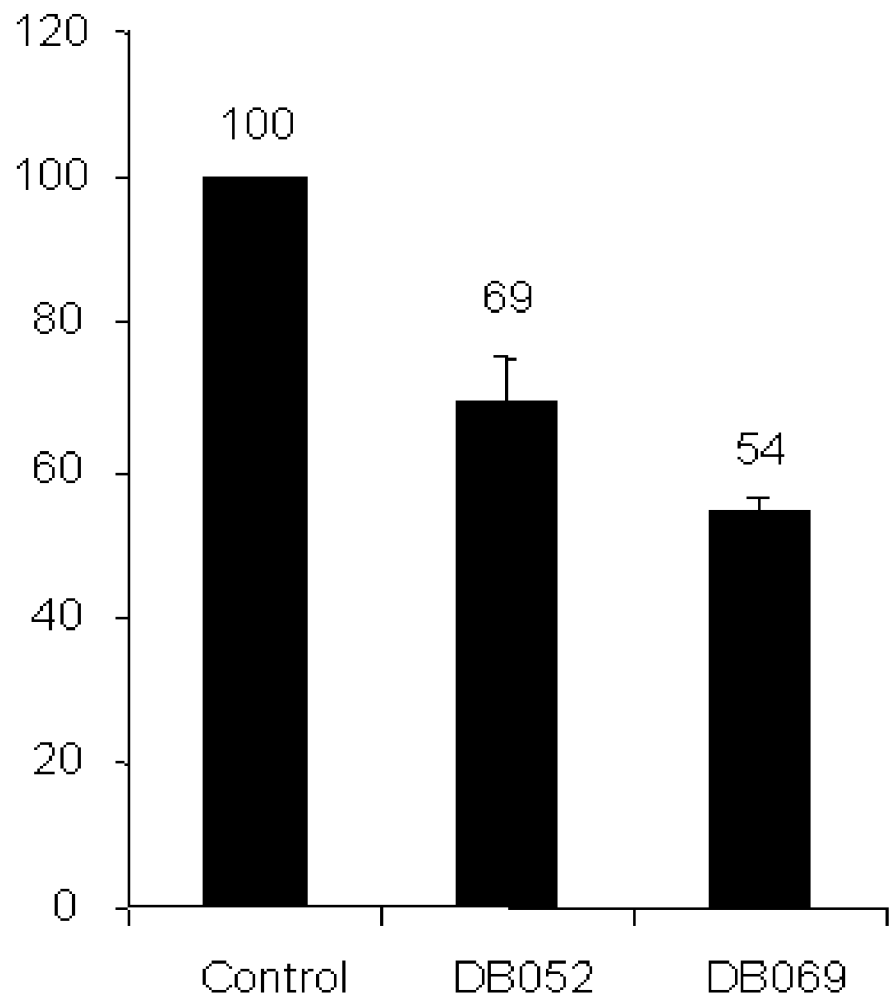

FIG. 3B represents a histogram indicating the percentage of living MCF7 cells with respect to a control experiment of untreated MCF7 cells (no nanoparticles and no irradiations).

The histogram is constituted by three columns, each related to a different experiment. The ordinate axis represents the percentage of living cells in each experiment with respect to the control.

The left column of FIG. 3B represents the control cells. These cells were not treated by irradiation, and not incubated with either DB052 (nanoparticle without surface coating) or DB069 (nanoparticle with mannose surface coating) nanoparticles.

The middle column of FIG. 3B represents irradiated cells (3 seconds irradiation) that were incubated for 2 hours with DB052 nanoparticles. Cell survival is 69% (with respect to the control cells).

The right column of FIG. 3B represents irradiated cells (3 seconds irradiation) that were incubated for 2 hours with DB069 nanoparticles. Cell survival is 54% (with respect to the control cells).

FIGS. 3A and 3B show cellular death induced by photodynamic treatment with the particles according to the present invention. Efficiency of the therapy is demonstrated by the death of 31% of the cells irradiated and incubated with nanoparticles DB052, and death of 46% of the cells irradiated and incubated with nanoparticles DB069, after 2 hours of incubation with the said nanoparticles.

Figure 4A:
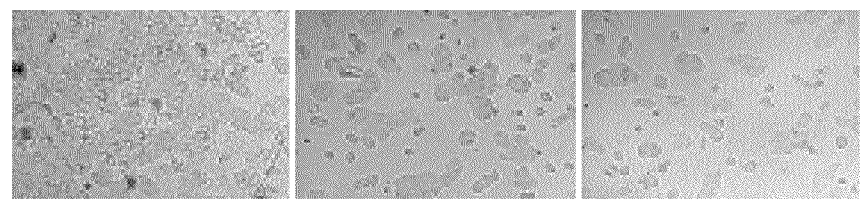

FIG. 4A represents 3 pictures of MCF7 cells taken with a microscope.

The left part of FIG. 4A represents control cells. The cells were not incubated with compounds according to the present invention, but were treated by biphotonic irradiation.

The middle part of FIG. 4A represents cells incubated for 4 hours with silica nanoparticles DB052, and treated by biphotonic irradiation.

The right part of FIG. 4A represents cells incubated for 4 hours with mannose coated silica nanoparticles DB069, and treated by biphotonic irradiation.

Figure 4B:
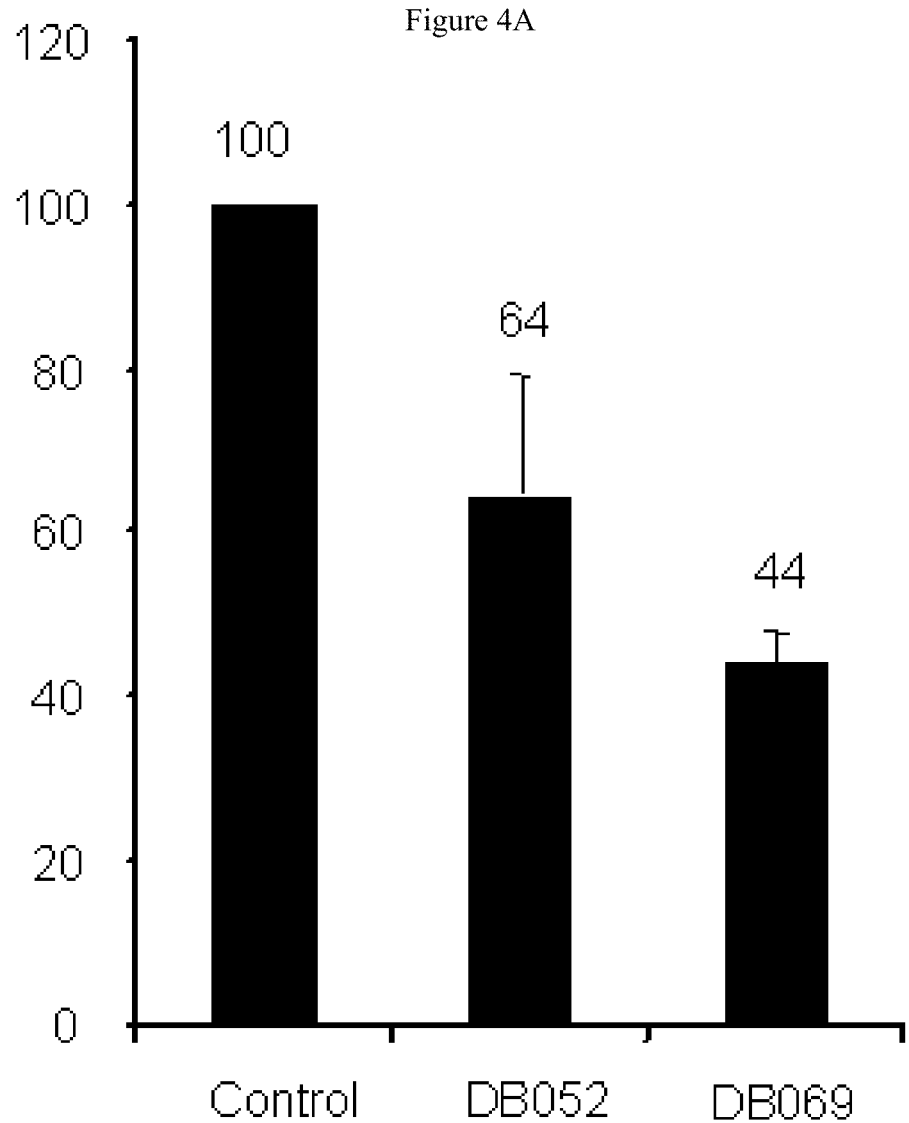

FIG. 4B represents a histogram indicating the percentage of living MCF7 cells with respect to a control experiment of untreated MCF7 cells (no nanoparticles and no irradiations).

The histogram is constituted by three columns, each related to a different experiment. The ordinate axis represents the percentage of living cells in each experiment with respect to the control.

The left column represents the control cells. These cells were not treated by irradiation, and not incubated with either DB052 (nanoparticle without surface coating) or DB069 (nanoparticle with mannose surface coating) nanoparticles.

The middle column represents irradiated cells (3 seconds irradiation) that were incubated for 4 hours with DB052 nanoparticles. Cell survival is 64% (with respect to the control cells).

The right column represents irradiated cells (3 seconds irradiation) that were incubated for 4 hours with DB069 nanoparticles. Cell survival is 44% (with respect to the control cells).

FIGS. 4A and 4B show cellular death induced by photodynamic treatment with the particles according to the present invention. Efficiency of the therapy is demonstrated by the death of 36% of the cells irradiated and incubated with nanoparticles DB052, and death of 56% of the cells irradiated and incubated with nanoparticles DB069, after 4 hours of incubation with the said nanoparticles.

FIGS. 3A, 3B, 4A and 4B demonstrate an increase in the therapeutical efficiency of nanoparticles surface coated with mannose.

Figure 5:
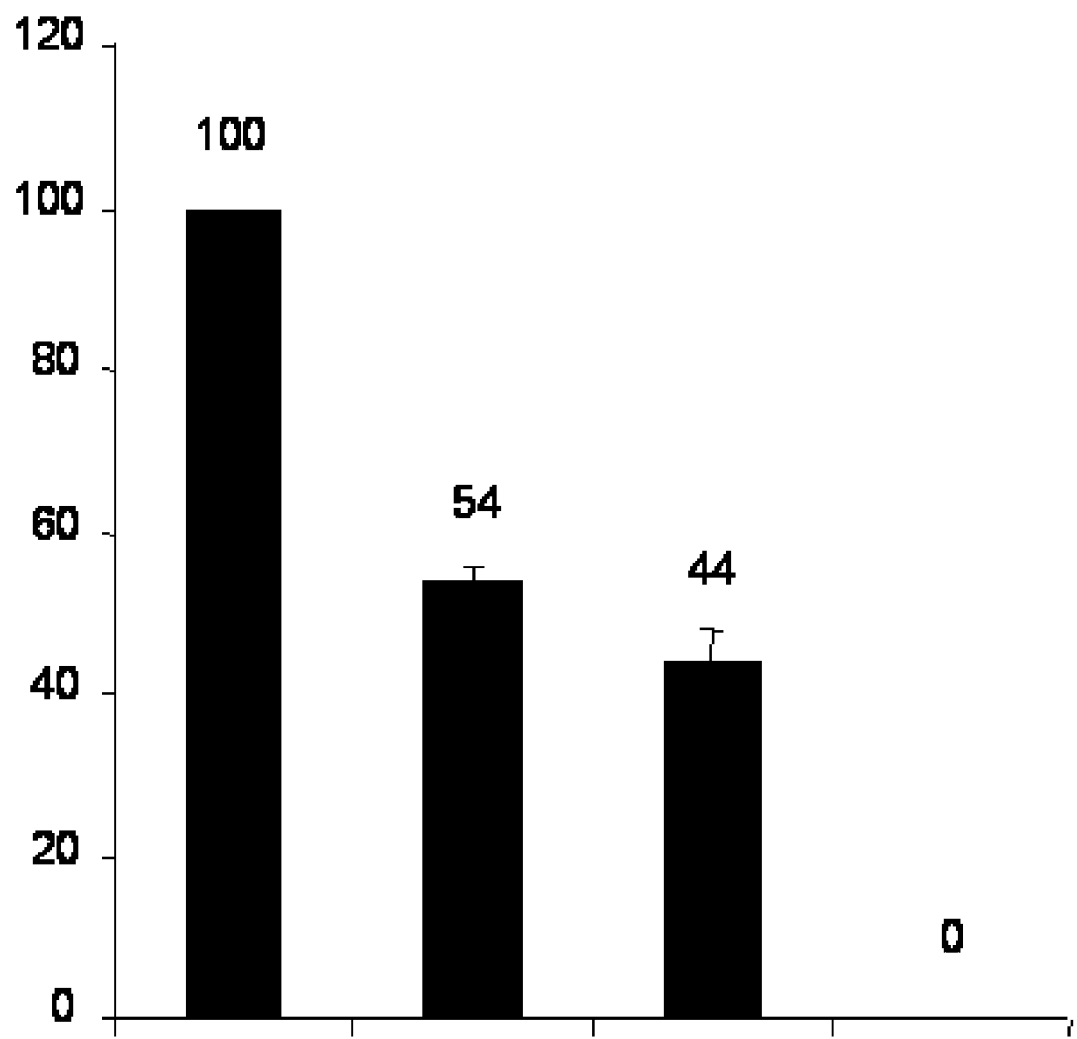

FIG. 5 represents a histogram indicating the percentage of living MDA-MB-231 cells with respect to a control experiment of untreated MCF7 cells (no nanoparticles and no irradiation).

The histogram is constituted by four columns, each related to a different experiment. The ordinate axis represents the percentage of living cells in each experiment with respect to the control.

The first column from the left represents the control cells. These cells were not treated by irradiation, and not incubated with DB069 (nanoparticle with mannose surface coating) nanoparticles.

The second column from the left represents irradiated cells (3 seconds irradiation) that were incubated for 2 hours with DB069 nanoparticles. Cell survival is 54% (with respect to the control cells).

The third column from the left represents irradiated cells (3 seconds irradiation) that were incubated for 4 hours with DB069 nanoparticles. Cell survival is 44% (with respect to the control cells).

The fourth column from the left represents irradiated cells (3 seconds irradiation) that were incubated for 24 hours with DB069 nanoparticles. None of these cells survived, thus no column is visible.

FIG. 5 demonstrates that the efficiency of the photodynamic therapy increases with the incubation time of the cells with the nanoparticles according to the present invention.

Figure 6:
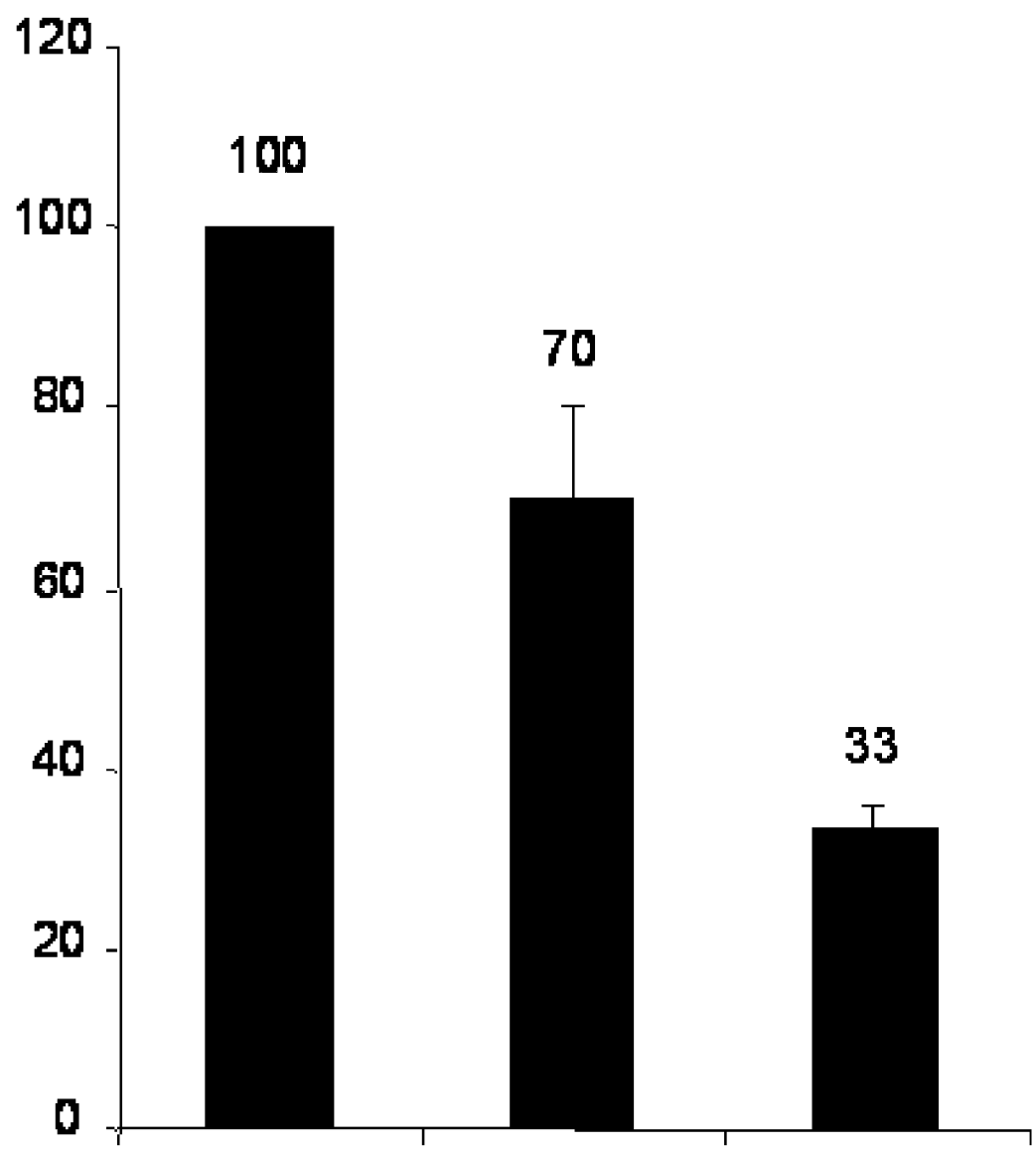

FIG. 6 represents a histogram indicating the percentage of living Y-79 cells with respect to a control experiment of untreated Y-79 cells (no nanoparticles and no irradiation).

The histogram is constituted by three columns, each related to a different experiment. The ordinate axis represents the percentage of living cells in each experiment with respect to the control.

The left column represents the control cells. These cells were not treated by irradiation, and not incubated with either DB052 (nanoparticle without surface coating) nanoparticles, or DB069 (nanoparticle with mannose surface coating) nanoparticles.

The middle column represents irradiated cells (3 seconds irradiation) that were incubated for 24 hours with DB052 nanoparticles. Cell survival is 70% (with respect to the control cells).

The right column represents irradiated cells (3 seconds irradiation) that were incubated for 24 hours with DB069 nanoparticles. Cell survival is 33% (with respect to the control cells).

FIG. 6 demonstrates that DB052 and DB069 particles according to the present invention induced cytotoxicity over retinoblastoma cells Y-79.

These results show an increased efficiency for mannose coated nanoparticles (DB069).

FIGS. 7A, 7B, 7C, 7D, 7E represent 5 pictures of HCT-116 cells taken with a microscope.

Figure 7A:
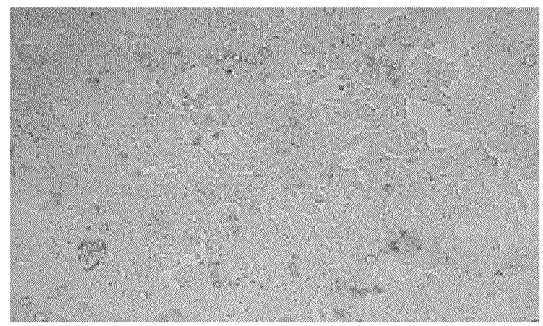

FIG. 7A represents control cells. The cells were not incubated with compounds according to the present invention, and were treated by biphotonic irradiation.

Figure 7B:
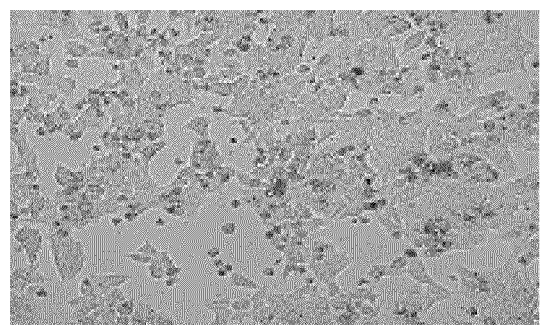

FIG. 7B represents cells incubated for 4 hours with silica nanoparticles DB052 (silica nanoparticle containing photosensitizer 7a (2.90 µmol/g), without mannose coating, without cyclobutenedione-aminophenyl coating), and treated by biphotonic irradiation.

Figure 7C:
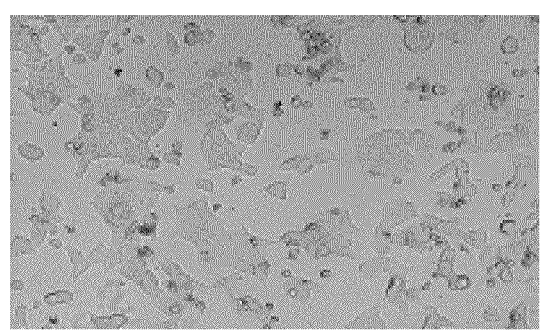

FIG. 7C represents cells incubated for 4 hours with silica nanoparticles DB069 (silica nanoparticle containing photosensitizer 7a (2.90 µmol/g), mannose coated (mannose concentration: 0.532 mmol/g), and cyclobutenedione coated (cyclobutadienedione concentration: 0.532 mmol/g)), and treated by biphotonic irradiation.

Figure 7D:
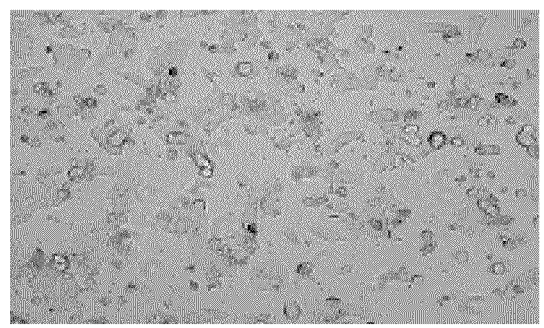

FIG. 7D represents cells incubated for 4 hours with silica nanoparticles DB060 (silica nanoparticle containing photosensitizer 7a (4.50 µmol/g), without mannose coating, without cyclobutenedione-aminophenyl coating), and treated by biphotonic irradiation.

Figure 7E:
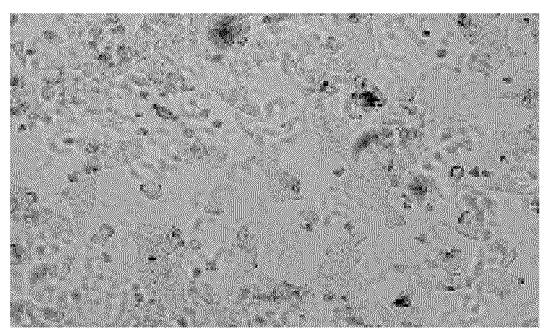

FIG. 7E represents cells incubated for 4 hours with mannose coated silica nanoparticles DB103 (silica nanoparticle containing photosensitizer 7a (4.50 µmol/g), mannose coated (mannose concentration: 0.089 mmol/g), and cyclobutadienedione-aminophenyl coated (cyclobutenedione-aminophenyl concentration: 0.089 mmol/g)), and treated by biphotonic irradiation.

FIGS. 7A to 7E show an improved therapeutical efficiency of the nanoparticles containing a larger amount of photosensitizer, and an improved therapeutical efficiency of the mannose coated nanoparticles. Biphotonic irradiation without nanoparticles does not induce cell death.

Figure 8:
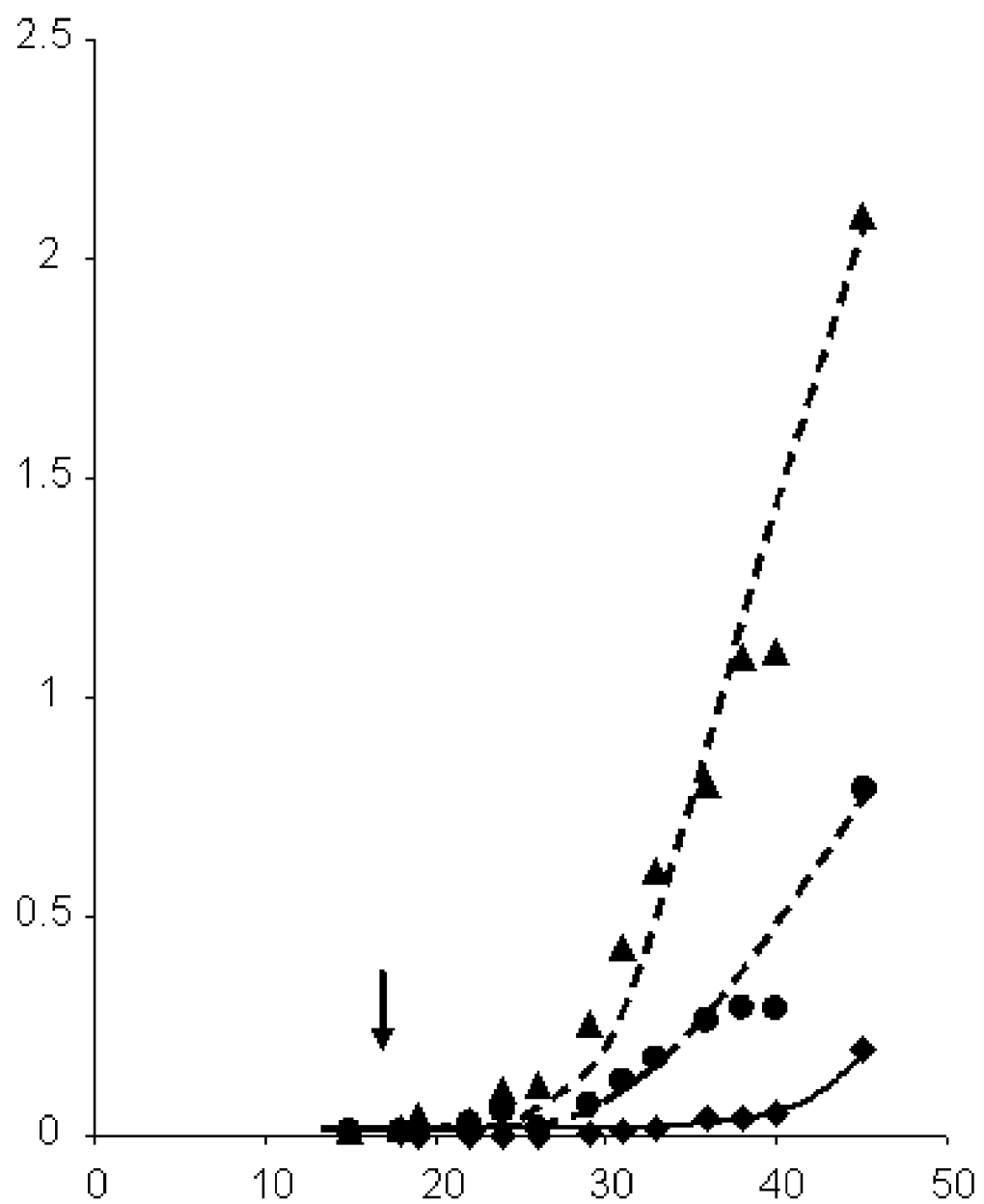

FIG. 8 is a graph representing the growth of HCT-116 tumor cells injected in nude mice. The initial size of the tumor ranges from 0.009 to 0.01 cm$^3$. Tumor volumes are measured every two days.

The abscissa axis represents the days after injection of the tumor cells. The ordinate axis represents the tumor volume in cm$^3$. The arrow indicates the two-photon irradiation. Mice are treated by one irradiation (3 times 3 minutes, with 0.25 second between two exposition). Three sets of results are plotted on this graph.

First set represented by triangles corresponds to tumor volumes of control mice (no two-photon irradiation, and no nanoparticles according to the present invention). A linear regression curve is plotted (dash symbols).

Second set represented by dots corresponds to tumor volumes of mice treated by two-photon irradiation, but not treated with nanoparticles according to the present invention. A linear regression curve is plotted (dash symbols).

Third set represented by diamonds corresponds to tumor volumes of mice treated by two-photon irradiation, and treated with DB069 nanoparticles according to the present invention. A linear regression curve is plotted.

FIG. 8 demonstrates that small tumors react strongly to photodynamic therapy with nanoparticles according to the present invention.

Figure 9:
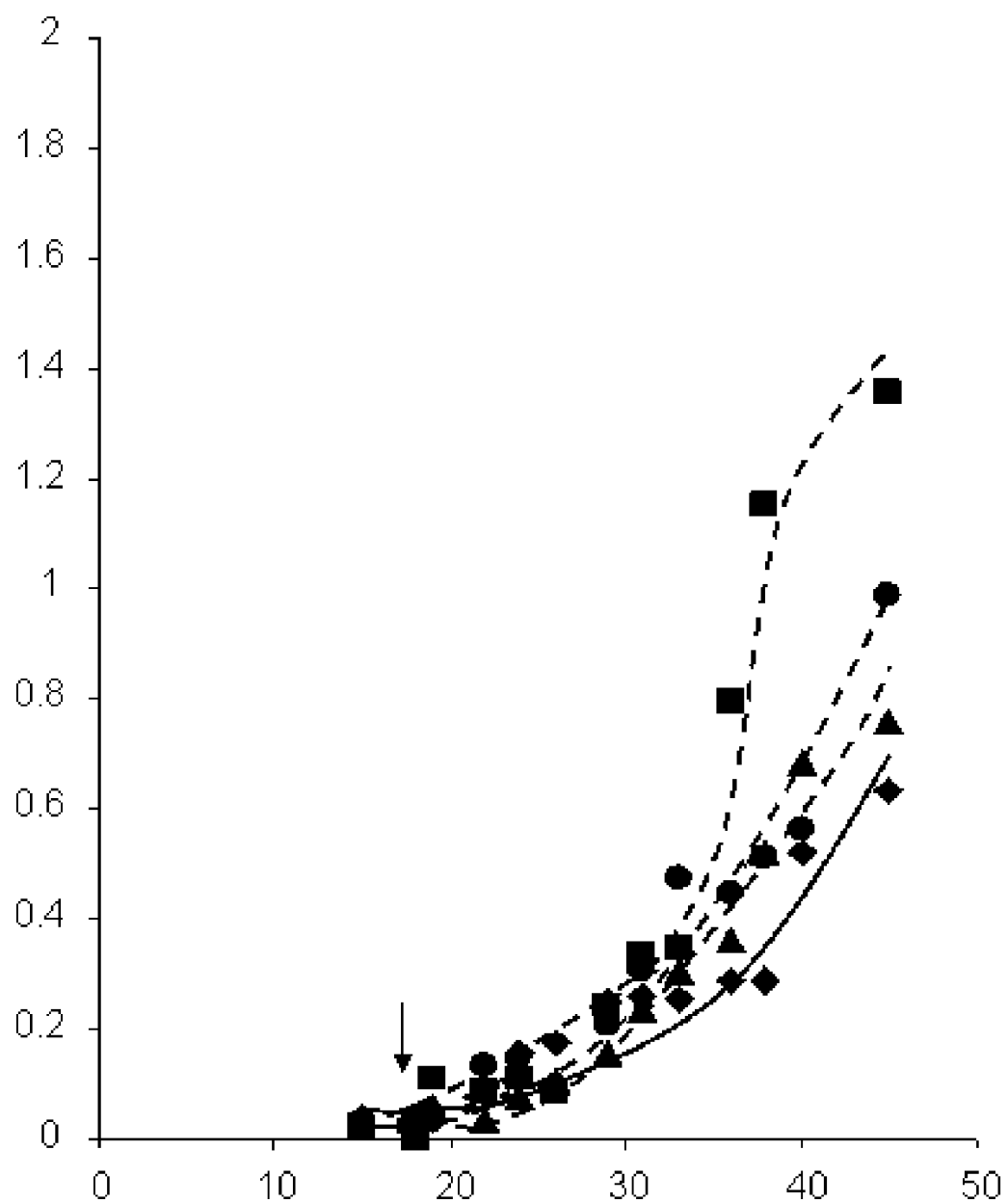

FIG. 9 is a graph representing the growth of HCT-116 tumor cells injected in nude mice. The initial size of the tumor ranges from 0.02 to 0.04 cm$^3$. Tumor volumes are measured every two days.

The abscissa axis represents the days after injection of the tumor cells. The ordinate axis represents the tumour volume in cm$^3$. The arrow indicates the two-photon irradiation. Mice are treated by one irradiation (3 times 3 minutes, with 0.25 second between two exposition).

Four sets of results are plotted on this graph.

The first set represented by triangles corresponds to tumor volumes of control mice (no two-photon irradiation, and no nanoparticles according to the present invention). A linear regression curve is plotted (dash symbols).

The second set represented by dots corresponds to tumor volumes of mice treated by two-photon irradiation, but not treated with nanoparticles according to the present invention. A linear regression curve is plotted (dash symbols).

The third set represented by squares corresponds to tumor volumes of mice treated with nanoparticles according to the present invention, but not treated by two-photon irradiation. A linear regression curve is plotted (dash symbols).

The fourth set represented by diamonds corresponds to tumor volumes of mice treated by two-photon irradiation, and treated with DB069 nanoparticles according to the present invention. A linear regression curve is plotted.

FIG. 9 demonstrates that medium sized tumors react to photodynamic therapy with nanoparticles according to the present invention, their growth rate in decreased.

Figure 10:
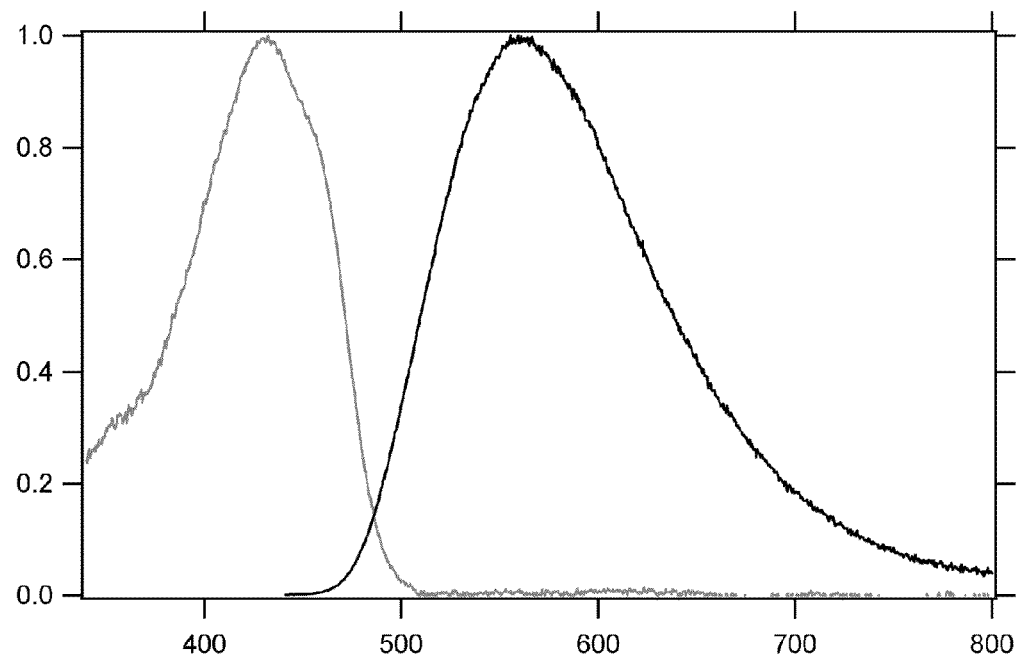

FIG. 10 represents the absorption and emission spectra of compound 6a in ethanol.

The abscissa axis represents the emission or absorption radiation wavelength in nm. The ordinate axis represents the normalized relative intensity of the radiation in an arbitrary unit.

Two curves are represented. The fist curve from the left (grey) represents the absorption spectrum of compound 6a. The second curve from the left (black) represents the emission spectrum of compound 6a.

Figure 11:
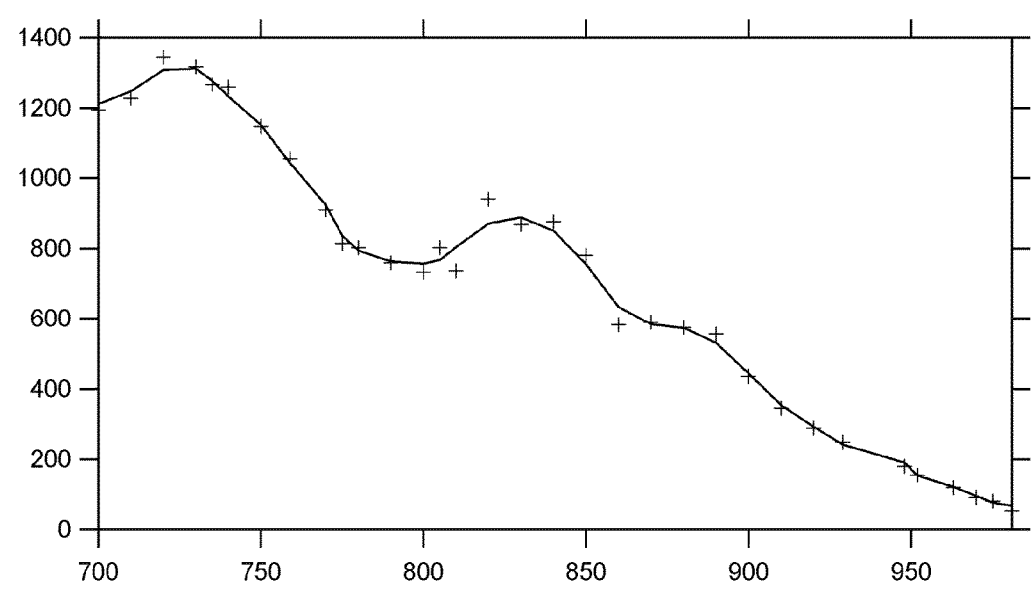

FIG. 11 represents the two photon absorption cross section of compound 6a with respect to different wavelengths, in THF.

The abscissa axis represents the absorption radiation wavelength in nm. The ordinate axis represents the two photon absorption cross section in GM.

Figure 12:
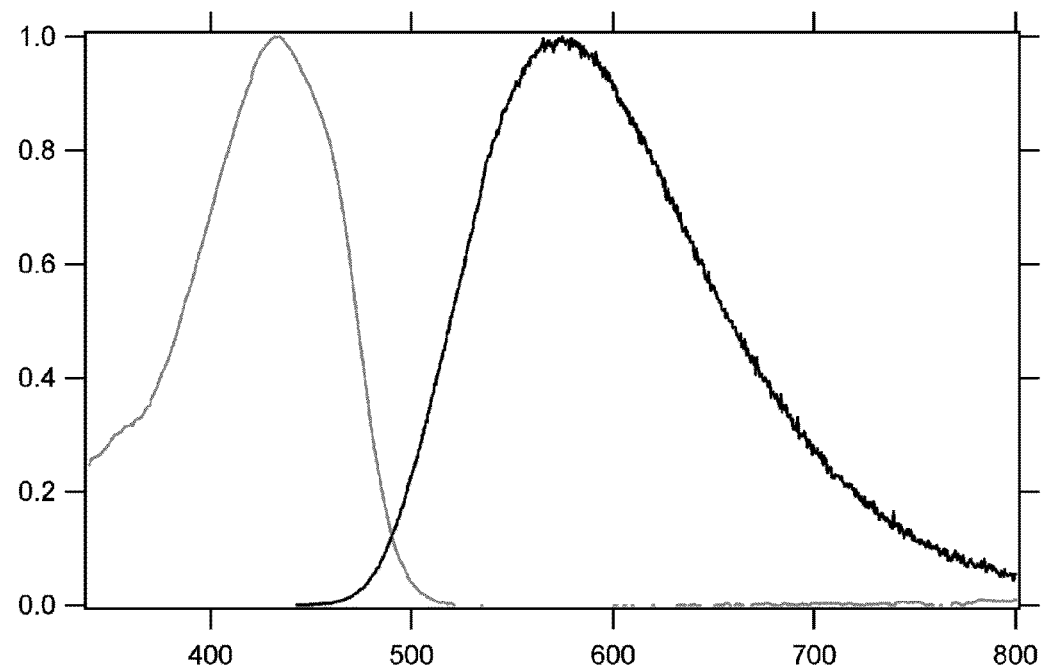

FIG. 12 represents the absorption and emission spectra of compound 6b in ethanol.

The abscissa axis represents the emission or absorption radiation wavelength in nm. The ordinate axis represents the normalized relative intensity of the radiation in an arbitrary unit.

Two curves are represented. The fist curve from the left (grey) represents the absorption spectrum of compound 6b. The second curve from the left (black) represents the emission spectrum of compound 6b.

Figure 13:
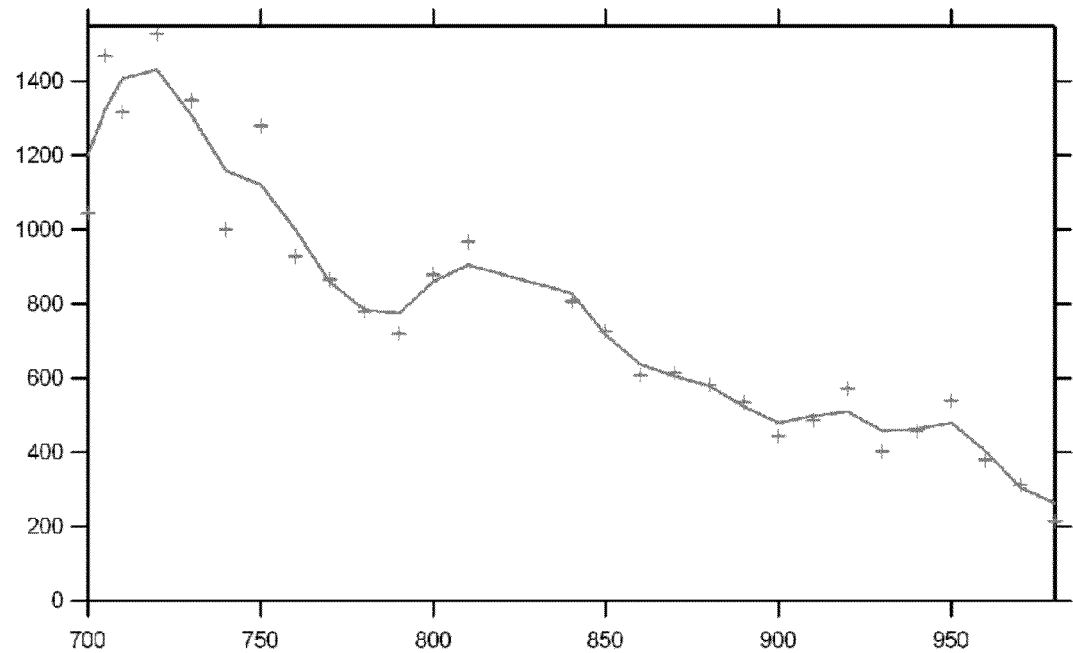

FIG. 13 represents the two photon absorption cross section of compound 6b with respect to different wavelengths, in THF.

The abscissa axis represents the absorption radiation wavelength in nm. The ordinate axis represents the two photon absorption cross section in GM.

Figure 14:
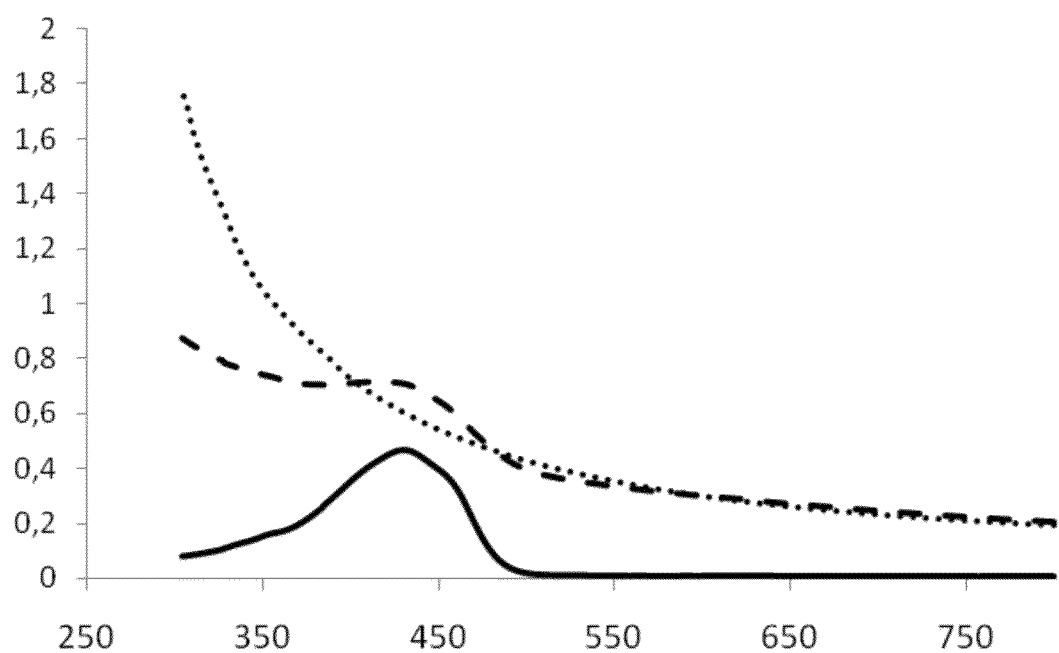

FIG. 14 represents UV-Visible absorption spectra in ethanol.

The abscissa axis represents the absorption radiation wavelength in nm. The ordinate axis represents the normalized relative absorbance intensity in an arbitrary unit.

Three curves are represented. The fist curve (black line) represents the absorption spectrum of photosensitizer 6a. The second curve (black dots) represents the absorption spectrum of the nanoparticle without photosensitizer. The third curve (black dashes) represents the absorption spectrum of the nanoparticle DB060 (with encapsulated photosensitizer 6a).

EXPERIMENTAL PART

A Photosensitizer Synthesis
  Compounds with a Chemically Reactive Group
  General Methods
  All air- or water-sensitive reactions were carried out under dry argon. Solvents were generally dried and distilled prior to use. Reactions were monitored by thin-layer chromatography on Merck silica gel 60 $F_{254}$ precoated aluminum sheets. Column chromatography: Merck silica gel Si 60 (40-63 μm, 230-400 mesh or 63-200 μm, 70-230 mesh). Melting points were determined on an Electrothermal IA9300 digital melting point instrument. NMR: Bruker ARX 200 ($^1$H, 200.13 MHz, $^{13}$C, 50.32 MHz) or Avance AV 300 ($^1$H, 300.13 MHz, $^{13}$C, 75.48 MHz), in CDCl$_3$ solutions; $^1$H chemical shifts (δ) are given in ppm relative to TMS (tetramethylsilane) as internal standard, J values in Hz and $^{13}$C chemical shifts relative to the central peak of CDCl$_3$ at 77.0 ppm. High and low resolution mass spectra measurements were performed at the Centre Régional de Mesures Physiques de l'Ouest (C.R.M.P.O., Rennes), using a Micromass MS/MS ZABSpec TOF instrument with EBE TOF geometry; LSIMS (Liquid Secondary Ion Mass Spectrometry) at 8 kV with Cs$^+$ in m-nitrobenzyl alcohol (mNBA); ES$^+$ (electrospray ionization, positive mode) at 4 kV; EI (Electron Ionization) at 70 eV. Elemental analyses were performed at C.R.M.P.O.

Example 1

General Synthesis of the Fluorene Core 2,7-diiodofluorene has been taken in toluene and sonicated for 3 minutes. Tetrabutylammonium bromide (TBAB) was added, followed by addition of the appropriate alkyl halide or tosylate in toluene. Finally, NaOH (50 wt. % solution) was added. The reaction mixture was degassed and heated to 60° C. under argon for 20 hours and then cooled to room temperature. Then the reaction mixture was diluted with CH$_2$Cl$_2$ and water. The organic layer was separated and the aqueous layer was extracted with CH$_2$Cl$_2$. The combined organic layers were washed with water, then washed with 1M HCl and finally with saturated NaCl solution and dried with anhydrous Na$_2$SO$_4$. After evaporation to dryness, the crude sample was purified by column chromatography on silica gel to yield the corresponding 9,9-dialkyl-2,7-diiodo-9H-fluorene.

Example 2

General Synthesis of the Photosensitizers

The fluorene cores were obtained from the corresponding 9,9-dialkyl-2,7-diiodo-9H-fluorene by means of a twofold palladium(II)-catalyzed cross-coupling with 2-methyl-3-butyn-2-ol, followed by base-promoted deprotection of the resulting intermediate. Double Sonogashira couplings of 9,9-dialkyl-2,7-diethynyl-9H-fluorene with the appropriate (3,4-substituted or not) 5-iodothiophene-2-carboxaldehyde afforded the corresponding 5,5'-(9,9-dialkyl-9H-fluorene-2,7-diyldi-2,1-ethynediyl)bis-2-thiophenecarboxaldehyde. Wittig condensations of these dialdehydes with [[4-[ethyl(2-hydroxyethyl)amino]phenyl]methyl]triphenylphosphonium iodide (Porres, L.; Bhatthula, B. K. G.; Blanchard-Desce, M. *Synthesis* 2003, 1541-1544) led to the corresponding photosensitizers, as single (E,E)-stereoisomers.

Example 3

4,4'-(9,9-Dibutyl-9H-fluorene-2,7-diyl)bis(2-methyl-3-butyn-2-ol)

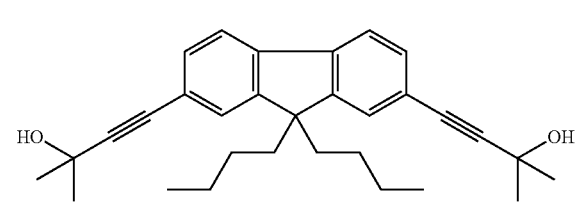 [SMILES: CCCCC1(CCCC)c2cc(C#CC(C)(C)O)ccc2-c2ccc(C#CC(C)(C)O)cc21]

Air was removed from a solution of 9,9-dibutyl-2,7-diiodo-9H-fluorene (Li, F.; Chen, Z.; Wei, W.; Cao, H.; Gong, Q.; Teng, F.; Qian, L.; Wang, Y. *J. Phys. D: Appl. Phys.* 2004, 37, 1613-1616.) (6.00 g, 11.3 mmol) in 37.5 mL of toluene/Et$_3$N (5/1) by blowing argon for min. Then CuI (86 mg, 0.45 mmol), Pd(PPh$_3$)$_2$Cl$_2$ (316 mg, 0.45 mmol) and 2-methyl-3-butyn-2-ol (2.84 g, 33.8 mmol) were added, and the mixture was stirred at 40° C. for 16 h. After evaporation of the solvent, the residue was purified by column chromatography (heptane/CH$_2$Cl$_2$ 30:70 then CH$_2$Cl$_2$) to yield 4.37 g (87%) of 4,4'-(9,9-dibutyl-9H-fluorene-2,7-diyl)bis(2-methyl-3-butyn-2-ol): $^1$H NMR (200.13 MHz, CDCl$_3$) δ 7.60 (d, J=8.6 Hz, 2H), 7.40 (d, J=8.6 Hz, 2H), 7.38 (s, 2H), 2.16 (s, 2H), 1.94 (m, 4H), 1.66 (s, 12H), 1.07 (m, 4H), 0.66 (t, J=7.3, 6H), 0.52 (m, 4H); $^{13}$C NMR (50.32 MHz, CDCl$_3$) δ 150.8, 140.5, 130.7, 126.0, 121.3, 119.8, 93.9, 82.9, 65.7, 55.0, 40.1, 31.5, 25.7, 23.0, 13.8; HRMS (EI) calcd for $C_{31}H_{38}O_2$ (M$^+$·) m/z 442.2872. found 442.2859. Anal. Calcd for $C_{31}H_{38}O_2$ (442.64): C, 84.12; H, 8.65. Found: C, 84.01; H, 8.71.

Example 4

9,9-Dibutyl-2,7-diethynyl-9H-fluorene

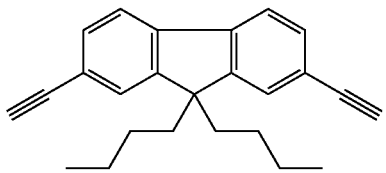 [SMILES: C#Cc1ccc2c(c1)C(CCCC)(CCCC)c1cc(C#C)ccc1-2]

To a solution of 4,4'-(9,9-dibutyl-9H-fluorene-2,7-diyl)bis(2-methyl-3-butyn-2-ol) (1.04 g, 2.35 mmol) in 20 mL of toluene/i-PrOH (3/1), was added solid KOH (0.39 g). The mixture was heated under reflux for 0.5 h. After cooling, KOH was filtered off and the solvents were evaporated and the residue was purified by column chromatography (heptane/CH$_2$Cl$_2$ 70:30 then 20:80) to yield 0.54 g (71%) of 2,7-diethynyl-9,9-dibutyl-9H-fluorene: $^1$H NMR (200.13 MHz, CDCl$_3$) δ 7.63 (d, J=8.6 Hz, 2H), 7.48 (d, J=8.6 Hz, 2H), 7.46 (s, 2H), 3.15 (s, 2H), 1.94 (m, 4H), 1.07 (m, 4H), 0.67 (t, J=7.2 Hz, 6H), 0.54 (m, 4H); $^{13}$C NMR (50.32 MHz, CDCl$_3$) δ 151.0, 140.9, 131.2, 126.5, 120.8, 119.9, 84.5, 77.4, 55.1, 40.0, 25.8, 22.9, 13.7; HRMS (EI) calcd for $C_{25}H_{26}$ (M$^+$·) m/z 326.2035. found 326.2036. Anal. Calcd for $C_{25}H_{26}$ (326.48): C, 91.97; H, 8.03. Found: C, 92.17; H, 8.07.

Example 5

5,5'-(9,9-Dibutyl-9H-fluorene-2,7-diyldi-2,1-ethynediyl)bis-2-thiophenecarboxaldehyde

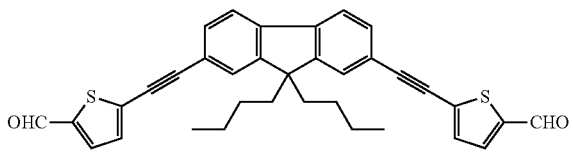 [SMILES: CCCCC1(CCCC)c2cc(C#Cc3ccc(C=O)s3)ccc2-c2ccc(C#Cc3ccc(C=O)s3)cc21]

Air was removed from a solution of 2,7-diethynyl-9,9-dibutyl-9H-fluorene (0.150 g, 0.460 mmol) and 5-iodothiophene-2-carboxaldehyde (Wu, L.-H.; Chu, C.-S.; Jan- arthanan, N.; Hsu, C.-S. J. Polym. Res. 2000, 7, 125-134) (0.251 g, 1.06 mmol) in 6.5 mL of toluene/Et$_3$N (4/1) by blowing argon for 20 min. Then CuI (7.0 mg, 0.0037 mmol) and Pd(PPh$_3$)$_2$Cl$_2$ (27 mg, 0.0039 mmol) were added, and deaeration was continued for 10 min. Thereafter the mixture was stirred at 40° C. for 16 h. The solvent was removed under reduced pressure, and the crude product was purified by column chromatography (heptane/CH$_2$Cl$_2$ 50:50 then 40:60) to yield 245 mg (97%) of 5,5'-(9,9-dibutyl-9H-fluorene-2,7-diyldi-2,1-ethynediyl)bis-2-thiophenecarboxaldehyde; $^1$H NMR (300.13 MHz, CDCl$_3$) δ 9.80 (s, 2H), 7.61 and 7.26 (AX, $J_{AX}$=3.9 Hz, 4H), 7.62 (d, J=8.5 Hz, 2H), 7.47 (d, J=8.5 Hz, 2H), 7.45 (s, 2H), 1.93 (m, 4H), 1.02 (m, 4H), 0.60 (t, J=7.3 Hz, 6H), 0.51 (m, 4H); $^{13}$C NMR (75.46 MHz, CDCl$_3$) δ 182.4, 151.4, 143.9, 141.4, 136.1, 133.0, 132.5, 131.0, 126.0, 120.9, 120.4, 98.9, 82.6, 55.3, 40.1, 25.9, 23.0, 13.8; HRMS (ESI) calcd for $C_{35}H_{30}O_2S_2$ (M$^+$·) m/z 546.16872. found 546.1687.

Example 6

5,5'-(9,9-Dibutyl-9H-fluorene-2,7-diyldi-2,1-ethynediyl)bis(3,4-ethylenedioxy-2-thiophenecarboxaldehyde)

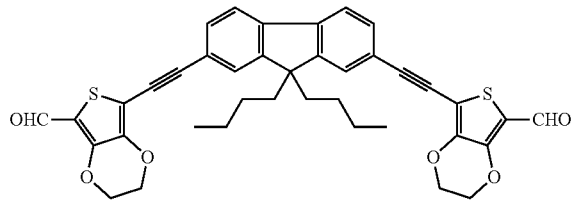 [SMILES: CCCCC1(CCCC)c2cc(C#Cc3sc(C=O)c4c3OCCO4)ccc2-c2ccc(C#Cc3sc(C=O)c4c3OCCO4)cc21]

Air was removed from a solution of 2,7-diethynyl-9,9-dibutyl-9H-fluorene and 5-iodo-3,4-ethylenedioxythiophene-2-carboxaldehyde (Jessing, M.; Brandt, M.; Jensen, K. J.; Christensen, J. B.; Boas, U. J. Org. Chem. 2006, 71, 6734) (2.3 equiv) in toluene/Et$_3$N (4/1) by blowing argon for 20 min. Then CuI (2×4 mol %) and Pd(PPh$_3$)$_2$Cl$_2$ (2×4 mol %) were added, and deaeration was continued for 10 min. Thereafter the mixture was stirred at 40° C. for 16 h. The solvent was removed under reduced pressure, and the crude product was purified by column chromatography on silica gel (heptane/CH$_2$Cl$_2$ 50:50 then 40:60) to yield 5,5'-(9,9-dibutyl-9H-fluorene-2,7-diyldi-2,1-ethynediyl)bis(3,4-ethylenedioxy-2-thiophenecarboxaldehyde).

Example 7

5-[[7-[[5-[(1E)-2-[4-(Dihexylamino)phenyl]ethenyl]thien-2-yl]ethynyl]-9,9-dibutyl-9H-fluorene-2-yl]ethynyl]thiophene-2-carboxaldehyde

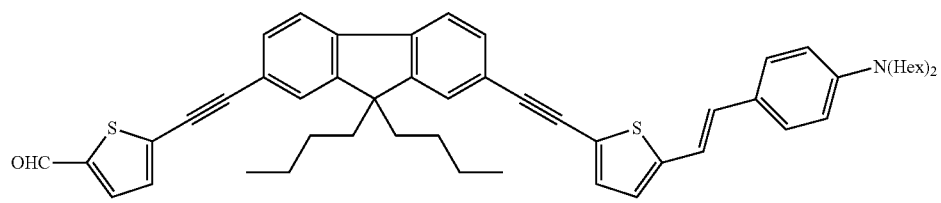

To a solution of 5,5'-(9,9-dibutyl-9H-fluorene-2,7-diyldi-2,1-ethynediyl)bis-2-thiophenecarboxaldehyde (1.14 g, 2.085 mmol) and [[4-(dihexylamino)phenyl]methyl]triphenylphosphonium iodide (1.66 g, 2.501 mmol) in anhydrous CH$_2$Cl$_2$ (40 mL), was added tBuOK (0.352 g, 3.137 mmol). The mixture was stirred at 20° C. for 16 h, then filtered through a short pad of silica gel. The solvent was removed under reduced pressure, and the crude product was purified by column chromatography on silica gel (heptane/CH$_2$Cl$_2$ gradient from 70:30 to 30:70) to yield 701 mg (42%) of 5-[[7-[[5-[(1E)-2-[4-(dihexylamino)phenyl]ethenyl]thien-2-yl]ethynyl]-9,9-dibutyl-9H-fluoren-2-yl]ethynyl]thiophene-2-carboxaldehyde; $^1$H NMR (300.13 MHz, CDCl$_3$) δ 9.88 (s, 1H), 7.70 (d, J=7.8 Hz, 1H), 7.69 and 7.35 (AX, J$_{AX}$=3.9 Hz, 2H), 7.68 (d, J=7.8 Hz, 1H), 7.56-7.49 (m, 4H), 7.33 and 6.61 (AA'XX', J$_{AX}$=8.9 Hz, 4H), 7.17 and 6.87 (AX, J$_{AX}$=3.8 Hz, 2H), 6.95 (d, J=16.0 Hz, 1H), 6.86 (d, J=16.0 Hz, 1H), 3.28 (m, 4H), 2.00 (m, 4H), 1.60 (m, 4H), 1.33 (m, 12H), 1.11 (m, 4H), 0.91 (t, J=6.8 Hz, 6H), 0.69 (t, J=7.3 Hz, 6H), 0.59 (m, 4H).

Example 8

Photosensitizer 6a (Also Referred in the Present Application as Compound CR109)

To a solution of 5,5'-(9,9-Dibutyl-9H-fluorene-2,7-diyldi-2,1-ethynediyl)bis-2-thiophenecarboxaldehyde (0.241 g, 0.441 mmol) and [[4-[ethyl(2-hydroxyethyl)amino]phenyl]methyl]triphenylphosphonium iodide (Porrès, L.; Bhatthula, B. K. G.; Blanchard-Desce, M. *Synthesis* 2003, 1541-1544) (0.576 g, 1.016 mmol) in anhyd CH$_2$Cl$_2$ (10 mL), was added tBuOK (0.149 g, 1.325 mmol). The mixture was stirred at 20° C. for 16 h, then filtered through a short pad of silica gel. The solvent was removed under reduced pressure, and the crude product was purified by column chromatography (CH$_2$Cl$_2$/AcOEt 98:2 then 95:5) to yield 134 mg (35%) of 6a; $^1$H NMR (300.13 MHz, CDCl$_3$) δ 7.66 (d, J=8.0 Hz, 2H), 7.50 (d, J=8.0 Hz, 2H), 7.48 (m, 2H), 7.35 and 6.73 (AA'XX', J$_{AX}$=8.9 Hz, 8H), 7.17 and 6.89 (AX, J$_{AX}$=3.6 Hz, 4H), 6.98 (d, J=16.0 Hz, 2H), 6.85 (d, J=16.0 Hz, 2H), 3.81 (t, J=5.7 Hz, 4H), 3.50 (t, J=5.7 Hz, 4H), 3.50 (q, J=7.1 Hz, 4H), 1.99 (m, 4H), 1.66 (s, 2H), 1.18 (t, J=7.0 Hz, 6H), 1.07 (m, 4H), 0.69 (t, J=7.3 Hz, 6H), 0.59 (m, 4H); $^{13}$C NMR (75.46 MHz, CDCl$_3$) δ 151.1, 148.1, 145.8, 140.7, 132.7, 130.5, 129.6, 127.9, 125.6, 125.0, 124.8, 121.8, 120.4, 120.0, 117.2, 112.5, 94.9, 84.0, 60.3, 55.2, 52.4, 45.6, 40.2, 25.9, 23.1, 13.9, 12.0; HRMS (ESI) calcd for C$_{57}$H$_{61}$N$_2$O$_2$S$_2$ [(M+H)$^+$] m/z 869.41745. found 869.4173.

Photophysical Properties of Photosensitizer 6a in 9 Different Solvents.

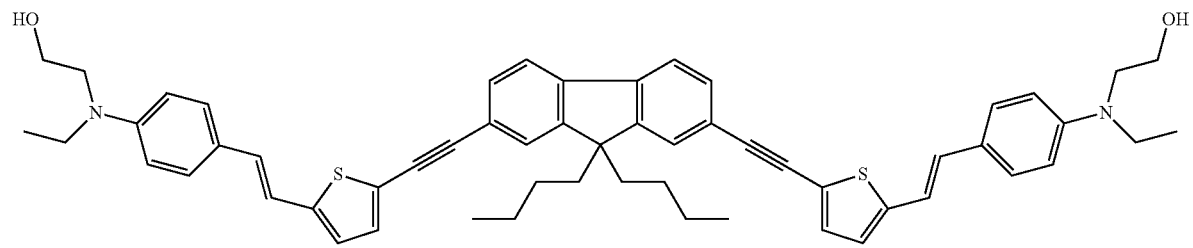 [SMILES: CCCCC1(CCCC)c2cc(C#Cc3ccc(/C=C/c4ccc(N(CC)CCO)cc4)s3)ccc2-c2ccc(C#Cc3ccc(/C=C/c4ccc(N(CC)CCO)cc4)s3)cc21]

| Solvent | λ$_{abs}$ (nm) | λ$_{em}$ (nm) | Stokes shift (cm$^{-1}$) | Φ$_f$$^a$ | τ (ns) | k$_r$$^b$ (10$^9$ s$^{-1}$) | k$_{nr}$$^b$ (10$^9$ s$^{-1}$) | τ$_o$$^c$ (ns) | r$^d$ |
|---|---|---|---|---|---|---|---|---|---|
| Toluene | 436 | 493 | 2650 | 0.48 | 0.93 | 0.52 | 0.56 | 1.94 | 0.16 |
| Bu$_2$O | 433.5 | 491 | 2700 | 0.55 | 0.99 | 0.56 | 0.45 | 1.79 | 0.19 |
| CHCl$_3$ | 431.5 | 522.5 | 4035 | 0.48 | 1.22 | 0.39 | 0.43 | 2.54 | 0.15 |
| AcOEt | 435 | 544 | 4605 | 0.51 | 1.42 | 0.36 | 0.34 | 2.77 | 0.12 |
| THF | 437 | 555 | 4865 | 0.51 | 1.51 | 0.34 | 0.32 | 2.93 | 0.12 |
| DCM | 433.5 | 549.5 | 4870 | 0.61 | 1.43 | 0.42 | 0.27 | 2.35 | 0.10 |
| Acetone | 437.5 | 591.5 | 5950 | 0.22 | 0.88 | 0.25 | 0.89 | 4.02 | 0.13 |
| CH$_3$CN | 436.5 | 604 | 6355 | 0.052 | 1.03 | 0.05 | 0.92 | 19.99 | 0.21 |
| DMSO | 448.5 | 617 | 6090 | 0.051 | 0.49 | 0.10 | 1.94 | 9.7 | 0.28 |

$^a$ Fluorescence quantum yield determined relative to quinine in 0.5 M H$_2$SO$_4$. $^b$ Radiative (k$_r$) and non-radiative (k$_{nr}$) decay rates. $^c$ Radiative lifetime. $^d$ Fluorescence anisotropy.

The absorption and emission spectra of compound 6a in ethanol (FIG. 10), the two photon absorption of compound 6a in THF (FIG. 11) and the UV-Visible absorption spectrum of compound 6a (FIG. 14) are presented.

Example 9

Photosensitizer 9a

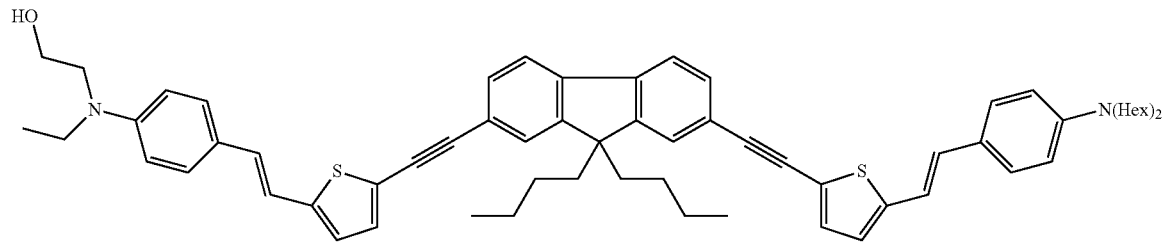

To a solution of 5-[[7-[[5-[(1E)-2-[4-(dihexylamino)phenyl]ethenyl]thien-2-yl]ethynyl]-9,9-dibutyl-9H-fluorene-2-yl]ethynyl]thiophene-2-carboxaldehyde (300 mg, 0.373 mmol 1) and [[4-[ethyl(2-hydroxyethyl)amino]phenyl]methyl]triphenylphosphonium iodide (666 mg, 1.175 mmol) in anhydrous $CH_2Cl_2$ (10 mL), was added tBuOK (219 mg, 1.958 mmol). The mixture was stirred at 20° C. for 16 h, then filtered through a short pad of silica gel. The solvent was removed under reduced pressure, and the crude product was purified by column chromatography on silica gel (heptane/$CH_2Cl_2$ gradient from 50:50 to 20:80) to yield 302 mg (84%) of 9a; $^1$H NMR (300.13 MHz, $CDCl_3$) δ 7.69 (d, J=8.5 Hz, 2H), 7.56 (m, 2H), 7.55 (d, J=8.5 Hz, 2H), 7.38 and 6.75 (AA'XX', $J_{AX}$=8.9 Hz, 4H), 7.38 and 6.66 (AA'XX', $J_{AX}$=8.9 Hz, 4H), 7.22 and 6.922 (AX, $J_{AX}$=3.7 Hz, 2H), 7.22 and 6.912 (AX, $J_{AX}$=3.7 Hz, 2H), 7.02 (d, J=15.9 Hz, 1H), 7.01 (d, J=15.9 Hz, 1H), 6.918 (d, J=15.9 Hz, 1H), 6.908 (d, J=15.9 Hz, 1H), 3.81 (t, J=5.8 Hz, 2H), 3.50 (t, J=5.8 Hz, 2H), 3.46 (q, J=7.1 Hz, 2H), 3.32 (m, 4H), 2.05 (m, 4H), 1.89 (br s, 1H), 1.64 (m, 4H), 1.38 (m, 12H), 1.20 (t, J=7.1 Hz, 3H), 1.16 (m, 4H), 0.97 (t, J=6.6 Hz, 6H), 0.74 (t, J=7.3 Hz, 6H), 0.67 (m, 4H); $^{13}$C NMR (75.46 MHz, $CDCl_3$) δ 151.1, 147.9, 146.0, 145.7, 140.64, 140.57, 132.6, 130.4, 129.9, 129.5, 127.8, 125.6, 125.0, 124.7, 124.4, 123.5, 121.8, 121.7, 120.4, 120.0, 119.9, 117.1, 116.3, 112.5, 111.5, 94.9, 94.7, 84.0, 83.9, 60.2, 55.1, 52.4, 51.0, 45.6, 40.2, 31.7, 27.2, 26.8, 25.9, 23.0, 22.7, 14.0, 13.8, 11.9.

Example 10

Photosensitizer 11a

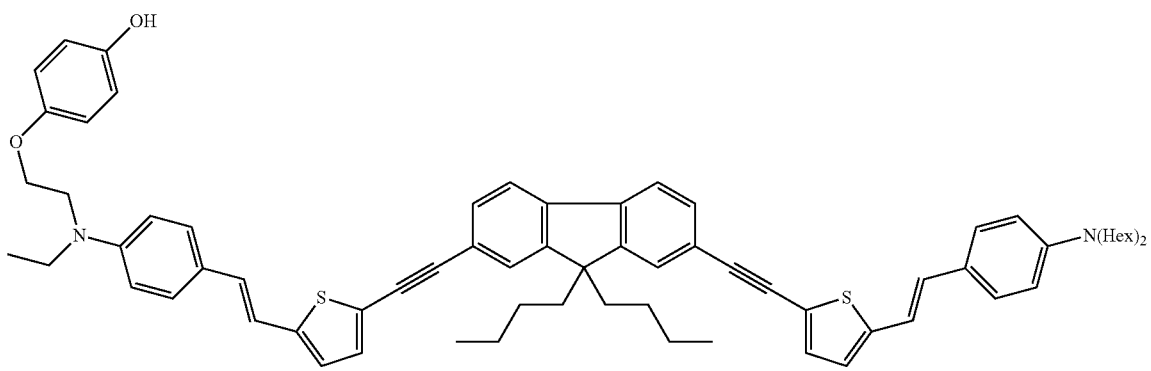

To a solution of 5-[[7-[[5-[(1E)-2-[4-(dihexylamino)phenyl]ethenyl]thien-2-yl]ethynyl]-9,9-dibutyl-9H-fluorene-2-yl]ethynyl]thiophene-2-carboxaldehyde and [[4-[ethyl[2-(4-hydroxyphenoxy)ethyl]amino]phenyl]methyl] triphenylphosphonium iodide in anhydrous $CH_2Cl_2$, was added tBuOK (2 equiv.). The mixture was stirred at 20° C. for 16 h, then filtered through a short pad of silica gel. The solvent was removed under reduced pressure, and the crude product was purified by column chromatography on silica gel (heptane/$CH_2Cl_2$) to yield photosensitizer 11a.

Example 11

Photosensitizer 14

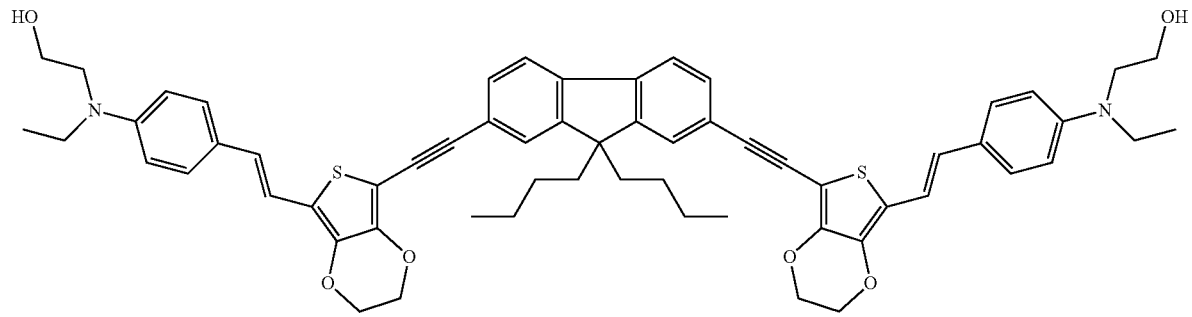 [SMILES: CCCCC1(CCCC)c2cc(C#Cc3sc(/C=C/c4ccc(N(CC)CCO)cc4)c4c3OCCO4)ccc2-c2ccc(C#Cc3sc(/C=C/c4ccc(N(CC)CCO)cc4)c4c3OCCO4)cc21]

To a solution of 5,5'-(9,9-Dibutyl-9H-fluorene-2,7-diyldi-2,1-ethynediyl)bis(3,4-ethylenedioxy-2-thiophenecarboxaldehyde) and [[4-[ethyl(2-hydroxyethyl)amino]phenyl]-methyl]triphenylphosphonium iodide (2.33 equiv.) in anhydrous $CH_2Cl_2$, was added tBuOK (3 equiv.). The mixture was stirred at 20° C. for 16 h, then filtered through a short pad of silica gel. The solvent was removed under reduced pressure, and the crude product was purified by column chromatography on silica gel ($CH_2Cl_2$/AcOEt) to yield photosensitizer 14.

Example 12

2,7-Diiodo-9,9-bis[2-[2-(2-methoxyethoxy)ethoxy]ethyl]-9H-fluorene

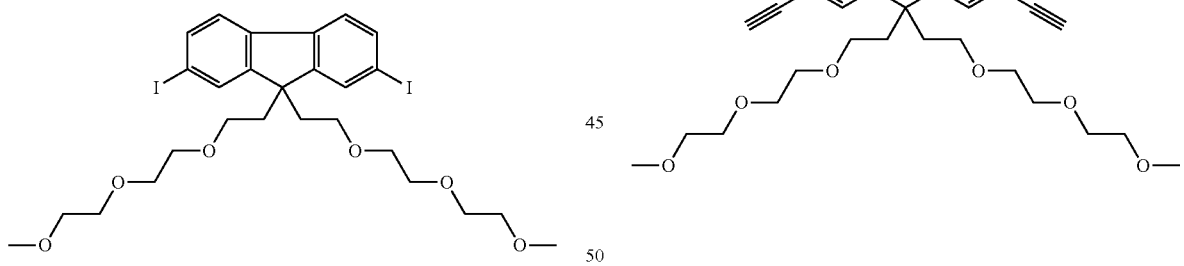

1.0 g of 2,7-diiodofluorene (2.4 mmol) was taken in 4 mL of toluene and sonicated for 3 minutes. To this, 0.25 g of tetrabutylammonium bromide (TBAB) (0.78 mmol) was added, followed by addition of 2.5 g of 2-[2-(2-methoxyethoxy)ethoxy]ethyl p-toluenesulfonate (TEG-OTs, 7.82 mmol) in 2 mL of toluene. Finally, 4 mL of NaOH (50 wt. % solution) were added. The reaction mixture was degassed and heated to 60° C. under argon for 20 hours and then cooled to room temperature. Then the reaction mixture was diluted with 60 mL of $CH_2Cl_2$ and 30 mL of water. The organic layer was separated and the aqueous layer was extracted with $CH_2Cl_2$ (3×15 ml). The combined organic layers were washed with water (2×50 mL), then washed with 1M HCl (50 ml) and finally with 60 mL of saturated NaCl solution and dried with anhydrous $Na_2SO_4$. After evaporation to dryness, the crude sample was purified by column chromatography on silica gel ($CH_2Cl_2$/AcOEt 65:35) to yield 1.0 g of 2,7-Diiodo-9,9-bis[2-[2-(2-methoxyethoxy)ethoxy]ethyl]-9H-fluorene (59%): $^1$H NMR ($CDCl_3$) δ 2.33 (t, 4H, J=7.8 Hz), 2.76 (t, 4H, J=6.9 Hz), 3.21 (m, 4H), 3.35 (s, 6H), 3.39 (m, 4H), 3.56-3.48 (m, 8H), 7.40 (d, 2H, J=8 Hz), 7.67 (dd, 2H, J=8 Hz, J=1.3 Hz), 7.73 (d, 2H, J=1.3 Hz); $^{13}$C NMR ($CDCl_3$) δ 39.4, 51.7, 59.1, 66.7, 70.0, 70.46, 70.49, 71.9, 93.3, 121.6, 132.5, 136.5, 139.1, 150.8. Anal. Calcd for $C_{27}H_{36}O_6I_2$ (710.38): C, 45.65; H, 5.11. Found: C, 46.06; H, 5.12.

Example 13

2,7-Diethynyl-9,9-bis[2-[2-(2-methoxyethoxy)ethoxy]ethyl]-9H-fluorene

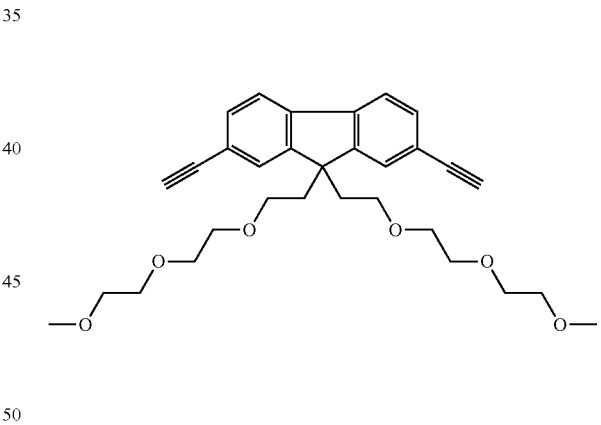

Air was removed from a solution of 2,7-diiodo-9,9-bis[2-[2-(2-methoxyethoxy)ethoxy]ethyl]-9H-fluorene (0.452 g, 0.636 mmol) in 7.5 mL of toluene/$Et_3N$ (4/1) by blowing argon for 20 min. Then CuI (5 mg, 4 mol %), Pd(PPh$_3$)$_2$Cl$_2$ (18 mg, 4 mol %) and 2-methyl-3-butyn-2-ol (0.185 mL, 1.9 mmol) were added, and the mixture was stirred at ° C. for 18 h. The completion of the reaction was monitored by TLC. After evaporation of the solvents, the residue was purified by column chromatography on silica gel ($CH_2Cl_2$/AcOEt 20:80 then AcOEt) to yield 0.372 g (94%) of 4,4'-[9,9-bis[2-[2-(2-methoxyethoxy)ethoxy]ethyl]-9H-fluorene-2,7-diyl]bis(2-methyl-3-butyn-2-ol): $^1$H NMR ($CDCl_3$) δ 1.66 (s, 12H), 2.34 (s, 2H), 2.36 (t, 4H, J=6.9 Hz), 2.72 (t, 4H, J=6.9 Hz), 3.18 (m, 4H), 3.36 (s, 6H), 3.38 (m, 4H), 3.56-3.48 (m, 8H), 7.41 (dd, 2H, J=7.8 Hz, J=1.2 Hz), 7.47 (d, 2H, J=1.2 Hz), 7.59 (d, 2H, J=7.8 Hz); $^{13}$C NMR (CDCl$_3$) δ 15.3, 31.5, 39.6, 51.3, 59.0, 65.6, 66.8, 70.0, 70.4, 71.8, 82.6, 94.5, 112.0, 121.8, 126.6, 131.1, 139.8, 149.2.

To a solution of 4,4'-[9,9-bis[2-[2-(2-methoxyethoxy)ethoxy]ethyl]-9H-fluorene-2,7-diyl]bis(2-methyl-3-butyn-2-ol) (0.363 g, 0.58 mmol) in 9 mL of toluene and 2 mL of i-PrOH, was added solid NaOH (0.15 g, 3.75 mmol). The mixture was heated under reflux for 1.5 h. After cooling, NaOH was filtered off and the solvents were evaporated and the residue was purified by column chromatography on silica gel (CH$_2$Cl$_2$/AcOEt 60:40) to yield 0.171 g (58%) of 2,7-diethynyl-9,9-bis[2-[2-(2-methoxyethoxy)ethoxy]ethyl]-9H-fluorene, mp 68° C.; $^1$H NMR (CDCl$_3$) δ 2.37 (t, 4H, J=7.8 Hz), 2.74 (t, 4H, J=7.2 Hz), 3.17 (s, 2H), 3.20 (m, 4H), 3.35 (s, 6H), 3.39 (m, 4H), 3.54-3.47 (m, 8H), 7.50 (dd, 2H, J=7.8 Hz, J=1.3 Hz), 7.55 (d, 2H, J=1.3 Hz). 7.63 (d, 2H, J=7.8 Hz); $^{13}$C NMR (CDCl$_3$) δ 39.5, 51.3, 59.1, 65.9, 66.8, 70.0, 70.4, 71.8, 77.9, 84.1, 120.1, 121.2, 127.0, 131.7, 140.2, 149.3. Anal. Calcd for C$_{31}$H$_{38}$O$_6$ (506.63): C, 73.49; H, 7.56. Found: C, 73.59; H, 7.64.

Example 14

5,5'-[9,9-Bis[2-[2-(2-methoxyethoxy)ethoxy]ethyl]-9H-fluorene-2,7-diyldi-2,1-ethynediyl]bis-2-thiophenecarboxaldehyde

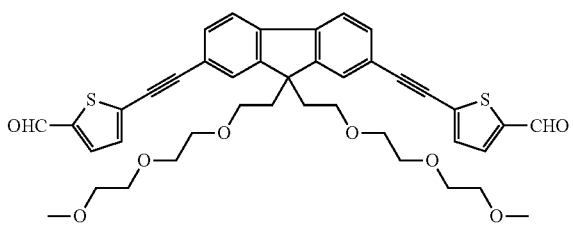 [SMILES: COCCOCCOCCC1(CCOCCOCCOC)c2cc(C#Cc3ccc(C=O)s3)ccc2-c2ccc(C#Cc3ccc(C=O)s3)cc21]

Air was removed from a solution of 2,7-diethynyl-9,9-bis[2-[2-(2-methoxyethoxy)ethoxy]ethyl]-9H-fluorene (0.120 g, 0.237 mmol) in 8.2 mL of toluene and 1.8 mL of Et$_3$N by blowing argon for 20 min. Then Pd(PPh$_3$)$_2$Cl$_2$ (10 mg, 6 mol %) and CuI (2.7 mg, 6 mol %), and 5-iodothiophene-2-carboxaldehyde (0.135 g, 0.568 mmol) were added, and deaeration was continued for 15 min. Thereafter the mixture was stirred at 40° C. for 17 h. After completion of the reaction, reaction mixture was filtered and evaporated to dryness. The crude product was purified by column chromatography on silica gel (CH$_2$Cl$_2$/AcOEt 60:40 then AcOEt) to yield 0.140 g (81%) of 5,5'-[9,9-bis[2-[2-(2-methoxyethoxy)ethoxy]ethyl]-9H-fluorene-2,7-diyldi-2,1-ethynediyl]bis-2-thiophenecarboxaldehyde, mp 84° C.; $^1$H NMR (CDCl$_3$) δ 2.43 (t, 4H, J=7.5 Hz), 2.79 (t, 4H, J=7.2 Hz), 3.21 (m, 4H), 3.33 (s, 6H), 3.39 (m, 4H), 3.54-3.46 (m, 8H), 7.37 (d, 2H, J=3.9 Hz), 7.57 (dd, 2H, J=1.5 Hz, J=7.1 Hz), 7.62 (d, 2H, J=1.2 Hz), 7.71 (d, 2H, J=7.1 Hz), 7.72 (d, 2H, J=3.9 Hz), 9.90 (s, 2H); $^{13}$C NMR (CDCl$_3$) δ 39.6, 51.6, 59.0, 66.8, 70.1, 70.4, 70.5, 71.8, 83.0, 98.5, 120.5, 121.2, 126.6, 131.3, 132.6, 132.8, 136.2, 140.7, 143.9, 149.7, 182.5. HRMS (ESI) calcd for C$_{41}$H$_{42}$O$_8$NaS$_2$ [(M+Na)$^+$] m/z 749.2219. found 749.2226. Anal. Calcd for C$_{41}$H$_{42}$O$_8$S$_2$ (726.90): C, 67.75; H, 5.82; S, 8.82. Found: C, 67.86; H, 5.82; S, 8.63.

Example 15

Photosensitizer 6b (Also Referred in the Present Application as Compound SMU33)

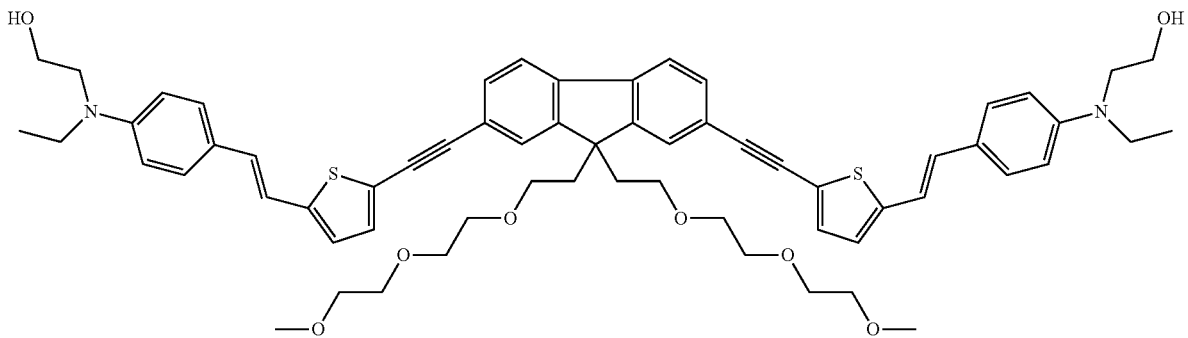 [SMILES: CCN(CCO)c1ccc(/C=C/c2ccc(C#Cc3ccc4c(c3)C(CCOCCOCCOC)(CCOCCOCCOC)c3cc(C#Cc5ccc(/C=C/c6ccc(N(CC)CCO)cc6)s5)ccc3-4)s2)cc1]

To a solution of 5,5'-[9,9-bis[2-[2-(2-methoxyethoxy)ethoxy]ethyl]-9H-fluorene-2,7-diyldi-2,1-ethynediyl]bis-2-thiophenecarboxaldehyde (0.040 g, 0.055 mmol) in anhydrous CH$_2$Cl$_2$ (5 mL), were added tBuOK (18.5 mg, 0.165 mmol) and [[4-[ethyl(2-hydroxyethyl)amino]phenyl]methyl]triphenylphosphonium iodide (0.081 g, 0.143 mmol). The mixture was stirred at 20° C. for 20 h, then diluted with CH$_2$Cl$_2$ (15 mL). The solvent was removed under reduced pressure, and the residue was purified by column chromatography on silica gel. Undesired products were eluted with CH$_2$Cl$_2$/AcOEt (from 90:10 to 0:100), then the desired product was eluted with CH$_2$Cl$_2$/MeOH (95:5), to yield 0.020 g (35%) of 6b; $^1$H NMR (CDCl$_3$) δ 1.19 (t, 6H, J=7.0 Hz), 1.68 (t, 2H, J=5.7 Hz), 2.41 (t, 4H, J=7.3 Hz), 2.79 (t, 4H, J=7.3 Hz), 3.22 (m, 4H), 3.33 (s, 6H), 3.40 (m, 4H), 3.55-3.43 (m, 16H), 3.83 (q, 4H, J=5.7 Hz), 6.74 (d, 4H, J=8.9 Hz), 6.86 (d, 2H, J=15.8 Hz), 6.90 (d, 2H, J=3.6 Hz), 6.99 (d, 2H, J=15.8 Hz), 7.18 (d, 2H, J=3.6 Hz), 7.36 (d, 4H, J=8.9 Hz), 7.51 (dd, 2H, J=7.8 Hz, J=1.4 Hz), 7.57 (m, 2H), 7.65 (d, 2H, J=7.8 Hz); $^{13}$C NMR (CDCl$_3$) δ 12.0, 39.7, 45.6, 51.4, 52.4, 59.0, 60.3, 66.9, 70.0, 70.4, 70.5, 71.9, 84.4, 94.5, 112.5, 117.1, 120.1, 120.2, 122.1, 124.8, 125.0, 126.0, 127.9, 129.6, 130.8, 132.8, 139.9, 145.9, 148.0, 149.4; HRMS (ESI) calcd for C$_{63}$H$_{72}$N$_2$O$_8$S$_2$ (M$^+$·) m/z 1048.4730. found 1048.4742.

The absorption and emission spectra of compound 6b in ethanol (FIG. 12), and the two photon absorption of compound 6b in THF (FIG. 13) are presented.

Photosensitizer 6a and 6b show at the same time good photosensitization efficiency in organic medium (22% quantum yield for singulet oxygen generation in toluene) and an interesting fluorescence for the monitoring and the screening in biological environment (65% quantum yield for fluorescence in ethanol, orange emission). Their two photon absorption characteristics in near infra-red, which have been determined in solution, are very interesting (Two photon absorption cross section superior to 1000 GM at maximum and large spectrum enabling an irradiation ranging from 700 to 900 nm with a good two photon excitation efficiency).

Photophysical Properties of Compounds 6a and 6b in Ethanol

| Compound | $\lambda_{max}^{abs}$ (nm) | $\epsilon_{max}$ ($10^5$ M$^{-1}$cm$^{-1}$) | $\lambda_{max}^{em}$ (nm) | $\Phi$ | $\lambda_{max}^{TPA}$ (nm) | $\sigma_2^{max}$ (GM) |
|---|---|---|---|---|---|---|
| 6a | 432 | 1.04 | 561 | 0.65 | 730 | 1204 |
| 6b | 434 | 0.98 | 575 | 0.33 | 730 | 1530 |

Compounds with a Molecular Clip Group

General Synthesis of Functionalized Compounds

Isocyanatopropyltriethoxysilane (2.2 equiv) and triethylamine as a catalyst, were added to the compounds with a chemically reactive group (1 equiv.) under argon, in dry THF. Freshly distilled THF was added. The reaction mixture was stirred for 2 days at 70° C. End of the reaction was checked by infra-red spectroscopy. The reaction mixture was dried under vacuum, and purified by chromatography on silica gel. Purified compound was dried on MgSO4, filtrated and evaporated to dryness.

Example 16

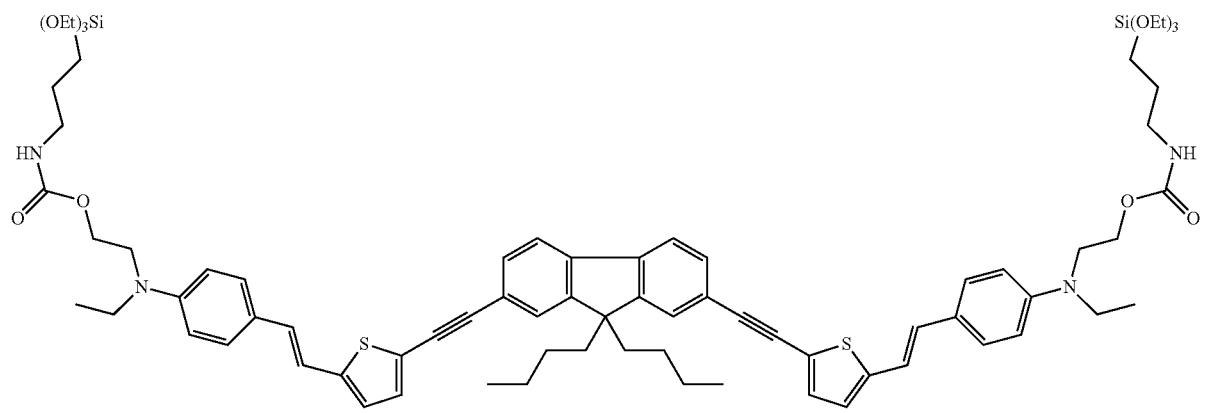

Compound 7a

Photosensitizer 6a (75 mg, 8.4 $10^{-2}$ mmol) was dissolved in freshly distilled THF. Isocyanatopropyltriethoxysilane (2.1 equiv., 1.76 $10^{-1}$ mmol) and a few drops of triethylamine were added. The THF solution was refluxed for 3 days. Reaction mixture was evaporated then purified on silica gel, using an elution mixture CH$_2$Cl$_2$/AcOEt (90/10; rf 0.2). The photosensitizer trialkoxysilane 7a derivative was obtained with a 31% yield.

Example 17

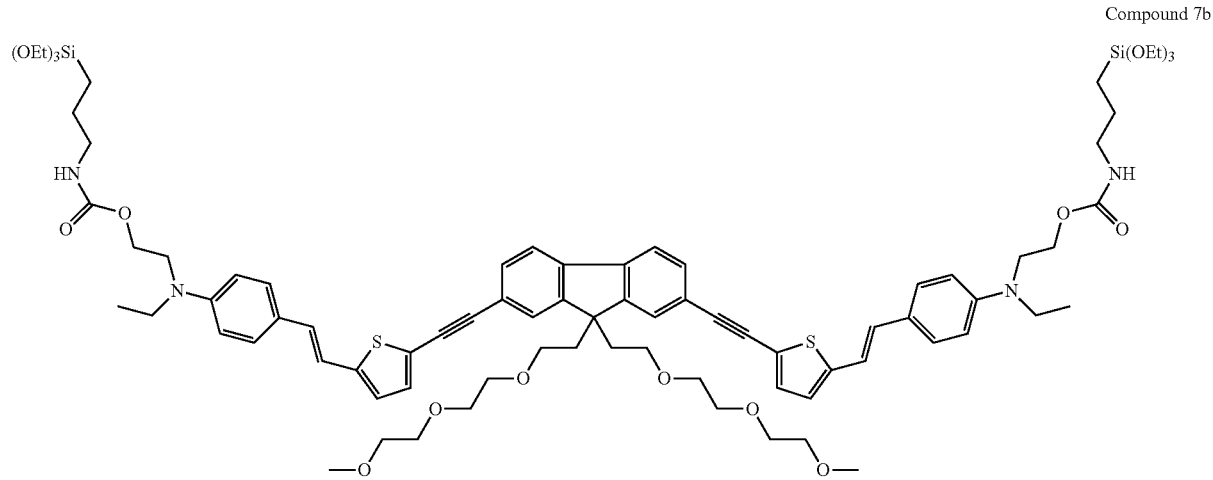

Compound 7b

Reaction vessel was placed under argon atmosphere in presence of photosensitizer 6b (5.9·10$^{-5}$ mol, 62 mg). Freshly distilled THF (5 mL) was added. Then were added isocyanatopropyltriethoxysilane (2.2 equivalent, 1.3 10$^{-4}$ mol) and 3 drops of triethylamine as a catalyst. The reaction mixture was stirred for 2 days at 70° C. The end of the reaction was checked by infra-red spectroscopy. The reaction mixture was dried under vacuum, and purified by chromatography on silica gel eluted by a CH$_2$Cl$_2$/AcOEt mixture (7/3 then 5/5). After drying on MgSO4, filtration and evaporation to dryness, the product was characterized by infra-red, NMR and UV-vis spectroscopy.

Compound 9b

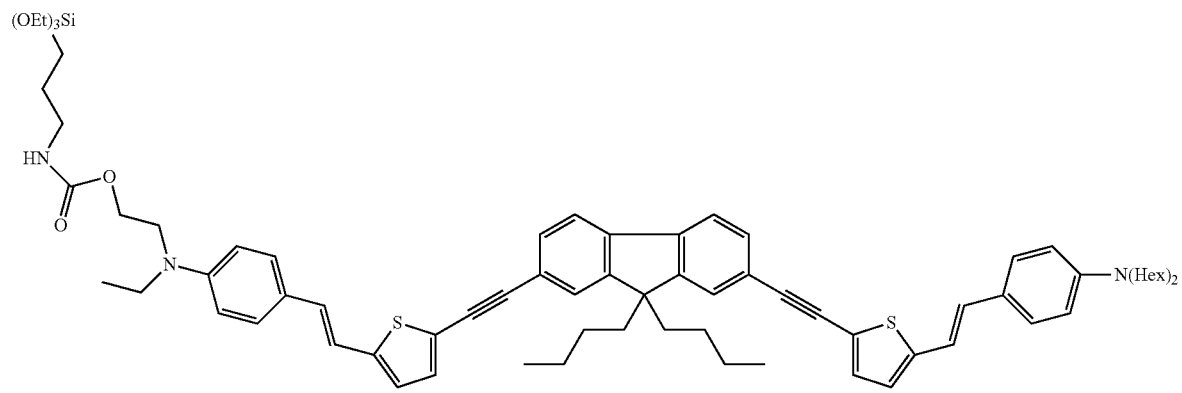

The Photosensitizer 9a (30.3 mg, 3.14 10$^{-2}$ mmol) was dissolved in freshly distilled THF. Isocyanatopropyltriethoxysilane (1.1 equiv., 3.45 10$^{-2}$ mmol) and a few drops of triethylamine were dissolved in 3 ml of THF and was added to the solution. The THF solution was refluxed for 2 days. Reaction mixture was evaporated and use without purification for the next encapsulation step.

B Nanoparticles Synthesis

Nanoparticles without a Biotargeting Moiety

Example 18

Synthesis of Mesoporous Nanoparticles (DB052 and DB060)

The nanoparticles were synthesized by direct micro emulsion (oil in water) in a basic medium.

Cetyltrimethylammonium bromide (CTAB) (686 mg, 1.8 10$^{-3}$ mol) was dissolved in sodium hydroxide (40 mL, 0.2 M) at 25° C. Tetraethoxysilane (3.5 mL, 1.57 10$^{-2}$ mmol) was added dropwise along with an ethanol solution of the previously synthesised photosensitizer trialkoxysilane derivative 7a (4.7 mg for DB052 and 9.2 mg for DB060). After 40 seconds deionized water (260 mL) was added. The solution was stirred for 6 minutes then was quickly neutralised to pH 7 with HCl (0.2 M, about 50 mL). The nanoparticles were recovered through centrifugation (10 minutes, 20000 rotations per minute), stir up in EtOH with ultrasounds, centrifuged. The surfactant was extracted upon treatment with a MeOH/NaCl (285 mL, 1.3% in weight) for 3 hours at room temperature. After centrifugation, the extraction was repeated twice, and then the nanoparticles were washed with water and ethanol.

These nanoparticles are mesoporous with a hexagonal type MCM41 network. The mesoporosity was about 3 nm. The presence of encapsulated photosensitizers is demonstrated by UV-visible absorption (FIG. 14).

The photophysical and two-photon absorption characteristics of the nanoparticles DB052 and DB060 in dispersion in ethanol are reported in Table 1, showing that said nanoparticles keep the encapsulated photosensitizer fluorescence properties and their response to biphotonic excitation in near IR (enabling a deep photosensitisation more efficient).

It is important to note that an important feature of the present invention is the covalent grafting of the photosensitizer to the nanoparticle that avoids photosensitizer leaching from the nanoparticle.

TABLE 1

| Nanoparticle | $\lambda_{abs}^{max}$ (nm) | $\lambda_{em}^{abs}$ (nm) | $\Phi_F{}^a$ | $\sigma_2^{max}$ (GM)$^b$ |
|---|---|---|---|---|
| DB052 | 432 | 542 | 0.36 | 1120 |
| DB060 | 432 | 547 | 0.30 | 1140 |

$^a$ Fluorescence quantum yield.

$^b$ Two-photon efficient absorption cross section per photosensitizer. The nanoparticle response corresponds to the sum of the contribution of the photosensitizers encapsulated in each nanoparticle.

Nanoparticles with a Biotargeting Moiety

A further step in the synthesis of nanoparticles encapsulating photosensitizers is the functionalization of said nanoparticle surface by a biomolecule enabling the biotargeting of cancer cells. Several organic coupling agents were used for this surface grafting. Organic coupling agents contain a chloro or alkoxysilane function for anchoring on silica, and an amine, thiol, alcohol, hydrazine, semicarbazide, isocyanate, acid or aldehyde function for bonding to the biomolecule.

The biomolecules used for the functionalization of the nanoparticles surface can be of different type, for example mannose, galactose, rhamnose, mannose 6-phosphate, mannose 6-phosphate analogs.

The nanoparticle surface was functionalized by a trialkoxysilane comprising one amine function (for example aminopropyltriethoxysilane or aminopropyltrimethoxysilane). The surface amine functions react with a α-mannose phenylaminocyclobutenedione derivative. Mannose proportioning was monitored by UV-Vis absorption after reaction with a resorcinol/H$_2$SO$_4$ solution (dosage metric assay).

Example 19

Aminopropyltriethoxysilane (APTS) Grafting on Nanoparticles Surface

Nanoparticles DB052 or DB060 (350 mg) were suspended by ultrasounds in deionised water (10 mL). APTS (500 μL) was added dropwise. HCl (0.2 M) was added until pH 6.5. The reaction was stirred for 18 hours, centrifuged (10 minutes, 20000 rotations per minute). The nanoparticles were washed twice with water and three times with ethanol (ultrasounds and centrifuged). The nanoparticles were isolated (350 mg).

Amine functions were characterized by a quantitative assay with ninhydrin. UV-vis absorption spectrum observed in ethanol showed that photosensitizer were still present and had not been spoilt during the synthesis.

Example 20

α-mannose Surface Grafting on Nanoparticles (DB069)

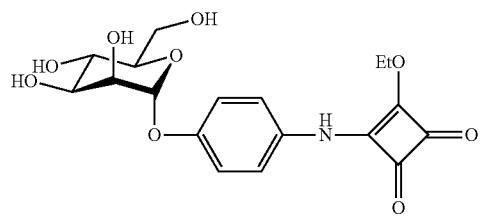

α-mannose phenylaminocyclobutenedione derivative

Nanoparticles DB052 (200 mg) were stirred up by ultrasounds for 30 minutes in ethanol (5 mL). α-mannose phenylaminocyclobutenedione derivatives (71 mg, 1.8 $10^{-4}$ mol, structure here above) was dissolved in an ethanol/water mixture (10 ml, 3/2). The α-mannose phenylaminocyclobutenedione derivative solution was added dropwisely to the nanoparticle suspension. Triethylamine (500 μL) was added, and the suspension was stirred for 18 hours. After centrifugation, the nanoparticles were dispersed in water and centrifuged (3 cycles), then dispersed in ethanol and centrifugated (two cycles). Functionalized nanoparticles (DB069) were obtained (200 mg).

Example 21

α-mannose Surface Grafting on Nanoparticles (DB103)

α-mannose phenylaminocyclobutenedione (250 mg; 0.37 mmol) was dissolved in a mixture of Ethanol/$H_2O$ (3/2) (10 mL) and triethyamine (400 μL) was added dropwise to the solution of APTS (Aminopropyltriethoxysilane) grafted nanoparticles DB060 (250 mg in 10 ml of EtOH). The mixture was stirred during 16 h. The nanoparticles were then centrifugated and washed with water and ethanol and dried under vacuum to afford 232 mg of grafted nanoparticles. The concentration of α-mannose phenylaminocyclobutenedione grafted on the surface of the DB103 nanoaprticle is 0.089 mmol/g.

The characteristics (size, porosity, concentration of photosensitizer and biotargeting molecules) of the nanoparticles encapsulating biphotonic photosensitizers have been measured. The data are presented in table 2.

TABLE 2

| | Concentration (μmol per g of nanoparticle) | | | Porosity | Size |
|---|---|---|---|---|---|
| | Photosensitizer 7a | Mannose | Cyclobutadienedione | $S_{BET}$ ($m^2/g$) | D (nm) |
| DB052 | 2.9 | — | — | 874 | 3 |
| DB060 | 4.5 | — | — | 997 | 2.6 |
| DB069 | 2.9 | 0.532 | 0.532 | 607 | 2.6 |
| DB103 | 4.5 | 0.089 | 0.089 | Not measured | Not measured |

The large excess of phenylaminocyclobutenedione moieties grafted on the surface of the particles, with respect to the number of internal photosensitizers induces a screening effect on photosensitization (due to the strong absorption of the phenylaminocyclobutenedione function in the near UV and visible wavelengths).

This strong screening effect is not relevant for biphotonic excitation since the two-photon absorption cross section of phenylaminocyclobutenedione in near infrared is very weak.

Nanoparticles Encapsulating a Antineoplastic Agent

Example 22

Loading of Camptothecin (CPT)

Mannose derivatives coated nanoparticles (50 mg) were dispersed in DMSO (3 mL) containing CPT (5 mg). The suspension was stirred at room temperature for 24 h. After centrifugation, the nanoparticles were washed twice with water and dried under vacuum.

Determination the amount of CPT loaded in the nanoparticle.

Camptothectin loaded nanoparticles (4 mg) were suspended and sonicated with DMSO (5 mL), the suspension was centrifuged and the UV-visible spectrum of the supernatant solution containing the releasing CPT molecules was measured. It was determined that 12 μmol of CPT were loaded per gram of nanoparticles.

C Biological Results

The photodynamic activity of differents nanoparticles functionalized or not with a biomolecule, and a shielding moities, was investigated in several cancer cell lines. The cytotoxic efficiency of nanoparticles endocytosed in cancer cell lines was induced by a two photon irradiation of photosensibilisators (PS) encapsulated in nanoparticles. PDT therapeutic interest was also shown by the absence of cytotoxicity of these nanoparticles without laser irradiation. The specific targeting and active endocytosis of these nanoparticles had been already described and demonstrated in a previous patent (08/05034) by the co-incubation of the surface functionalized nanoparticles and the corresponding biomolecule.

Cell lines are all available in the American Type Culture Collection (ATCC) and cultured in a medium constituted according to the recommendations of ATCC.

In Vitro

The nanoparticles DB052 (devoid of shielding or biotargeting moieties grafted on their surface) and nanoparticles DB069 (grafted with phenylaminocyclobutenedione and mannose on their surface) have been tested in biphotonic photodynamic therapy on MDA-MB-231 breast cancer (Maynadier M, Ramirez J M, Cathiard A M, Platet N, Gras D, Gleizes M, Sheikh M S, Nirde P, Garcia M. Unliganded estrogen receptor alpha inhibits breast cancer cell growth through interaction with a cyclin-dependent kinase inhibitor (p21(WAF1)). *FASEB J.* 2008 March; 22(3):671-81. Epub 2007 Oct. 2). The comparison between irradiated cells (at 770 nm) and non-irradiated cells demonstrates on one hand the absence of cytotoxicity of the nanoparticles when untreated by biphotonic irradiations and also under natural light, and on the other hand the strong cytotoxicity under biphotonic irradiation, said cytotoxicity being enhanced by the presence of a biotargeting (or biomolecule) moiety.

These tests demonstrate the high efficiency of the two-way functionalized nanoparticles (encapsulated biphotonic photosensitizer, and grafted by biotargeting and shielding moieties) for two-photon photodynamic therapy.

Moreover, it is important to note that in the nanoparticles according to the present invention, the photosensitizer is not excitable by one-photon visible irradiation (i.e. natural light) because of the shielding effect of the moieties grafted on the nanoparticle surface. This characteristic is particularly important when considering the therapeutical protocol because it should enable the patient to get rid of sensitization issues during the pre-treatment (between injection and irradiation) and/or post-treatment (elimination) which compels the patient to remain in darkness.

This effect is an important improvement of the treatment protocol.

Example 23

Figure 1A:
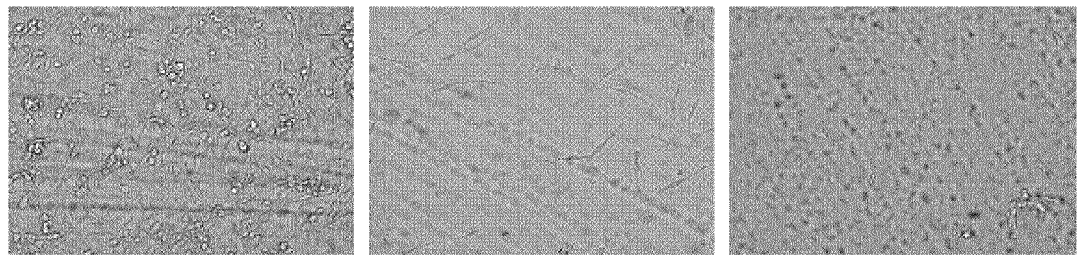
Figure 1B:
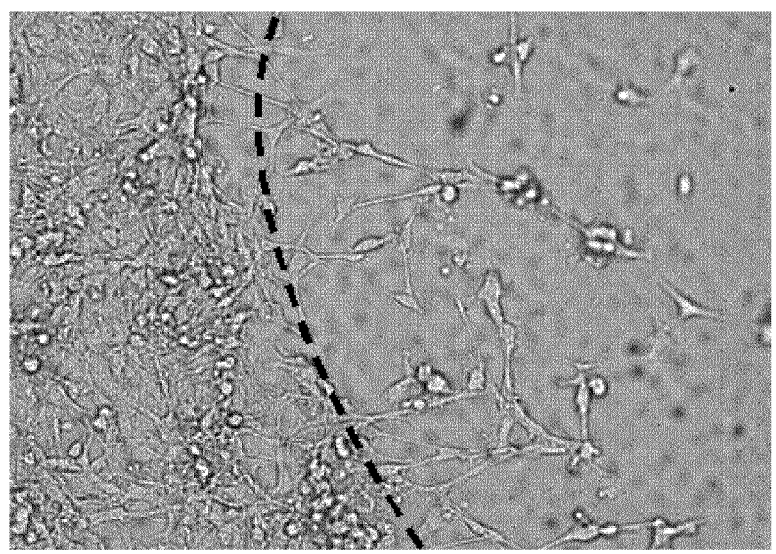

PDT efficiency of Nanoparticles DB052 (MSN (Mesoporous Silica Nanoparticles)) and DB069 (MSN-mannose) on MDA-MD-231 Breast Cancer Cell Line in 24 h Incubation (FIGS. 1A, 1B)

MDA-MB-231 cells were maintained in Dulbecco's modified Eagle's medium (DMEM) added with 10% fetal bovin serum (FBS) (MDA-MB-231 usual medium, in wet atmosphere at 37° C. and 5% $CO_2$. For the experiment, cells were plated in a 384 multiwell glass bottom (0.17 mm) with a black polystyrene frame, at the density of 700 cells/well in 70 µl medium. MDA-MB-231 cancer cells were incubated 24 h with 20 µg/ml of nanoparticles. Then medium was removed, cells were washed and maintain in usual medium.

Two-photon irradiation was performed on a confocal microscope equipped with a mode-locked Ti:sapphire laser generating 100 fs wide pulses at a 80 MHz rate. The laser beam is focused by a microscope objective lens (10×, NA 0.4). Cells were submitted to two-photon irradiation at 760 nm consisting in 3 scans of 1 s each. Scanned areas were 1.5×1.5 mm$^2$ at the 4 quarts of the well in order to irradiate the totality of the well. The average power delivered to the sample was measured with a thermoelectric optical energy meter and was 80 mW. Two days after two photon irradiation, the percentage of living cells was determined by the MTS enzymatic assay (Cell Titer 96, G3580, Promega).

FIGS. 1A and 1B show microscope pictures of MDA-MB-231 cells incubated with (or without) MSN or MSN-mannose for 24 hours and treated by two photon irradiation.

FIGS. 1A and 1B demonstrate the specificity of the photodynamic therapy with the particles according to the present invention. Cells death is observed and occurs in the irradiated area when the cells have been incubated with nanoparticles according to the present invention.

Therapeutical efficiency is improved by mannose coating of the nanoparticles surface. Moreover, the absence of toxicity of the unirradiated nanoparticles demonstrates the specificity of the photodynamic therapy with the compounds according to the present invention.

Example 24

Figure 2A:
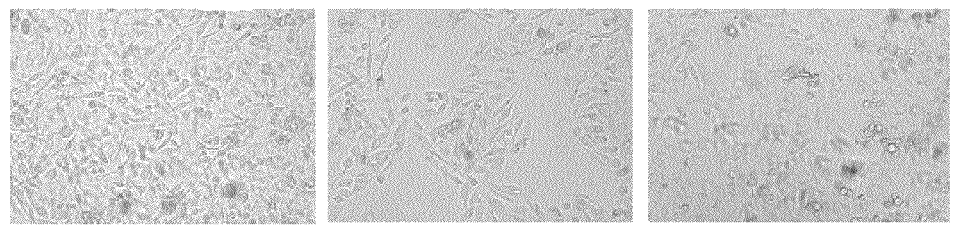
FIG. 2A shows a decrease in cell density, when a sample is treated by biphotonic irradiation, and incubated with nanoparticles according to the present invention.
Figure 2B:
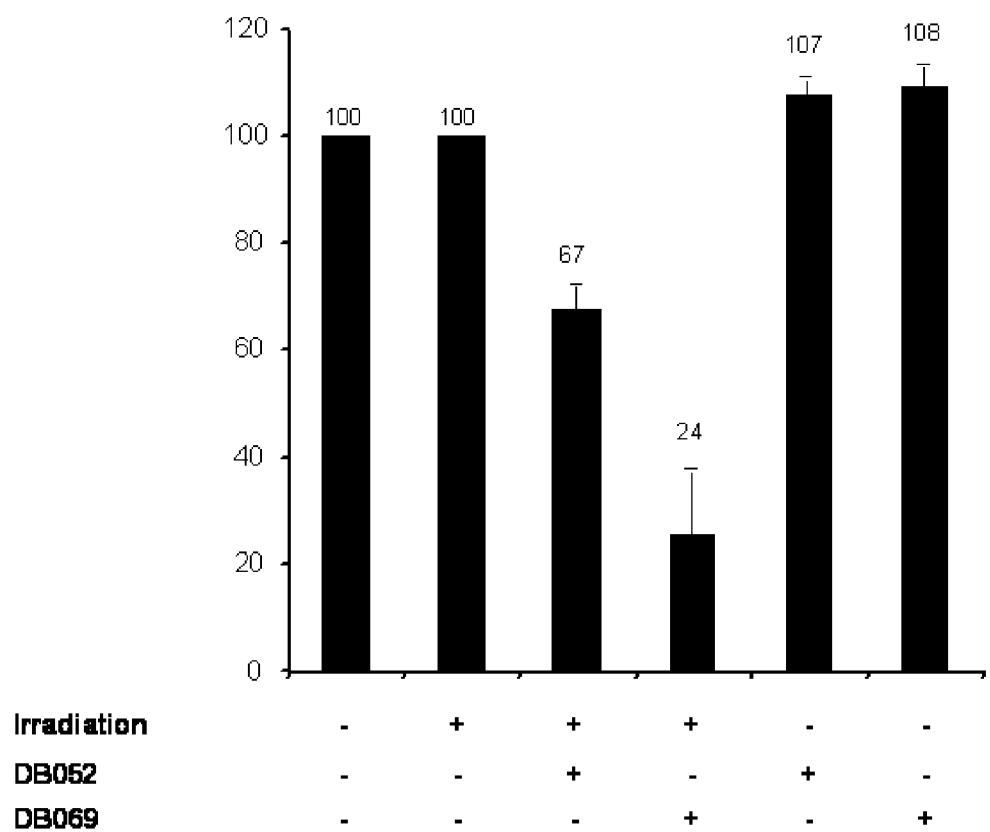
FIG. 2B represents a histogram indicating the percentage of living cells with respect to a control experiment of untreated cells (no nanoparticles and no irradiations).

PDT Efficiency of Nanoparticles DB052 (MSN) and DB069 (MSN-mannose) on MDA-MD-231 Breast Cancer Cell Line in 4 h Incubation (FIGS. 2A and 2B)

The conditions were the same as these of Example 21 and only differ on incubation time. In this example, the incubation time was 4 h.

A decrease in cell density was observed in the samples treated by biphotonic irradiation and incubated with nanoparticles according to the present invention (FIG. 2A).

The efficiency of the photodynamic treatment (FIG. 2B) was demonstrated by the death of 33% of the cells incubated with nanoparticles DB052, and by the death of 76% of the cells incubated with DB069. The therapeutical efficiency was improved by mannose coating of the nanoparticle surface.

Moreover, the absence of toxicity of the unirradiated nanoparticles demonstrates the specificity of the photodynamic therapy with the compounds according to the present invention.

Example 25

PDT Efficiency of Nanoparticles DB052 (MSN) and DB069 (MSN-mannose) on MCF7 Breast Cancer Cell Line in 2 h and 4 h Incubation (FIGS. 3A, 3B, 4A and 4B)

MCF7 cells (Maynadier M, Ramirez J M, Cathiard A M, Platet N, Gras D, Gleizes M, Sheikh M S, Nirde P, Garcia M. Unliganded estrogen receptor alpha inhibits breast cancer cell growth through interaction with a cyclin-dependent kinase inhibitor (p21(WAF1)). *FASEB J.* 2008 March; 22(3):671-81. Epub 2007 Oct. 2.) were maintained in F-12 Dulbecco's modified Eagle's medium (F-12 DMEM) added with 10% FBS (MCF7 usual medium), in wet atmosphere at 37° C. and 5% CO2. For the experiment, cells were plated in a 384 multiwell glass bottom (0.17 mm) with a black polystyrene frame, at the density of 2000 cells/well in 70 µl medium. MCF7 cancer cells were incubated 2 h or 4 h with 20 µg/ml of nanoparticles. Then medium was removed, cells were washed and maintain in usual medium.

Two-photon irradiation was performed on a confocal microscope equipped with a mode-locked Ti:sapphire laser generating 100 fs wide pulses at a 80 MHz rate. The laser beam is focused by a microscope objective lens (10×, NA 0.4). Cells were submitted to two-photon irradiation at 760 nm consisting in 3 scans of 1 s each. Scanned areas were 1.5×1.5 mm$^2$ at the 4 quarts of the well in order to irradiate the totality of the well. The average power delivered to the sample was measured with a thermoelectric optical energy meter and was 80 mW. Two days after two photon irradiation, the percentage of living cells was determined by the MTS enzymatic assay (Cell Titer 96, G3580, Promega).

Cell death was induced by photodynamic therapy with nanoparticles according to the present invention.

Two Hour Incubation

Incubation and irradiation with compounds according to the present invention induce cellular death (FIG. 3A)

The efficiency of the therapy is demonstrated by the death of 31% of the cells irradiated and incubated with nanoparticles DB052, and the death of 46% of the cells irradiated and incubated with nanoparticles DB069, after 2 hours of incubation with the said nanoparticles (FIG. 3B).

Four Hour Incubation

Incubation and irradiation with compounds according to the present invention induce cellular death (FIG. 4A)

The efficiency of the therapy is demonstrated by the death of 36% of the cells irradiated and incubated with nanoparticles DB052, and the death of 56% of the cells irradiated and incubated with nanoparticles DB069, after 4 hours of incubation with the said nanoparticles (FIG. 4B).

FIGS. 4A, 4B, 5A and 5B demonstrate an increase in the therapeutical efficiency of nanoparticle surface coated with mannose.

Moreover, unpresented results obtained with cells incubated with nanoparticles but untreated by two photon irradiations show an absence of toxicity.

Example 26

Kinetic Effect of Nanoparticles DB069 (MSN-mannose) on MCF7 Breast Cancer Cell Line (FIG. 5)

The conditions were the same as those of Example 23 and only differed on incubation time. In this example, incubation times with DB069 were 2 h, 4 h and 24 h, induced cell death were respectively of 46%, 56% and 100% (FIG. 5).

This example demonstrates that the efficiency of the photodynamic therapy increases with the incubation time of the cells with the nanoparticles according to the present invention.

Example 27

PDT Efficiency of Nanoparticles DB052 (MSN) and DB069 (MSN-mannose) on Y-79 Retinoblastoma Cell Line in 24 h Incubation (FIG. 6)

Y-79 cells (Laville I, Pigaglio S, Blais J C, Doz F, Loock B, Maillard P, Grierson D S, Blais J. Photodynamic efficiency of diethylene glycol-linked glycoconjugated porphyrins in human retinoblastoma cells. *J Med. Chem.* 2006 Apr. 20; 49(8):2558-67) are non adherent cells which were maintained in Roswell Park Memorial Institute culture medium (RPMI 1640) added with 20% FBS (Y-79 usual medium), in wet atmosphere at 37° C. and 5% $CO_2$. For the experiment, cells were plated in a 384 multiwell glass bottom (0.17 mm) with a black polystyrene frame, at the density of 2000 cells/well in 70 µl medium. Y-79 retinoblastoma cells were incubated 24 h with 20 µg/ml of nanoparticles.

Two-photon irradiation was performed on a confocal microscope equipped with a mode-locked Ti:sapphire laser generating 100 fs wide pulses at a 80 MHz rate. The laser beam is focused by a microscope objective lens (10×, NA 0.4). Cells were submitted to two-photon irradiation at 760 nm consisting in 3 scans of 1 s each. Scanned areas were 1.5×1.5 $mm^2$ at the 4 quarts of the well in order to irradiate the totality of the well. The average power delivered to the sample was measured with a thermoelectric optical energy meter and was 80 mW. Two days after two photon irradiation, the percentage of living cells was determined by the MTS enzymatic assay (from Promega).

DB052 and DB069 nanoparticles induced respectively 30% and 67% cytotoxicity over Y-79 retinoblastoma cell line (FIG. 6).

These results show an increased efficiency for mannose coated nanoparticles (DB069).

Example 28

PDT Efficiency of Nanoparticles DB052 (MSN), DB060 (MSN), DB069 (MSN-mannose) and DB103 (MSN-mannose) on HCT-116 Colon Cancer Cell Line in 4 h Incubation (FIGS. 7A, 7B, 7C, 7D, 7E)

HCT-116 cells (Zhan Y, Ginanni N, Tota M R, Wu M, Bays N R, Richon V M, Kohl N E, Bachman E S, Strack P R, Krauss S. Control of cell growth and survival by enzymes of the fatty acid synthesis pathway in HCT-116 colon cancer cells. *Clin Cancer Res.* 2008 Sep. 15; 14(18):5735-42.) were maintained in Mac Coy culture medium added with 10% FBS (HCT-116 usual medium), in wet atmosphere at 37° C. and 5% $CO_2$. For the experiment, cells were plated in a 384 multiwell glass bottom (0.17 mm) with a black polystyrene frame, at the density of 2000 cells/well in 70 µl medium. HCT-116 cells were incubated 4 h with 20 µg/ml of nanoparticles functionalized (DB069 (FIG. 7C), DB103 (FIG. 7E)) or not (DB052 (FIG. 7B), DB060 (FIG. 7D)) with mannose. DB060 and DB103 were characterized by a higher quantity of two photon PS than this of DB052 and DB069. Two-photon irradiation was performed on a confocal microscope equipped with a mode-locked Ti:sapphire laser generating 100 fs wide pulses at a 80 MHz rate. The laser beam is focused by a microscope objective lens (10×, NA 0.4). Cells were submitted to two-photon irradiation at 760 nm consisting in 3 scans of 1 s each. Scanned areas were 1.5×1.5 $mm^2$ at the 4 quarts of the well in order to irradiate the totality of the well. The average power delivered to the sample was measured with a thermoelectric optical energy meter and was 80 mW. Results were monitored through direct observation with a microscope.

FIGS. 7A to 7E are microscope pictures of HCT-116 cells according to example 26, FIG. 7A shows the control cells.

FIGS. 7A to 7E show an improved therapeutical efficiency of the nanoparticles containing a larger amount of photosensitizer, and an improved therapeutical efficiency of the mannose coated nanoparticles. Biphotonic irradiation without nanoparticles does not induce cells death.

Example 29

Cytotoxic Effect Study of Daylight Exposition of Culture Cells Incubated with DB052 or DB069

For cell culture, MDA-MB-231 and MCF-7 human breast cancer cells (ATCC) were routinely cultured in Dulbecco's modified Eagle's medium (DMEM) supplemented with 10% fetal bovine serum and 50 µg $mL^{-1}$ gentamycin. HCT-116 human colorectal cancer cells (ATCC) were routinely cultured in Mac Coy's culture medium supplemented with 10% fetal bovine serum and 50 µg $mL^{-1}$ gentamycin. All these cell types were allowed to grow in humidified atmosphere at 37° C. under 5% CO2. For experiments of cytotoxic effect of daylight exposition, cells were seeded into 96-well plates at $3 \cdot 10^4$ cells/well in 100 µl of culture medium and allowed to grow for 24 h. Cells were then incubated 4 h with 20 µg $mL^{-1}$ of DB052 or DB069. After incubation with MSN, cells were washed, maintained in fresh culture medium and then submitted or not to daylight exposition during 1 h. Two days after irradiation, a 3-(4,5-dimethylthiazol-2-yl)-2,5-diphenyltetrazolium bromide; Promega (MTT) assay was performed to evaluate the cytotoxicity of MSN. Briefly, cells were incubated in the presence of 0.5 mg $mL^{-1}$ MTT during 4 h to determine mitochondrial enzyme activity. Then MTT precipitates were dissolved in 150 μl ethanol/DMSO (1:1) solution and absorbance was read at 540 nm. The data are shown in table 3.

TABLE 3

| Living cells (%) | Daylight exposition | | | No light exposition | | |
|---|---|---|---|---|---|---|
| | MCF-7 | MDA-MB-231 | HCT-116 | MCF-7 | MDA-MB-231 | HCT-116 |
| Control | 100 ± 3 | 100 ± 5 | 100 ± 9 | 100 ± 6 | 100 ± 4 | 100 ± 6 |
| DB052 | 107 ± 5 | 108 ± 4 | 98 ± 10 | 97 ± 7 | 105 ± 10 | 99 ± 2 |
| DB069 | 96 ± 3 | 105 ± 10 | 99 ± 8 | 98 ± 8 | 101 ± 8 | 98 ± 3 |

In Vivo

Photodynamic activity of DB069 nanoparticles was investigated on subcutaneous tumors of mice.

Example 30

PDT Efficiency of Nanoparticles DB069 (MSN-mannose) on Nude Mice Tumors from HCT-116 Xenografts (FIGS. 8 and 9)

J0: nude mice (Swiss) were xenografted by a sub cutaneous injection of 100 μl of a monocellular suspension containing 10,000,000 HCT-116 cells and a reconstituted extracellular matrix (Matrigel 5 mg/ml).

J15: tumours were measured and homogenous groups were constituted.

J18: mice were treated by intravenous injection of 200 μl of physiological serum added or not (control) with nanoparticles (2 mg/ml). Three hours after injection, mice were anesthetised and tumors were submitted to two photon irradiation at 760 nm during 3×3 min at 3 different areas of the tumour.

J21-J45: Tumours were measured (L×l×h) and their volumes were determined by the formula: (L×l×h)×0.52.

J45: mice were sacrificed and tumours were collected and measured.

FIG. 8 shows the results for tumours having a starting volume comprised between 0.009 and 0.01 cm³. FIG. 8 demonstrates that tumors react strongly to photodynamic therapy with nanoparticles according to the present invention.

FIG. 9 shows the results for tumours having a starting volume comprised between 0.02 and 0.04 cm³. FIG. 9 demonstrates that tumors react to photodynamic therapy with nanoparticles according to the present invention.

Example 31

Administration of a Pharmaceutical Composition of a Nanoparticle

An infusion of physiological serum added with the nanoparticles of the invention (at the dose of 20 mg/kg) is administered to patients.

Between 2 and 24 h after the end of the injection, the tumour area is irradiated during to 60 min at the wavelength determined for biphotonic excitation.

This experiment is repeated one or several times according to the regression of the tumour.

The invention claimed is:

1. A compound of formula (I):

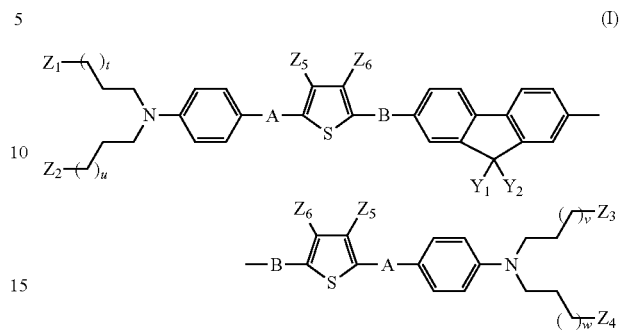

wherein
the groups A and B represent independently from each other —CH═CH—, or —C≡C—,
the terms t, u, v, and w represent, independently from each other, values ranging from 0 to 9,
the groups $Y_1$ and $Y_2$ represent independently from each other:
 a hydrogen atom, or
 an alkyl group linear, branched or substituted, carrying from 1 to 9 carbon atoms, or
 a polyethylene glycol chain of formula: —$(CH_2)_n$—O—$(CH_2CH_2O)_m CH_3$, wherein n<4 and m varies from 1 to 6, or
 an ammonium group of formula: —$(CH_2)_p$—$NR_3^+X^-$, wherein $X^-$ is selected from the group consisting of halogens, tosylate, sulphate, phosphate, $NTf_2$, and $PF_6$ anions, p varies from 1 to 6, and R is an alkyl chain linear or branched, from 1 to 9 carbon atoms,
the groups $Z_1$, $Z_2$, $Z_3$, and $Z_4$ represent independently from each other:
 a hydrogen atom, or
 a group W, said group W being a chemically reactive group, or
 a group V, said group V being a molecular clip constituted by -α-β-δ, wherein:
  α is a functional linking group, and
  β is an alkyl chain, linear or branched, containing from 1 to 9 carbon atoms, and
  δ is a $Si(OR')_3$ group, wherein R' is an alkyl chain, linear or branched, from 1 to 9 carbon atoms, or
 an aryl, aryloxy, aralkyl, aralkyloxy, heteroaryl, or heteroaryloxy group, ranging from 1 to 10 carbon atoms, containing said chemically reactive group W, or
 an alkyl chain optionally unsaturated, linear, branched or substituted, ranging from 1 to 10 carbon atoms, or
 an alkyl chain optionally unsaturated, linear, branched or substituted, ranging from 1 to 10 carbon atoms, and containing said chemically reactive group W, or
 a polyethylene glycol chain of formula —$(CH_2)_q$—O—$(CH_2CH_2O)_r$—$CH_2CH_2$—W, wherein q<4 and r varies from 1 to 6, and W is said chemically reactive group,
provided at least one of the $Z_1$, $Z_2$, $Z_3$ or $Z_4$ groups represents:
 said chemically reactive group W, or
 said group V being a molecular clip constituted by -α-β-δ, wherein:
  α is a functional linking group, and β is an alkyl chain, linear or branched, containing from 1 to 9 carbon atoms, and δ is a Si(OR')₃ group, wherein R' is an alkyl chain, linear or branched, from 1 to 9 carbon atoms, or an aryl, aryloxy, aralkyl, aralkyloxy, heteroaryl, or heteroaryloxy group, ranging from 1 to 10 carbon atoms, containing said chemically reactive group W, or an alkyl chain optionally unsaturated, linear, branched or substituted, ranging from 1 to 10 carbon atoms, and containing said chemically reactive group W, or a polyethylene glycol chain of formula —(CH$_2$)$_q$—O—(CH$_2$CH$_2$O)$_r$—CH$_2$CH$_2$—W, wherein q<4 and r varies from 1 to 6, and W is said chemically reactive chemically reactive group, the groups Z$_5$ and Z$_6$ represent independently from each other:

a hydrogen atom, or an alkyl chain optionally unsaturated, linear, branched or substituted, ranging from 1 to 9 carbon atoms, or an alkoxy group, a carbocyclic group, a heterocyclic group, or an aromatic group, ranging from 1 to 9 carbon atoms, or Z$_5$ and Z$_6$ are linked together through an ethylene glycol group, thus providing a 3,4-ethylenedioxythiophene group (EDOT) with the thiophene group they are linked to,

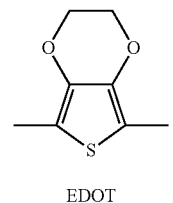

EDOT

2. The compound according to claim 1, of formula (IV):

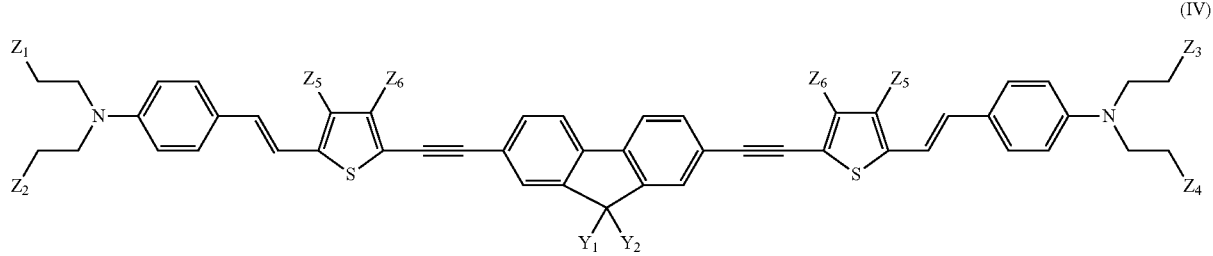

(IV)

wherein Z$_1$, Z$_2$, Z$_3$, Z$_4$, Z$_5$, Z$_6$, Y$_1$, Y$_2$ and B groups are as defined above.

3. The compound according to claim 1, of a formula selected from the group consisting of:

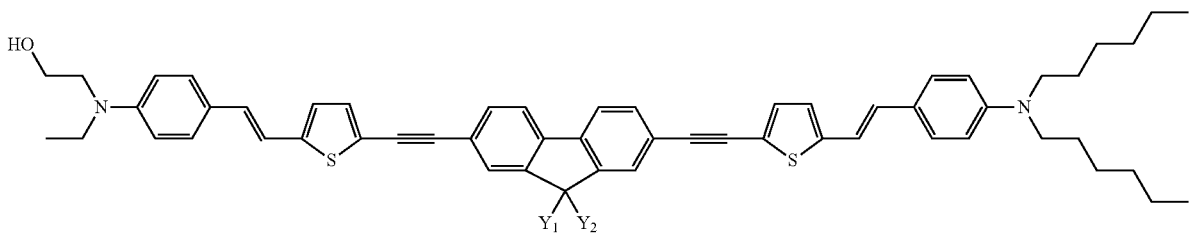

wherein Y$_1$ and Y$_2$ are similar and represent
n-butyl alkyl chain, or
—(CH$_2$CH$_2$)O(CH$_2$CH$_2$)O(CH$_2$CH$_2$)OCH$_3$ groups,

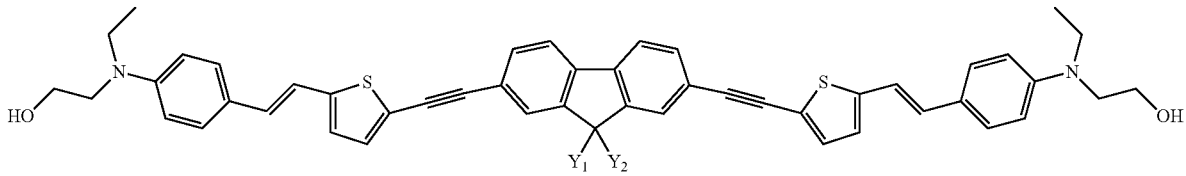

wherein $Y_1$ and $Y_2$ are similar and represent
n-butyl alkyl chain, or
—$(CH_2CH_2)O(CH_2CH_2)O(CH_2CH_2)OCH_3$ groups,
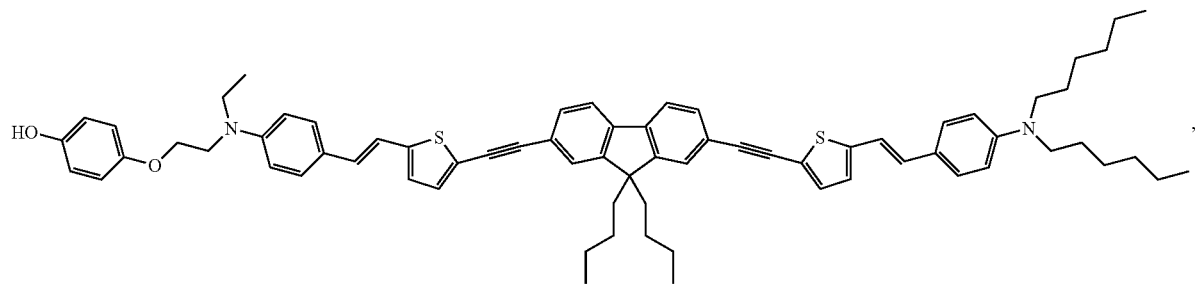
and
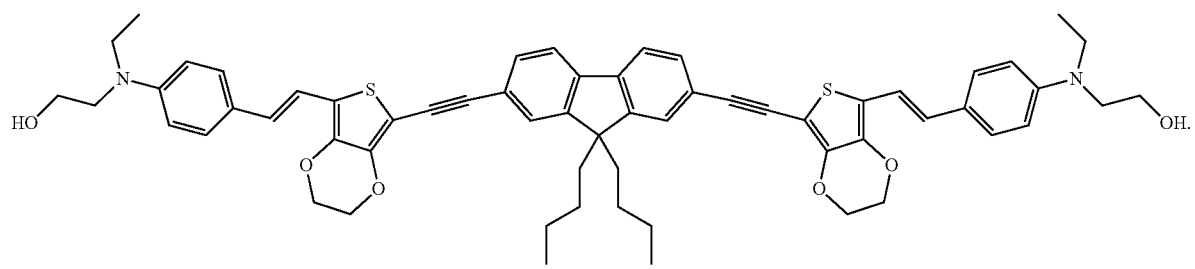
4. The compound according to claim 1, of a formula selected from the group consisting of:
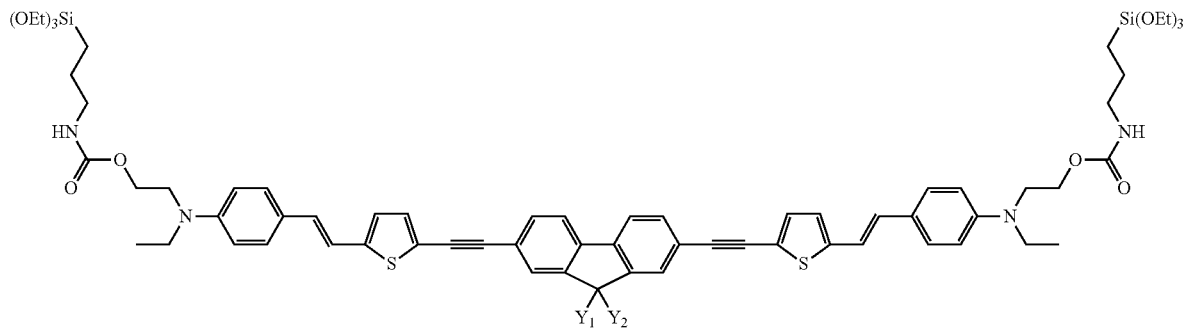
wherein $Y_1$ and $Y_2$ are similar and represent —$(CH_2CH_2)$ $O((CH_2CH_2)O_2CH_3$ groups,
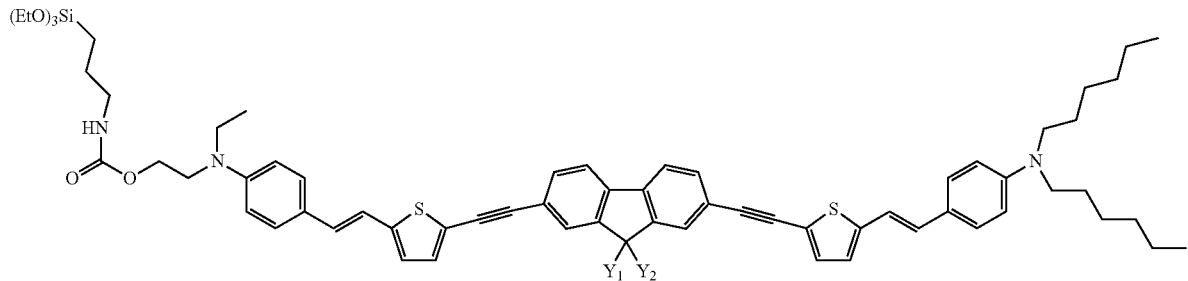
wherein $Y_1$ and $Y_2$ are similar and represent —$(CH_2CH_2)$ $O((CH_2CH_2)O)_2CH_3$ groups,

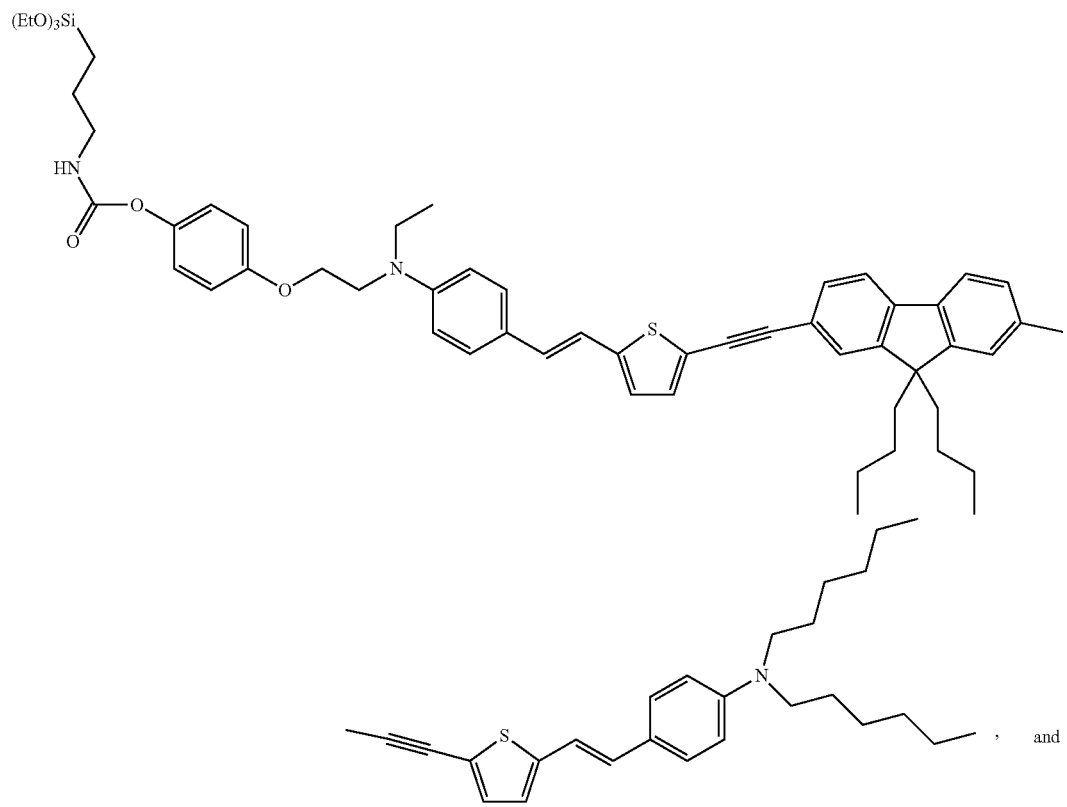

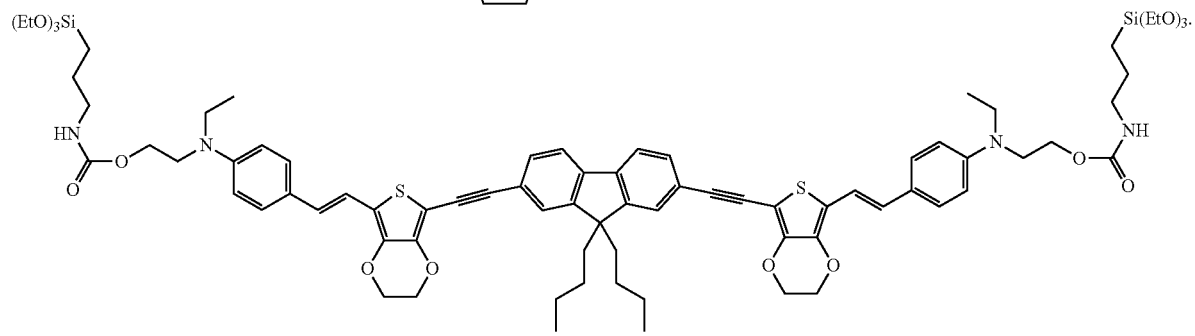

5. A silica nanoparticle, comprising at least one photosensitizer constituted by at least a compound according to claim 1, covalently linked to said nanoparticle, and optionally comprising shielding moieties grafted on the surface of said nanoparticle, and optionally comprising biotargeting moieties grafted on the surface of said nanoparticle.

6. A silica nanoparticle composition, comprising:
   at least one silica nanoparticle comprising at least one photosensitizer constituted by at least a compound according claim 1, covalently linked to said nanoparticle, and optionally comprising shielding moieties grafted on the surface of said nanoparticle, and optionally comprising biotargeting moieties grafted on the surface of said nanoparticle.

7. The silica nanoparticle composition according to claim 6, wherein said silica nanoparticle has an organized porosity.

8. The silica nanoparticle composition according to claim 6, wherein said silica nanoparticle is mesoporous.

9. The silica nanoparticle composition according to claim 6, comprising biotargeting moieties grafted on the surface of said nanoparticle which specifically target neoplastic tissues.

10. The silica nanoparticle composition according to claim 6, comprising shielding moieties grafted on the surface of said nanoparticle, and which specifically absorb radiations in the 190 to 600 nm range wavelengths.

11. The silica nanoparticle composition according to claim 6, wherein the concentration of said photosensitizer, with respect to the total mass of the nanoparticle comprising said photosensitizer, ranges from about 0.1 micromole per gram to about 100 micromoles per gram.

12. The silica nanoparticle composition according to claim 6, wherein the concentration of the biotargeting moieties grafted on the surface of the said nanoparticle, ranges from about 1 μmol per gram to about 2 mmol per gram.

13. A pharmaceutical composition comprising:
   (i) at least one of the compounds according to claim 1, or
   (ii) at least one silica nanoparticle composition comprising at least one silica nanoparticle comprising at least one photosensitizer constituted by said at least one of the compounds, covalently linked to said nanoparticle, and optionally comprising shielding moieties grafted on the surface of said nanoparticle, and optionally comprising biotargeting moieties grafted on the surface of said nanoparticle, and
   a pharmaceutically acceptable carrier.

14. The pharmaceutical composition according to claim 13, comprising:
   (i) at least one of the compounds selected from the group consisting of:
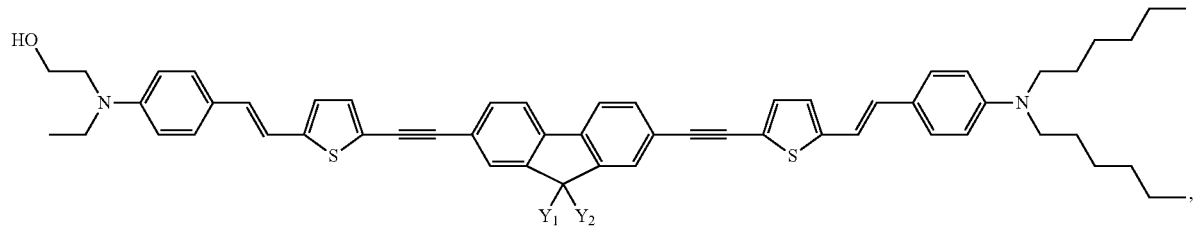
wherein $Y_1$ and $Y_2$ are similar and represent n-butyl alkyl chain or —(CH$_2$CH$_2$)O(CH$_2$CH$_2$)O(CH$_2$CH$_2$)OCH$_3$ groups,
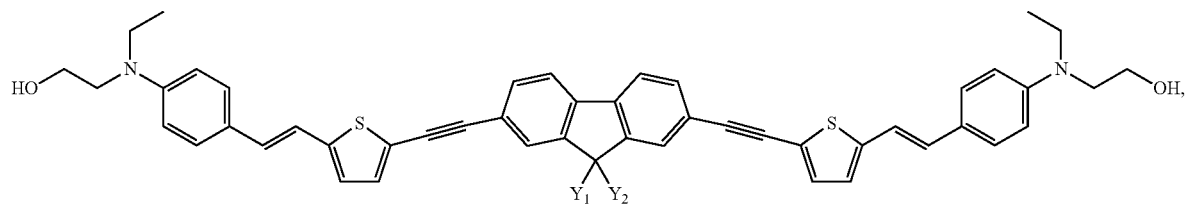
30
wherein $Y_1$ and $Y_2$ are similar and represent n-butyl alkyl chain or —(CH$_2$CH$_2$)O(CH$_2$CH$_2$)O(CH$_2$CH$_2$)OCH$_3$ groups,
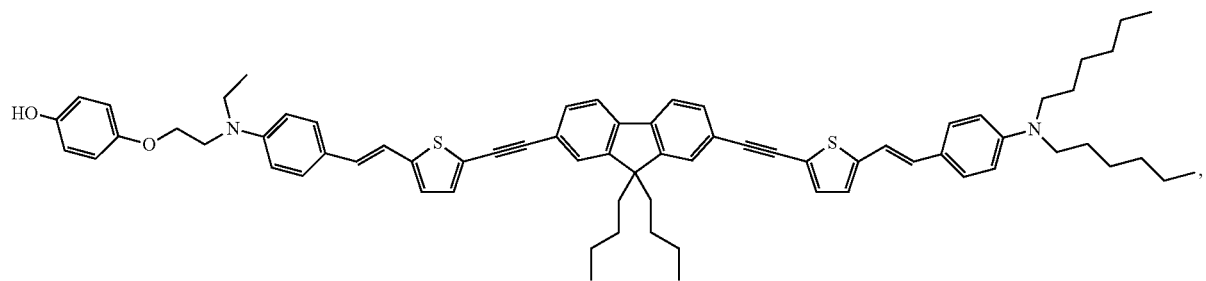
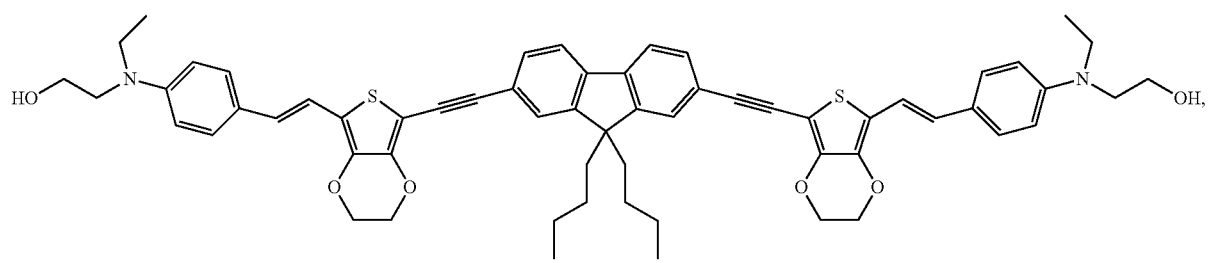

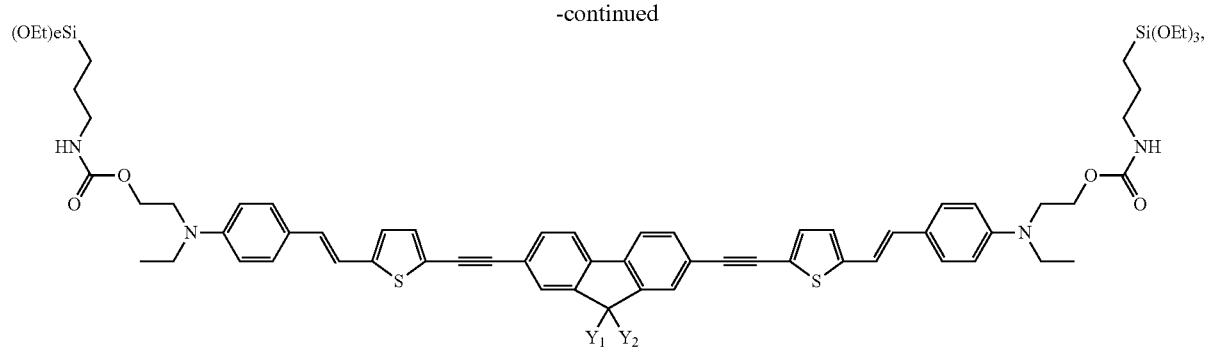
wherein Y₁ and Y₂ are similar and represent —(CH$_2$CH$_2$)O((CH$_2$CH$_2$)O)$_2$CH$_3$ groups,
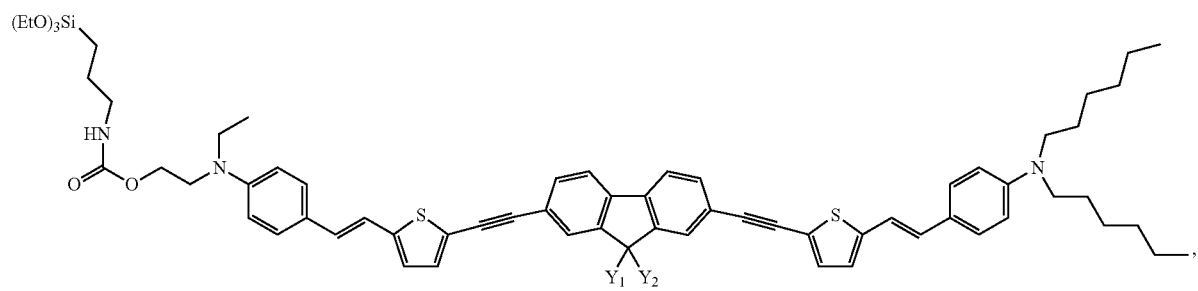
wherein Y₁ and Y₂ are similar and represent —(CH$_2$CH$_2$)O((CH$_2$CH$_2$)O)$_2$CH$_3$ groups,

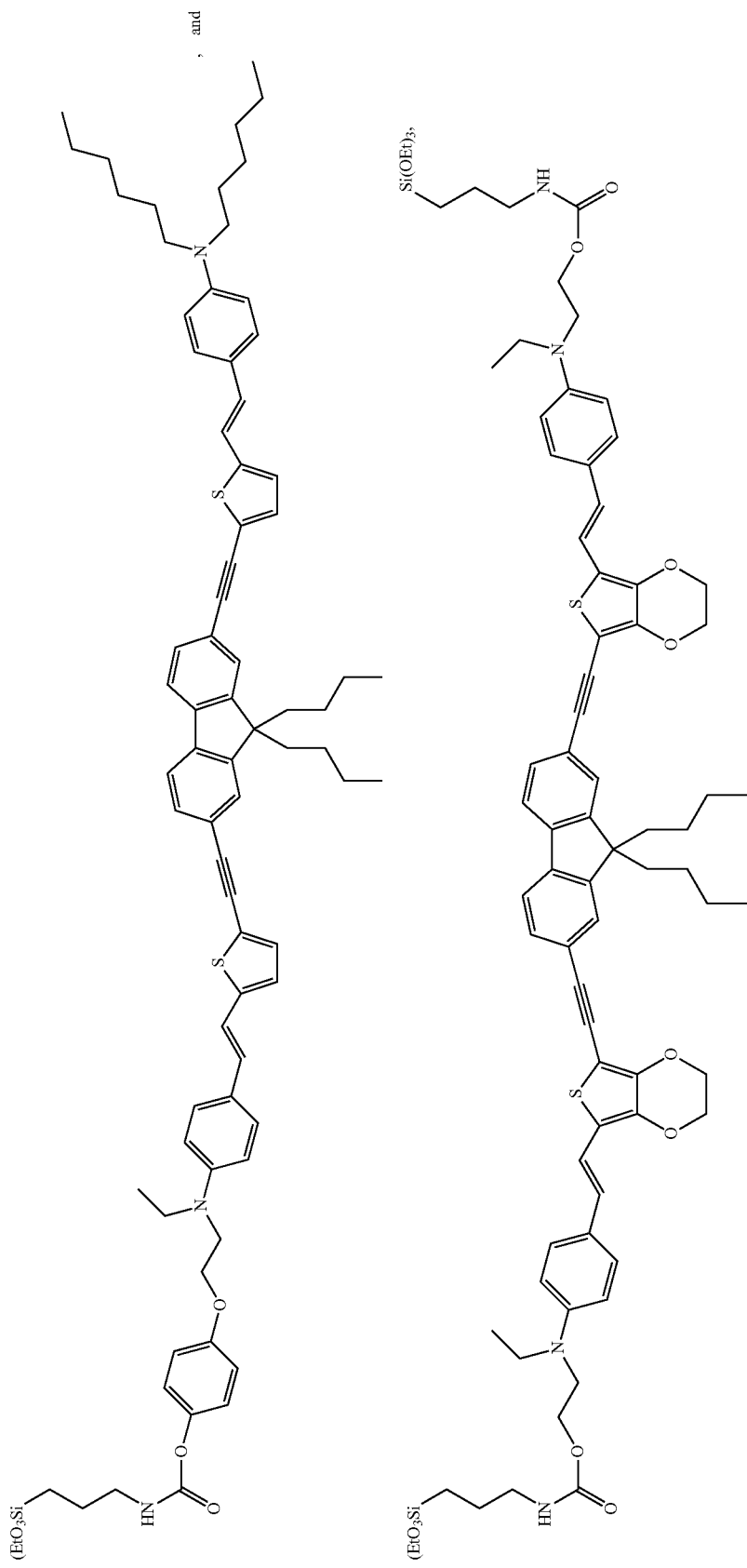

or
(ii) at least one silica nanoparticle composition, comprising at least one silica nanoparticle comprising at least one photosensitizer constituted by said at least one of the compounds, covalently linked to said nanoparticle, and optionally comprising shielding moieties grafted on the surface of said nanoparticle, and optionally comprising biotargeting moieties grafted on the surface of said nanoparticle and a pharmaceutically acceptable carrier.

15. A method for preparing a compound according to claim 1, wherein at least one of the group $Z_1$, $Z_2$, $Z_2$, and $Z_4$ represents a group V, said group V being a molecular clip, comprising
preparing a reaction mixture comprising a compound of formula (I):

(I)

[Chemical structure of formula (I)]

wherein
the groups A and B represent independently from each other —CH=CH—, or —C≡C—,
the terms t, u, v, and w represent, independently from each other, values ranging from 0 to 9,
the groups $Y_1$ and $Y_2$ represent independently from each other:
  a hydrogen atom, or
  an alkyl group linear, branched or substituted, carrying from 1 to 9 carbon atoms, or
  a polyethylene glycol chain of formula: —$(CH_2)_n$—O—$(CH_2CH_2O)_m CH_3$, wherein n<4 and m varies from 1 to 6, or
  an ammonium group of formula: —$(CH_2)_p$—$NR_3^+X^-$, wherein $X^-$ is selected from the group consisting of halogens, tosylate, sulphate, phosphate, $NTf_2$, and $PF_6$ anions, p varies from 1 to 6, and R is an alkyl chain linear or branched, from 1 to 9 carbon atoms,
the groups $Z_1$, $Z_2$, $Z_3$, and $Z_4$ represent independently from each other:
  a hydrogen atom, or
  a group W, said group W being a chemically reactive group, or
  an aryl, aryloxy, aralkyl, aralkyloxy, heteroaryl, or heteroaryloxy group, ranging from 1 to 10 carbon atoms, containing a chemically reactive group W as above defined, or
  an alkyl chain optionally unsaturated, linear, branched or substituted, ranging from 1 to 10 carbon atoms, or
  an alkyl chain optionally unsaturated, linear, branched or substituted, ranging from 1 to 10 carbon atoms, and containing said chemically reactive group W, or
  a polyethylene glycol chain of formula —$(CH_2)_q$—O—$(CH_2CH_2O)_r$—$CH_2CH_2$—W, wherein q<4 and r varies from 1 to 6, and W is said chemically reactive,
provided at least one of the $Z_1$, $Z_2$, $Z_3$ or $Z_4$ groups represents:
  said chemically reactive group W, or
  an aryl, aryloxy, aralkyl, aralkyloxy, heteroaryl, or heteroaryloxy group, ranging from 1 to 10 carbon atoms, containing said chemically reactive group W, or
  an alkyl chain optionally unsaturated, linear, branched or substituted, ranging from 1 to 10 carbon atoms, and containing a chemically reactive group W as above defined, or
  a polyethylene glycol chain of formula —$(CH_2)_q$—O—$(CH_2CH_2O)_r$—$CH_2CH_2$—W, wherein q<4 and r varies from 1 to 6, and W is said chemically reactive group,
the groups $Z_5$ and $Z_6$ represent independently from each other:
  a hydrogen atom, or
  an alkyl chain optionally unsaturated, linear, branched or substituted, ranging from 1 to 9 carbon atoms, or
  an alkoxy group, a carbocyclic group, a heterocyclic group, or an aromatic group, ranging from 1 to 9 carbon atoms, or
  $Z_5$ and $Z_6$ are linked together through an ethylene glycol group, thus providing a 3,4-ethylenedioxythiophene group (EDOT) with the thiophene group they are linked to,

[Chemical structure of EDOT]

EDOT

16. A method for preparing a silica nanoparticle composition comprising at least one silica nanoparticle comprising at least one compound used as a photosensitizer according to formula (I):

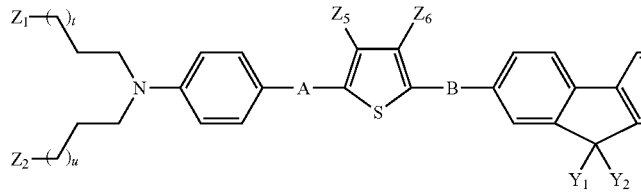

(I)

wherein at least one of the $Z_1$, $Z_2$, $Z_3$ or $Z_4$ groups represents a group V, said group V being a molecular clip constituted by -α-β-δ wherein:
α is a functional linking group and
β is an alkyl chain, linear or branched, containing from 1 to 9 carbon atoms, and
δ is a $Si(OR')_3$ group, wherein R' is an alkyl chain, linear or branched, from 1 to 9 carbon atoms, said method comprising preparing a reaction mixture comprising at least one compound according to formula (I):

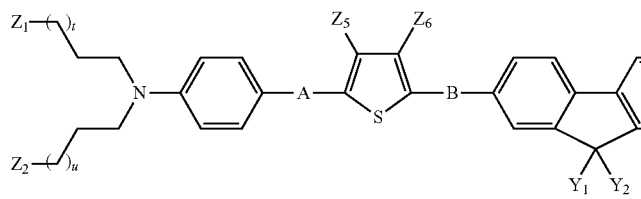

(I)

wherein
the groups A and B represent independently from each other —CH=CH—, or —C≡C—,
the terms t, u, v, and w represent, independently from each other, values ranging from 0 to 9,
the groups $Y_1$ and $Y_2$ represent independently from each other:
a hydrogen atom, or
an alkyl group linear, branched or substituted, carrying from 1 to 9 carbon atoms, or
a polyethylene glycol chain of formula: —$(CH_2)_n$—O—$(CH_2CH_2O)_m CH_3$, wherein n<4 and m varies from 1 to 6, or
an ammonium group of formula: —$(CH_2)_p$—$NR_3^+X^-$, wherein $X^-$ is selec from the group consisting of halogens, tosylate, sulphate, phosphate, $NTf_2$, and $PF_6$ anions, provided said anion does not quench the fluorescence of the compound of formula (I), p varies from 1 to 6, and R is an alkyl chain linear or branched, from 1 to 9 carbon atoms,
the groups $Z_1$, $Z_2$, $Z_3$, and $Z_4$ represent independently from each other:
a hydrogen atom, or
a group W, said group W being a chemically reactive group, or
an aryl, aryloxy, aralkyl, aralkyloxy, heteroaryl, or heteroaryloxy group, ranging from 1 to 10 carbon atoms, containing a chemically reactive group W as above defined, or
an alkyl chain possibly unsaturated, linear, branched or substituted, ranging from 1 to 10 carbon atoms, or
an alkyl chain possibly unsaturated, linear, branched or substituted, ranging from 1 to 10 carbon atoms, and containing said chemically reactive group W, or
a polyethylene glycol chain of formula —$(CH_2)_q$—O—$(CH_2CH_2O)_r$—$CH_2CH_2$—W, wherein q<4 and r varies from 1 to 6, and W is said chemically reactive group, provided at least one of the $Z_1$, $Z_2$, $Z_3$ or $Z_4$ groups represents:
said chemically reactive group W, or
an aryl, aryloxy, aralkyl, aralkyloxy, heteroaryl, or heteroaryloxy group, ranging from 1 to 10 carbon atoms, containing said chemically reactive group W, or
an alkyl chain possibly unsaturated, linear, branched or substituted, ranging from 1 to 10 carbon atoms, and containing said chemically reactive group W, or
a polyethylene glycol chain of formula —$(CH_2)_q$—O—$(CH_2CH_2O)_r$—$CH_2CH_2$—W, wherein q<4 and r varies from 1 to 6, and W is said chemically reactive group,
the groups $Z_5$ and $Z_6$ represent independently from each other:
a hydrogen atom, or
an alkyl chain possibly unsaturated, linear, branched or substituted, ranging from 1 to 9 carbon atoms, or
an alkoxy group, a carbocyclic group, a heterocyclic group, an aromatic group, ranging from 1 to 9 carbon atoms, or
$Z_5$ and $Z_6$ are linked together through an ethylene glycol group, thus providing a 3,4-ethylenedioxythiophene group (EDOT) with the thiophene group they are linked to,

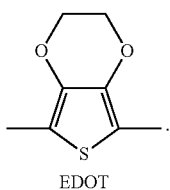

EDOT

17. A method of preparing a nanoparticle according to claim 5, comprising preparing a reaction mixture having a compound of formula (I):

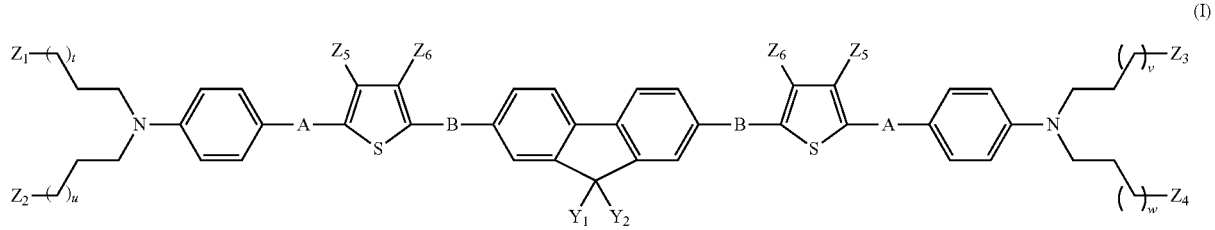

(I)

wherein the groups A and B represent independently from each other —CH=CH—, or —C≡C—, the terms t, u, v, and w represent, independently from each other, values ranging from 0 to 9, the groups $Y_1$ and $Y_2$ represent independently from each other:
- a hydrogen atom, or
- an alkyl group linear, branched or substituted, carrying from 1 to 9 carbon atoms, or
- a polyethylene glycol chain of formula —$(CH_2)_n$—O—$(CH_2CH_2O)_m CH_3$, wherein n<4 and m varies from 1 to 6, or
- an ammonium group of formula: —$(CH_2)_p$—$NR_3^+X^-$, wherein $X^-$ is selected from the group consisting of halogens, tosylate, sulphate, phosphate, $NTf_2$, and $PF_6$ anions, p varies from 1 to 6, and R is an alkyl chain linear or branched, from 1 to 9 carbon atoms, the groups $Z_1$, $Z_2$, $Z_3$, and $Z_4$ represent independently from each other:
- a hydrogen atom, or
- a group V, said group V being a molecular clip constituted by -α-β-δ, wherein:
  - α is a functional linking group, and
  - β is an alkyl chain, linear or branched, containing from 1 to 9 carbon atoms, and
  - δ is a Si(OR')$_3$ group, wherein R' is an alkyl chain, linear or branched, from 1 to 9 carbon atoms, provided at least one of the $Z_1$, $Z_2$, $Z_3$ or $Z_4$ groups represents:
said group V being a molecular clip, the groups $Z_5$ and $Z_6$ represent independently from each other:
- a hydrogen atom, or
- an alkyl chain possibly unsaturated, linear, branched or substituted, ranging from 1 to 9 carbon atoms, or
- an alkoxy group, a carbocyclic group, a heterocyclic group, or an aromatic group, ranging from 1 to 9 carbon atoms, or
- $Z_5$ and $Z_6$ are linked together through an ethylene glycol group, thus providing a 3,4-ethylenedioxythiophene group (EDOT) with the thiophene group they are linked to,

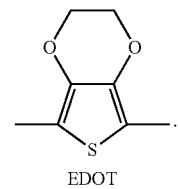

EDOT

18. A method of treating cancer in a subject in need thereof, comprising administering to said subject a therapeutically effective amount of (i) a compound according to claim 1 or (ii) a silica nanoparticle composition, constituted by at least one silica nanoparticle comprising at least one photosensitizer constituted by said compound covalently linked to said nanoparticle, and optionally comprising shielding moieties grafted on the surface of said nanoparticle, and optionally comprising biotargeting moieties grafted on the surface of said nanoparticle.

19. A probe enabling the imaging of cancer cells comprising:
(i) one compound of formula (I):

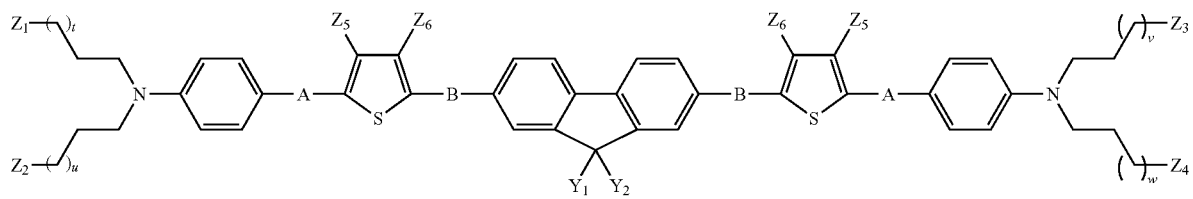

(I)

wherein the groups A and B represent independently from each other —CH=CH—, or —C≡C—, the terms t, u, v, and w represent, independently from each other, values ranging from 0 to 9, the groups $Y_1$ and $Y_2$ represent independently from each other:
- a hydrogen atom, or
- an alkyl group linear, branched or substituted, carrying from 1 to 9 carbon atoms, or
- a polyethylene glycol chain of formula: —$(CH_2)_n$—O—$(CH_2CH_2O)_m CH_3$, wherein n<4 and m varies from 1 to 6, or
- an ammonium group of formula: —$(CH_2)_p$—$NR_3^+ X^-$, wherein $X^-$ is selected from the group consisting of halogens, tosylate, sulphate, phosphate, $NTf_2$, and $PF_6$ anions, provided said anion does not quench the fluorescence of the compound of formula (I), p varies from 1 to 6, and R is an alkyl chain linear or branched, from 1 to 9 carbon atoms, the groups $Z_1$, $Z_2$, $Z_3$, and $Z_4$ represent independently from each other:
- a hydrogen atom, or
- a group W, said group W being a chemically reactive group, or
- a group V, said group V being used as a molecular clip constituted by -α-β-δ, wherein:
  - α is a functional linking group, and
  - β is an alkyl chain, linear or branched, containing from 1 to 9 carbon atoms, and
  - δ is a $Si(OR')_3$ group, wherein R' is an alkyl chain, linear or branched, from 1 to 9 carbon atoms, or
  - an aryl, aryloxy, aralkyl, aralkyloxy, heteroaryl, or heteroaryloxy group, ranging from 1 to 10 carbon atoms, containing said chemically reactive group W, or
  - an alkyl chain optionally unsaturated, linear, branched or substituted, ranging from 1 to 10 carbon atoms, or
  - an alkyl chain optionally unsaturated, linear, branched or substituted, ranging from 1 to 10 carbon atoms, and containing said chemically reactive group W, or
  - a polyethylene glycol chain of formula —$(CH_2)_q$—O—$(CH_2CH_2O)_r$—$CH_2CH_2$—W, wherein q<4 and r varies from 1 to 6, and W is said chemically reactive group, provided at least one of the $Z_1$, $Z_2$, $Z_3$ or $Z_4$ groups represents:
- said chemically reactive group W, or
- said group V being a molecular clip constituted by -α-β-δ, wherein:
  - α is a functional linking group, and
  - β is an alkyl chain, linear or branched, containing from 1 to 9 carbon atoms, and
  - δ is a $Si(OR')_3$ group, wherein R' is an alkyl chain, linear or branched, from 1 to 9 carbon atoms, or
  - an aryl, aryloxy, aralkyl, aralkyloxy, heteroaryl, or heteroaryloxy group, ranging from 1 to 10 carbon atoms, containing said chemically reactive group W, or
  - an alkyl chain optionally unsaturated, linear, branched or substituted, ranging from 1 to 10 carbon atoms, and containing said chemically reactive group W, or
  - a polyethylene glycol chain of formula —$(CH_2)_q$—O—$(CH_2CH_2O)_r$—$CH_2CH_2$—W, wherein q<4 and r varies from 1 to 6, and W is said chemically reactive chemically reactive group, the groups $Z_5$ and $Z_6$ represent independently from each other:
- a hydrogen atom, or
- an alkyl chain optionally unsaturated, linear, branched or substituted, ranging from 1 to 9 carbon atoms, or
- an alkoxy group, a carbocyclic group, a heterocyclic group, or an aromatic group, ranging from 1 to 9 carbon atoms, or
- $Z_5$ and $Z_6$ are linked together through an ethylene glycol group, thus providing a 3,4-ethylenedioxythiophene group (EDOT) with the thiophene group they are linked to,

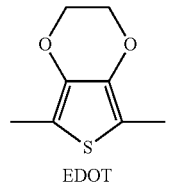

EDOT or (ii) at least one silica nanoparticle comprising at least one of said compound of formula (I).

20. A method of medical imaging of tumours, comprising exposing tumour cells to a probe comprising (i) one compound of formula a compound according to claim 1 or (ii) a silica nanoparticle composition, constituted by at least one silica nanoparticle comprising at least one photosensitizer constituted by said compound covalently linked to said nanoparticle, and optionally comprising shielding moieties grafted on the surface of said nanoparticle, and optionally comprising biotargeting moieties grafted on the surface of said nanoparticle.

* * * * *

UNITED STATES PATENT AND TRADEMARK OFFICE
CERTIFICATE OF CORRECTION

PATENT NO. : 8,709,747 B2  Page 1 of 1
APPLICATION NO. : 13/516010
DATED : April 29, 2014
INVENTOR(S) : Brevet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 57 days.

Signed and Sealed this
Twenty-ninth Day of September, 2015

Michelle K. Lee
*Director of the United States Patent and Trademark Office*